US007523004B2

(12) United States Patent
Bartkowiak et al.

(10) Patent No.: US 7,523,004 B2
(45) Date of Patent: *Apr. 21, 2009

(54) MICROPRESSORS, DEVICES AND METHODS FOR USE IN ANALYTE MONITORING SYSTEMS

(75) Inventors: Miroslaw Bartkowiak, San Jose, CA (US); Wesley S. Harper, San Mateo, CA (US); Eray Kulcu, Coztepe/Izmir (TR); Matthew J. Lesho, San Carlos, CA (US); Janet A. Tamada, Stanford, CA (US)

(73) Assignee: Animas Technologies, LLC, West Chester, PA (US)

( * ) Notice: Subject to any disclaimer, the term of this patent is extended or adjusted under 35 U.S.C. 154(b) by 280 days.

This patent is subject to a terminal disclaimer.

(21) Appl. No.: 11/270,857

(22) Filed: Nov. 9, 2005

(65) Prior Publication Data

US 2006/0085137 A1   Apr. 20, 2006

Related U.S. Application Data

(62) Division of application No. 10/394,516, filed on Mar. 21, 2003.

(60) Provisional application No. 60/367,087, filed on Mar. 22, 2002, provisional application No. 60/413,989, filed on Sep. 25, 2002.

(51) Int. Cl.
*G06F 19/00* (2006.01)
(52) U.S. Cl. ........................................... 702/19
(58) Field of Classification Search ................. None
See application file for complete search history.

(56) References Cited

U.S. PATENT DOCUMENTS

| | | | |
|---|---|---|---|
| 4,325,367 A | 4/1982 | Tapper | |
| 6,144,869 A | 11/2000 | Berner et al. | |
| 6,180,416 B1 | 1/2001 | Kurnik et al. | |
| 6,233,471 B1 | 5/2001 | Berner et al. | |
| 6,272,364 B1 * | 8/2001 | Kurnik | ........................ 600/345 |
| 6,298,254 B2 | 10/2001 | Tamada | |
| 6,326,160 B1 | 12/2001 | Dunn et al. | |
| 6,356,776 B1 | 3/2002 | Berner et al. | |
| 6,546,269 B1 | 4/2003 | Kurnik | |
| 2002/0026110 A1 | 2/2002 | Parris et al. | |

FOREIGN PATENT DOCUMENTS

| | | |
|---|---|---|
| WO | WO 99/29230 | 6/1999 |
| WO | WO 99/58050 | 11/1999 |
| WO | WO 99/58973 | 11/1999 |
| WO | WO 01/88534 | 11/2001 |
| WO | WO 02/15777 | 2/2002 |
| WO | WO 03/000127 | 1/2003 |

OTHER PUBLICATIONS

XU, L., et al., "Optimization Method for Simultaneous Kinetic Analysis", *Analytical Chemistry* 68(11):1842-1850 (Jun. 1996).
Bacon et al., "Predictive, Error-Compensating Kinetic Method for Enzymatic Quantification of Creatinine in Serum," *Clin. Chem.* 37(8):1338-1344 (1991).
Bacon et al., "Kinetic Study of the Jaffe Reaction for Quantifying Creatinine in Serum: 2. Evaluation of Buffered Reagent and Comparison of Different Data-Processing Options," *Clin. Chem.* 35(3):360-363 (1989).
Bellazzi, R. et al., "The Subcutaneous Route to Insulin-Dependent Diabetes Therapy," *IEEE Engineering in Medicine and Biology*, Jan./Feb. 2001, pp. 54-64.
Chen et al., "Evaluation of Alternative Measurement and Data-Processing Options for Enzyme-Based Biosensors," *Analytica Chimica Acta* 388:231-241 (1999).
Clarke, W.L. et al., "Evaluating Clinical Accuracy of Systems for Self-Monitoring of Blood Glucose," *Diabetes Care* 10:622-628 (1987).
Cox, D.J. et al., "Accuracy of Perceiving Blood Glucose in IDDM," *Diabetes Care* 8:529-536 (1985).
Engh et al., "Improvement of Reaction Rate Measurement Precisions Using the Temporally Optimized Fixed-Time Ratemeter," *Anal. Chem.* 60:p. 545 (1988).
Gondo et al., "Studies on Dynamic Behavior of the Biosensor Based on Immobilized Glucoamylase-glucose Oxidase Membrane," *Bions Bioelectron* 12(5):395-401 (1997).
Harris, R.C., "Kinetic Methods that are Independent of the Rate of Reaction," *Clin. Chem.* 29:p. 2079 (1983).
HO, M. H., "Amperometric Enzyme Electrodes," *Biomed. Sci. Instrum.* 20:85-91 (1984).
Kaku et al., "Amperometric Glucose Sensors Based on Immobilized Glucose Oxicase-Polyquinone System," *Anal. Chem.* 66(8):1231-1235 (1994).
Karube et al., "Integrated Microbiosensors for Medical Use," *Ann. N.Y. Acad. Sci.* 542:470-479 (1988).

(Continued)

*Primary Examiner*—John S Brusca

(57) ABSTRACT

The present invention comprises one or more microprocessors programmed to execute methods for improving the performance of an analyte monitoring device including prediction of glucose levels in a subject by utilizing a predicted slower-time constant ($1/k_2$). In another aspect of the invention, pre-exponential terms ($1/c_2$) can be used to provide a correction for signal decay (e.g., a Gain Factor). In other aspects, the present invention relates to one or more microprocessors comprising programming to control execution of (i) methods for conditional screening of data points to reduce skipped measurements, (ii) methods for qualifying interpolated/extrapolated analyte measurement values, (iii) various integration methods to obtain maximum integrals of analyte-related signals, as well as analyte monitoring devices comprising such microprocessors. Further, the present invention relates to algorithms for improved optimization of parameters for use in prediction models that require optimization of adjustable parameters.

5 Claims, 13 Drawing Sheets

OTHER PUBLICATIONS

Kovatchev, B.P. et al., "Risk Analysis of Blood Glucose Data: A Quantitative Approach to Optimizing the Control of Insulin Dependent Diabetes," *J. Theoretical Medicine* 3:1-10 (2001).

Kovatchev, B. P. et al., "Dynamic Network Model of Glucose Counterregulation in Subjects with Insulin-Requiring Diabetes," *Methods Enzymol.* 321:396-410 (2000).

Kovatachev, B. P. et al., "Methods for Quantifying Self-Monitoring Blood Glucose Profiles Exemplified by an Examination of Blood Glucose Patterns in Patients with Type 1 and Type 2 Diabetes," *Diabetes Technology and Therapeutics* 4(3):295-303 (2002).

Kovatchev, B. P. et al., "Symmetrization of the Blood Glucose Measurement Scale and Its Applications," *Diabetes Care* 20(11):1655-8 Nov. 1997.

Kurnik, R. T., "Application of the Mixtures of Experts algorithm for signal processing in a noninvasive glucose monitoring system," *Sensors and Actuators B* 60:19-26 (1999).

Lim et al., "Error-Compensating Kinetic Method for Enzymatic Determination of DNAs," *Clin. Chem.* 28(10):2081-2807 (1982).

Lin et al., "Multipoint Kinetic Methods Evaluated for Quantitation of Theophylline with Prosthetic Group Label Immunoassay," *Clin. Chem.* 39(9):1850-1856 (1993).

Linke et al., "Prevention of the Decrease in Sensitivity of an Amperometric Glucose," *Clin. Chem.* 45(2):283-285 (1999).

Love et al., "Evaluation of Transient Responses of Ammonia-Selective Potentiometric Electrodes for Quantitative Applications," *Analytical Chemistry* 64(II):1269-1276 (1992).

Malitesta et al., "Glucose Fast-Response Amperometric Sensor Based on Glucose Oxidase Immobilized in an Electropolymerized Poly (o-phenylenediamine) Film," *Anal. Chem.* 62(24):2735-2740 (1990).

Meiling et al., "Kinetic Method That is Insensitive to Variables Affecting Rate Constants," *Anal. Chem.* 50:p. 1611 (1978).

Meiling et al., "A Kinetic Method for Glucose That is Insensitive to Variations in Temperature and Enzyme Activity," *Clinical Chemistry* 25(9):1581-1590 (1979).

Pardue, H. L., "Kinetic Aspects of Analytical Chemistry," *Anal. Chem. Acta* 69:216 (1989).

Pardue et al., "Evaluation of a Discrete Sampler/Stopped-Flow Mixer System for Equilibrium and Kenetic Analyses," *Clinical Chemistry* 23(7):1230-1237 (1977).

Pardue, H. L., "Unified View of Kinetic-Based Analytical Methods with Emphasis on Ruggedness," *The Analyst* 121:385-390 (1996).

Przybyt, M., "Influence of Anions on Glucose Electrode Response: Application to Extending Concentration Range," *Biosensors & Bioelectronics* 13(3-4):471-477 (1998).

Rinken et al., "Calibration of Glucose Biosensors by Using Pre-Steady State Kinetic Data," *Biosensors & Bioelectronics* 13(7-8):801-807 (1998).

Tamada, J.A., et al., "Noninvasive Glucose Monitoring," *JAMA* 282(19):1839-1844 (1999).

Tang et al., "Optimisation of Enzyme Electrodes," *Med. Biol. Eng. Comput.* 28(3):B18-24 (1990).

Tapper, R., "Design of an Electronic Antiperspirant Device," *J. Clin. Eng.* 8(3):253-259 (1983).

TSE et al., "Transient Response of an Enzyme Electrode Sensor for Glucose," *Anal. Chem.* 59(19):2339-2344 (1987).

Uhegbu et al., "Initial Studies of a New Approach to the Design and Use of Enzyme-Based Reactor/Sensor Systems: Amperometric System for Glucose," *Anal. Chem.* 65(18):2443-2451 (1993).

Uhegbu et al., "Management of Interferences in a Transdermal, Noninvasive Glucose Monitoring Device," *Clinical Chemistry* 45(9):1679-1681 (1999).

Uhegbu et al., "Data-Processing Method to Reduce Error Coefficients for Membrane-Based Analytical Systems. 1. Ampereometric-Based Sensor Evaluated for Quantification of Oxygen," *Anal. Chem.* 64(20):2378-2382 (1992).

Wentzell et al., "Reaction-Rate Method of Analysis Insensitive to Between-Run Changes in Rate Constant," *Anal. Chem.* 58:p. 851 (1986).

Willis et al., "Simultaneous Kinetic Determination of Mixtures by On-Line Regression Analysis," *Analytical Chemistry* 42(12):1350-1355 (Oct. 1970).

Wollengerber, U., "Electrochemical Biosensors-Ways to Improve Sensor Performance," *Biotechnology Genetic Engineering Reviews* 13:237-266 (1996).

Yokoyama, K., "Mediated Microbiosensors," *Applied Biochemistry Biotechnology Appl. Biochem. Biotechnol.* 41(1-2):17-18 (1993).

* cited by examiner

US 7,523,004 B2

MICROPRESSORS, DEVICES AND METHODS FOR USE IN ANALYTE MONITORING SYSTEMS

CROSS-REFERENCE TO RELATED APPLICATIONS

This application is a Divisional of U.S. application Ser. No. 10/394,516, filed Mar. 21, 2003, and claims the benefit of priority to U.S. Provisional Patent Application No. 60/367, 087, filed Mar. 22, 2002 and U.S. Provisional Application No. 60/413,989, filed Sep. 25, 2002, the contents of which are incorporated herein by reference.

TECHNICAL FIELD

The present invention includes, but is not limited to, one or more microprocessors comprising programming to control execution of methods for improving the performance of an analyte monitoring system that provides a series of analyte-related signals over time; one or more microprocessors programmed to execute the methods and control a sensing device; one or more microprocessors programmed to execute the methods, control a sensing device, and control a sampling device; monitoring systems employing the methods of the present invention; and the methods themselves; as well as algorithms for improved optimization of parameters for use in prediction models that require optimization of adjustable parameters. In one embodiment, the methods relate to glucose monitoring systems, for example, monitoring systems such as GlucoWatch® (Cygnus, Inc., Redwood City, Calif.) biographer monitoring devices, to make more accurate and robust predictions of analyte levels, for example, blood glucose (BG) levels, by utilizing a predicted slower time constant ($1/k_2$). Such a slower time-constant may, for example, be derived from a bi-exponential empirical model, for example, a GlucoWatch biographer monitoring device enzyme reaction-based biosensor current vs. time or calculated charge vs. time data. In another aspect of the invention, the ($1/c_2$) value (wherein $c_2$ (i.e., $c_{slow-reaction}$) is a pre-exponential coefficient) provides a correction for signal decay that can occur in a series of analyte-related signals over time. In other aspects, the present invention relates to one or more microprocessors comprising programming to control execution of (i) methods for conditional screening of data points in order to reduce skipped measurements in an analyte monitoring device, (ii) methods for screening interpolated and/or extrapolated analyte measurement values, (iii) various integration methods that can be used single or in combination to obtain maximum integrals of analyte-related signals; as well as analyte monitoring devices comprising such microprocessors; and the methods themselves. Further, the present invention relates to algorithms for improved optimization of parameters for use in prediction models (e.g., Mixtures of Experts (MOE) that require optimization of adjustable parameters.

BACKGROUND OF THE INVENTION

Measurement and data-processing approaches related to enzyme reaction-based biosensors have historically been based on evaluation of current versus time profiles. Limitations of such analyses include adverse influences on measured values due to changes in experimental variables that influence (a) rates of chemical reactions and (b) physical processes that control the response.

Similar problems have been encountered in conventional kinetic-based methods when they are applied to enzymatic determinations of analytes in homogeneous solutions (Chen, W., et al., Analytica Chimica Acta 388:231-241, 1999). Results of such analyses generally have limited ranges of linearity and are influenced by experimental variables that affect enzyme activity. Data-analysis methods applied to enzyme reaction-based sensors are influenced by variables that affect rates of reaction and rates of mass transport. However, application of initial-rate methods using enzymes in homogenous solution (i.e., kinetic-based solution methods) tend to be influenced only by variables that affect rates of reactions.

A variety of measurement and data-processing approaches have been used in attempts to reduce or eliminate problems in homogenous solution measurement of analyte concentrations including, but not limited to, the following approaches. Engh, et al., (Anal. Chem. 60:545, 1988), used alternative applications of a rate-based approach and showed improvement in the ruggedness of enzymatic methods but also demonstrated that the methods did little to improve the sensitivity at high concentrations of substrate. For homogenous solution analyses, a two-rate method (Wentzell, P. D., et al, Anal. Chem. 58:2851, 1986) and pseudoequilibrium methods (Meiling, G. E., et al., Anal. Chem. 50:1611, 1978; Harris, R. C., Clin. Chem. 29:2079, 1983) have demonstrated the potential to reduce dependencies on experimental variables to a similar degree as has been seen with equilibrium methods.

Two-rate and pseudoequilibrium methods (based on homogenous system methods) have been applied to enzyme reaction-based biosensor methods to determine if these methods could be adapted to biosensors such that measurement improvements would be seen which were similar to those achieved in homogenous solution (Chen, et al., Analytica Chimica Acta 388:231-241, 1999; Wentzell, P. D., et al, Anal. Chem. 58:2851, 1986; Meiling, G. E., et al., Anal. Chem. 50:1611, 1978; Harris, R. C., Clin. Chem. 29:2079, 1983). The enzyme reaction-based biosensor typically used in such studies consisted of an enzyme and an electron mediator immobilized on the surface of a glassy-carbon electrode (e.g., Chen, et al., Analytica Chimica Acta 388:231-241, 1999). Although some improvements in performance characteristics of the enzyme reaction-based biosensor were observed, both methods were shown to have limitations when applied to enzyme reaction-based biosensor data.

Published U.S. Patent Application No. US/2002/0026110 and PCT International Patent Application No. WO 0188534 describe methods for improving performance and reliability of biosensors using a predictive-kinetic (PK) method for data processing of a sensor-generated signal. In these methods, data from a transient region of a signal is used with suitable models and curve-fitting methods to predict the signal that would be measured for the system at the completion of the reaction.

In analyte monitoring devices that employ an electrochemical sensor, signal decay over time can be a significant problem. One method of dealing with signal decay as been to use algorithms that provide signal processing that allow for compensation of signal decay. One such signal processing algorithm is called Mixtures of Experts (MOE) (see, e.g., Kurnik, R. T., Sensors and Actuators B 60, 1 (1999); and U.S. Pat. Nos. 6,180,416, and 6,326,160). However, even current MOE methods only compensate to some extent for signal decay. Typically, standard MOE compensation becomes insufficient, for example, towards the end of long monitoring periods.

The present invention offers methods of improving performance of analyte monitoring systems, for example, that supply a series of analyte-related signals over time. Although aspects of the present invention initially use a similar principle and processing techniques to fit a curve and model the transient data, the present invention employs the fitted variables in a different manner to extract the relevant information. Unlike previous methods employing Predictive Kinetics (PK), one aspect of the present invention employs information from the time constants of exponential functions and pre-exponential terms to provide signal-decay corrections and to predict analyte values. Further methods of improving the performance of analyte monitoring systems are also disclosed.

SUMMARY OF THE INVENTION

The present invention relates to one or more microprocessors comprising programming to control methods described herein; analyte monitoring systems comprising these one or more microprocessors; and the methods themselves which include, but are not limited to, methods for compensating for signal decay, for reducing lag times, for extending usability, for improving accuracy, for reducing noise, for reducing skipped signals, and for improving efficiency. Further, the present invention relates to algorithms for improved optimization of parameters for use in prediction models that require optimization of adjustable parameters.

In a first aspect, the present invention relates to microprocessors, analyte monitoring systems, and methods employing the "$1/k_2$ effect" described herein below. In this first aspect, the present invention comprises one or more microprocessors, comprising programming to control steps of the $1/k_2$ methods described herein. For example, the one or more microprocessors are programmed to control obtaining a measured charge signal over time, comprising a measured charge signal response curve specifically related to the amount or concentration of the glucose extracted from the subject. The measured charge signal response curve comprises a kinetic region. The one or more microprocessors use (i) a mathematical model as presented in Eq. (3A)

$$Q(t) = S_o + \frac{c_1}{k_1}(1 - e^{-k_1 t}) + \frac{c_2}{k_2}(1 - e^{-k_2 t}) \quad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively, and (ii) an error minimization method, to iteratively estimate values of parameters $S_o$, $c_1$, $c_2$, $k_1$, and $k_2$ using the model and an error minimization method to fit a predicted response curve to the kinetic region (or at least a portion of the kinetic region) of the measured charge signal response curve. The error minimization method provides a calculated error based on differences between kinetic regions of the predicted and measured charge signal response curves. The estimating is iteratively performed by one or more microprocessors until the calculated error between the predicted and measured charge signal response curves is minimized or until no further statistically significant change is seen in the calculated error, at which time iterative estimation of the parameters is stopped. The iterative estimation and error minimization results in estimated values of the parameters. The one or more microprocessors then correlate $1/k_2$ with a glucose amount or concentration to provide a measurement of the amount or concentration of the glucose in the subject. Further, the $1/k_2$ parameter may be used as an input parameter for other calculations (e.g., predictive to algorithms such as Mixtures of Experts (MOE)) to provide a measurement of the amount or concentration of glucose.

The one or more microprocessors may be further programmed to control operating associated devices that are in operative combination, for example, a sensing device for obtaining a measured charge signal over time. Further the one or more microprocessors may be programmed to control a measurement cycle comprising (a) operating a sampling device for extracting a sample from the subject, said sample comprising glucose and (b) operating a sensing device for obtaining a measured charge signal over time.

The one or more microprocessors may be further programmed to perform a series of measurement cycles resulting in a series of measured charge signal response curves. When a series measurement cycles are obtained, after estimation of each predicted response curve for each measured charge signal response curve in the series of measurements an amount or concentration of the glucose is calculated by the one or more microprocessors based on each estimated parameter $1/k_2$. This calculation may be, for example, a method comprising applying a calibration value.

When the measured charge signal response curve was obtained by integration of a measured current signal response curve, the one or more microprocessors may be further programmed to control the integration. Further, before the integration is performed, the one or more microprocessors may be further programmed to control a background subtraction correction of the measured current signal response curve.

The present invention also includes monitoring systems comprising the one or more microprocessors described above, wherein the monitoring system further comprises a sensing device used to obtain the measured charge signal response curve, and the one or more microprocessors are further programmed to control operation of the sensing device. In addition, the monitoring system may also comprises a sampling device, and the one or more microprocessors may be further programmed to control operation of the sampling and sensing devices.

The one or more microprocessors may also be programmed to control extracting a sample comprising the glucose from the subject into, for example, one or more collection reservoirs using a sampling device to obtain a concentration of the glucose in the reservoir and the one or more microprocessors are programmed to control operation of the sampling device. The collection reservoirs may be in contact with a skin or mucosal surface of the subject and the glucose may be extracted across the skin or mucosal surface, using, for example, an iontophoretic current applied to the skin or mucosal surface, sonophoresis, or a laser device. The collection reservoirs may comprise an enzyme that reacts with the extracted glucose to produce an electrochemically detectable signal. In one embodiment the enzyme comprises glucose oxidase. When glucose oxidase is used the electrochemically detectable signal is peroxide, the signal may be detected at a reactive surface of a biosensor electrode, the detecting can be accomplished using a sensing device. The one or more microprocessors may be further programmed to control operation of the sensing device. In this embodiment, the kinetic region of the measured charge signal response curve may correspond, for example, to a measurement time period of 0 to about 180 seconds.

In this aspect the present invention includes monitoring systems for frequent measurement of glucose amount or concentration present in a subject. The monitoring system may comprise, in operative combination, a sensing device and one or more microprocessors comprising programming to control a $1/k_2$ method (e.g., as described above). The sensing device is in operative contact with a sample comprising glucose. The sensing device obtains a measured charge signal over time, comprising a measured charge signal response curve, from the glucose, wherein the measured charge signal is specifically related to the amount or concentration of glucose. The measured charge signal response curve comprises a kinetic region. The one or more microprocessors are in operative communication with the sensing device. The one or more microprocessors are capable of controlling the sensing device to obtain a series of measured charge signals, in the form of measured charge signal response curves, at selected time intervals. Further, the one or more microprocessors are programmed to control estimation of a $1/k_2$ value for each measured charge signal in the series.

In addition, the one or more microprocessors of the analyte monitoring device may be programmed to control operation of a sampling device for frequently extracting a sample comprising glucose from the subject, wherein the sampling device is adapted for extracting the glucose across a skin or mucosal surface of the subject, wherein the sampling device is in operative combination with the other components. When the monitoring system comprises a sampling device, the sampling device may comprise one or more collection reservoirs into which samples are collected. Exemplary sampling devices include, but are not limited to, an iontophoretic device, a sonophoretic device, or a laser device, to extract samples comprising glucose from the subject into one or more collection reservoir. One or more collection reservoir may comprises an enzyme that reacts with the extracted glucose to produce an electrochemically detectable signal, for example, glucose oxidase. When glucose oxidase is used the electrochemically detectable signal is peroxide, the signal may be detected at a reactive surface of a biosensor electrode, and the detecting may be accomplished using a sensing device. In this embodiment, the kinetic region of the measured charge signal response curve may correspond to a measurement time period of 0 to about 180 seconds.

This aspect of the present invention also relates to a method of providing a glucose amount or concentration in a subject. In the method, a measured charge signal over time is obtained that comprises a measured charge signal response curve specifically related to the amount or concentration of the glucose extracted from the subject. The measured charge signal response curve comprises a kinetic region. The method uses (i) a mathematical model, for example, the model presented in Eq. (3A)

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively. The method also uses an error minimization method to iteratively estimate values of parameters $c_1$, $c_2$, $k_1$, and $k_2$ using the model and error minimization method to fit a predicted response curve to the kinetic region of the measured charge signal response curve. The error minimization method provides a calculated error based on differences between kinetic regions of the predicted and measured charge signal response curves. Also, the estimating is iteratively performed until the calculated error between the predicted and measured charge signal response curves is minimized or until no further statistically significant change is seen in the calculated error, at which time iterative estimation of the parameters is stopped. The iterative estimation and error minimization results in estimated values of the parameters. The method then correlates $1/k_2$ with a glucose amount or concentration to provide a measurement of the amount or concentration of the glucose in the subject.

In one embodiment, $1/k_2$ is correlated with a glucose amount or concentration to provide a measurement of the amount or concentration of glucose by a method comprising applying a calibration value, for example, using the following equation:

$$[Glu]_t = \frac{[Glu]_{cal}}{(1/k_2)_{cal}}(1/k_2)_t$$

wherein $Glu_t$ is glucose concentration at time t, $Glu_{cal}$ is glucose concentration at a time of calibration that corresponds to an estimated $1/k_2$ at the time of calibration, and $(1/k_2)_t$ is the estimated $1/k_2$ at time t.

In a second aspect, the present invention relates to employing a $1/c_2$ value in correction for signal decay, for example, correcting for signal decay of an electrochemical sensor used for the detection of an amount or concentration of glucose in a subject. This aspect of the invention includes one or more microprocessors to carry out methods of correcting for signal decay of an electrochemical sensor. The one or more microprocessors comprise programming to control obtaining a measured charge signal over time using an electrochemical sensor, wherein the measured charge signal comprises a measured charge signal response curve specifically related to an amount or concentration of glucose extracted from a subject. The measured charge signal response curve comprises a kinetic region. The one or more microprocessors are programmed to use (i) a mathematical model as presented in Eq. (3A)

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively, and (ii) an error minimization method, to iteratively estimate values of parameters $S_o$, $c_1$, $c_2$, $k_1$, and $k_2$ using the model and an error minimization method to fit a predicted response curve to the kinetic region (or at least a portion of the kinetic region) of the measured charge signal response curve. The error minimization method provides a calculated error based on differences between kinetic regions of the predicted and measured charge signal response curves. The estimating is iteratively performed until the calculated error between the predicted and measured charge signal response curves is minimized or until no further statistically significant change is seen in the calculated error, at which time iterative estimation of the parameters is stopped. The iterative estimation and error minimization results in estimated values of the parameters. The one or more microprocessors comprise programming to correct for signal decay of the electrochemical sensor by, for example, multiplying the measured charge signal by a gain factor estimated from $1/c_2$.

The one or more microprocessors may be further programmed to control a measurement cycle. The measurement cycle may comprise operating a sensing device for obtaining a measured charge signal over time. Alternatively, the measurement cycle may comprise (a) operating a sampling device for extracting a sample from the subject, the sample comprising glucose and (b) operating a sensing device for obtaining a measured charge signal over time. The one or more microprocessors may be programmed to perform a series of measurement cycles resulting in a series of measured charge signal response curves. When a series of measurements is used, after estimation of each predicted response curve for each measured charge signal response curve in the series of measurements, the one or more microprocessors may be programmed to determine a gain factor on each estimated parameter $1/c_2$ and multiply each gain factor by the measured charge signal corresponding to the predicted response curve from which the gain factor was estimated. Such a series of measurements may comprise measured charge signal response curves, for example, at times t, t-1, t-2, etc. The one or more microprocessor may be programmed to normalize and/or smooth two or more gain factors from the series of measurements to obtain a normalized and/or smoothed gain factor, and correct for signal decay of the electrochemical sensor by multiplying the measured charge signal at time t by the normalized and/or smoothed gain factor. For example, when the series comprises at least five measured charge signal response curves, and the normalized and/or smoothed gain factor may be calculated based on $(1/c_2)_t$, $(1/c_2)_{t-1}$, $(1/c_2)_{t-2}$, $(1/c_2)_{t-3}$, and $(1/c_2)_{t-4}$, and $(1/c_2)_{t-5}$.

When the measured charge signal response curve was obtained by integration of a measured current signal response curve, the one or more microprocessors may be programmed to control the integration. Further, before the integration is performed the one or more microprocessors may be programmed to control a background subtraction correction of the measured current signal response curve.

In one embodiment, the obtaining of measured charge signal over time comprises extracting a sample comprising the glucose from the subject into one or more collection reservoir using a sampling device to obtain a concentration of the glucose in one or more reservoir. The one or more microprocessors may be programmed to control operation of the sampling device. The collection reservoirs may be for contact with a skin or mucosal surface of the subject and the glucose may be extracted across the skin or mucosal surface using, for example, an iontophoretic current applied to the skin or mucosal surface, sonophoresis, or a laser device. One or more of the collection reservoirs may comprise an enzyme, for example, glucose oxidase, that reacts with the extracted glucose to produce an electrochemically detectable signal. When the enzyme is glucose oxidase, the electrochemically detectable signal is peroxide, the signal may be detected at a reactive surface of the electrochemical sensor, the detecting may be accomplished using a sensing device, and the one or more microprocessors may be programmed to control operation of the sensing device. In this embodiment, a kinetic region of the measured charge signal response curve may correspond to a measurement time period of 0 to about 180 seconds.

The above described one or more microprocessors may be used in a monitoring system. Such a monitoring system may comprise the one or more microprocessors and may further comprise, in operative combination, a sensing device used to obtain the measured charge signal response curve, where the one or more microprocessors are further programmed to control operation of the sensing device. Alternatively, the monitoring system may comprises one or more microprocessors, a sampling device, and a sensing device used to obtain the measured charge signal response curve, all in operative combination, wherein the one or more microprocessors are further programmed to control operation of the sampling and sensing devices.

In one embodiment of this aspect of the present invention, a monitoring system of the present invention may comprise, in operative combination, a sensing device and one or more microprocessor. The sensing device is in operative contact with a sample comprising glucose. The sensing device obtains a measured charge signal over time using an electrochemical sensor. The measured charge signal comprises a measured charge signal response curve, from the extracted glucose, wherein the measured charge signal is specifically related to the amount or concentration of glucose. The measured charge signal response curve comprises a kinetic region. The one or more microprocessors are in operative communication with the sensing device. The one or more microprocessors are capable of controlling the sensing device to obtain a series of measured charge signals, in the form of measured charge signal response curves, at selected time intervals, and estimating a $1/c_2$ value for each measured charge signal in the series. The monitoring system may also include, in operative combination, a sampling device for frequently extracting a sample comprising glucose from a subject, wherein, for example, the sampling device is adapted for extracting the glucose across a skin or to mucosal surface of the subject. The one or more microprocessors are further programmed to control operation of the sampling device. For example, the one or more microprocessors may be programmed to control a measurement cycle comprising (a) operating the sampling device for extracting the sample from the subject and (b) operating a sensing device for obtaining a measured charge signal over time.

In the monitoring system, the sampling device may comprise one or more collection reservoirs into which the sample is collected. The sampling device may comprise an iontophoretic device to extract the sample comprising glucose from the subject into at least one collection reservoir. One or more collection reservoir may comprise an enzyme, for example, glucose oxidase, that reacts with the extracted glucose to produce an electrochemically detectable signal. When the enzyme is glucose oxidase, the electrochemically detectable signal is peroxide, the signal may be detected at a reactive surface of the electrochemical sensor, and the detecting is accomplished using the sensing device.

The method of this aspect of the present invention comprises obtaining a measured charge signal over time using the electrochemical sensor. The measured charge signal comprises a measured charge signal response curve specifically related to the amount or concentration of glucose extracted from the subject. The measured charge signal response curve comprises a kinetic region. The method uses (i) a mathematical model as presented in Eq. (3A)

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively, and (ii) an error minimization method, to iteratively estimate values of parameters $S_o$, $c_1$, $c_2$, $k_1$, and $k_2$ using the model and error minimization method to fit a predicted response curve to the kinetic region of the measured charge signal response curve. The error minimization method provides a calculated error based on differences between kinetic regions of the predicted and measured charge signal response curves. The estimating is iteratively performed until the calculated error between the predicted and measured charge signal response curves is minimized or until no further statistically significant change is seen in the calculated error, at which time iterative estimation of the parameters is stopped. The iterative estimation and error minimization results in estimated values of the parameters. A correction for signal decay of the electrochemical sensor is accomplished by multiplying the measured charge signal by a gain factor estimated from $1/c_2$.

In a third aspect, the present invention provides a method for increasing the effective monitoring time of an analyte monitoring device, for example, a GlucoWatch biographer monitoring device, by employing the $1/k_2$ and/or $1/c_2$ parameters in determination of analyte amount or concentration. For example, the effective monitoring time of a GlucoWatch biographer monitoring device with a single GlucoWatch® (Cygnus, Inc., Redwood City, Calif.) AutoSensor can be extended for up to and beyond 24 hours. Further, these parameters ($1/k_2$ and/or $1/c_2$) may be used as input parameters into other algorithms, for example, MOE, to refine estimates of analyte amount or concentration.

In a fourth aspect, the present invention relates to qualifying skin conductance measurements (i.e., sweat readings). In one embodiment, this aspect of the invention comprises one or more microprocessors comprising programming to control providing a measurement value related to glucose amount or concentration in a subject, a skin conductance reading associated in time with the glucose measurement value, and one or more further data integrity screens associated with the glucose measurement value. The measurement value is accepted when either (i) the skin conductance reading and the one or more further data integrity screens fall within predetermined acceptable ranges or within predetermined threshold values, or (ii) the skin conductance reading falls outside of predetermined acceptable range or beyond predetermined threshold value and the one or more further data integrity screens fall within predetermined acceptable ranges or with predetermined threshold values. The measurement value is skipped (i.e., screened out) when the skin conductance reading falls outside of predetermined acceptable range or beyond predetermined threshold value and one or more of the one or more further data integrity screens fall outside of predetermined acceptable ranges or beyond predetermined threshold values. Further data integrity screens include, but are not limited to peak sensor current and/or background current. In another embodiment, this aspect of the invention comprises an analyte monitoring system. The analyte monitoring system typically comprises one or more microprocessors just described and a sensing device used to provide the measurement value related to glucose amount or concentration, and a skin conductance measurement device used to provide the skin conductance reading, wherein the one or more microprocessors are further programmed to control operation of the sensing device and the skin conductance measurement device. The monitoring device may further comprise a sampling device, wherein the one or more microprocessors are further programmed to control operation of the sampling device to provide a sample comprising glucose. In one embodiment the present invention relates to methods for qualifying skin conductance measurements.

In a fifth aspect, the present invention relates to qualifying analyte-related signals, typically comprising data points having a monotonic trend, wherein one or more data point is non-monotonic. In one embodiment, this aspect of the present invention comprises one or more microprocessors comprising programming to control providing a measurement signal, comprising data points, related to glucose amount or concentration in a subject, wherein the data points typically have a monotonic trend. The data points are evaluated for one or more non-monotonic event, wherein (i) if the data points have an acceptable monotonic trend the measurement signal is accepted for further processing, or (ii) if the data points comprise one or more non-monotonic events, then a percent contribution of the one or more non-monotonic events relative to total measurement signal is further evaluated. In situation (ii), if the percent contribution of the one or more non-monotonic events is less than a predetermined threshold value or falls within a predetermined range relative to total measurement signal, then the measurement signal is accepted for further processing. However, if the percent contribution of the one or more non-monotonic events is greater than a predetermined threshold value or falls outside a predetermined range relative to total measurement signal, then the measurement signal is not accepted for further processing and the measurement signal is skipped. Exemplary analyte-related measurement signals include, but are not limited to, current measurement or charge measurement. In another embodiment, this aspect of the invention comprises an analyte monitoring system. The analyte monitoring system typically comprises one or more microprocessors just described and a sensing device used to provide the measurement signal (e.g., related to glucose amount or concentration), wherein the one or more microprocessors are further programmed to control operation of the sensing device. The monitoring device may further comprise a sampling device, wherein the one or more microprocessors are further programmed to control operation of the sampling device to provide a sample comprising the analyte, for example, glucose. In one embodiment the present invention relates to methods for qualifying analyte-related signals, typically comprising data points having a monotonic trend, wherein one or more data point is non-monotonic.

In a sixth aspect, the present invention relates to qualifying whether an unusable (e.g., error-associated) analyte-related signal from a given measurement cycle should be replaced by interpolation or extrapolation. In one embodiment, this aspect of the present invention comprises one or more microprocessors comprising programming to control qualifying whether an unusable analyte-related electrochemical current signal from a given measurement cycle should be replaced by interpolation or extrapolation by applying one or more of the following criteria: (i) if a sensor consistency check value for the measurement cycle falls within a predetermined acceptable range or within a predetermined threshold then the corresponding analyte-related signal may be replaced; (ii) if a change in background current for the measurement cycle falls within a predetermined acceptable range or within a predetermined threshold then the corresponding analyte-related signal may be replaced; (iii) if a change in temperature falls within a predetermined acceptable range or within a predetermined threshold then the corresponding analyte-related signal may be replaced; and (iv) any ratio between sensors that is used in the interpolation/extrapolation calculation must be calculated within a predetermined time period relative to the signals on which such ratio is based. replacing, Then, if the unusable signal is to be replaced in the series of analyte-related signals, the unusable analyte-related signal is estimated by either: (A) if one or more analyte-related signals previous to the unusable analyte-related signal and one or more analyte-related signals subsequent to the unusable analyte related signal are available, then interpolation is used to estimate the unusable, intervening analyte-related signal, or (B) if two or more analyte-related signals previous to the unusable analyte-related signal are available, then extrapolation is used to estimate the unusable, subsequent analyte-related signal. The series of analyte-related signals is typically obtained from an analyte monitoring device over time and each analyte-related signal is related to an amount or concentration of analyte (e.g., glucose) in a subject being monitored with the analyte monitoring device. The one or more microprocessors may be further programmed to control operation of a sensing device that provides analyte-related signal. Further, the one or more microprocessors may be further programmed to control operation of the sampling device that provides a sample comprising the analyte to the sensing device. In another embodiment, this aspect of the invention comprises an analyte monitoring system. The analyte monitoring system typically comprises one or more microprocessors just described and a sensing device used to provide the analyte-related signal (e.g., related to glucose amount or concentration), wherein the one or more microprocessors are further programmed to control operation of the sensing device. The monitoring device may further comprise a sampling device, wherein the one or more microprocessors are further programmed to control operation of the sampling device to provide a sample comprising the analyte, for example, glucose. In one embodiment the present invention relates to methods for qualifying whether an unusable (e.g., error-associated) analyte-related signal from a given measurement cycle should be replaced by interpolation or extrapolation.

In a seventh aspect, the present invention relates to selecting an integration method for an analyte-related current signal. In one embodiment, this aspect of the present invention comprises one or more microprocessors comprising programming to control selecting a current integration method for an analyte-related current signal, wherein the analyte-related current signal comprises data points. In one embodiment a two sensor system is used for detecting the analyte-related current signal and each of the two sensors are electrochemical sensors. Each sensor alternately acts as cathode and anode. A current signal, comprising data points, is detected in a half-measurement cycle from the anode and the cathode and the analyte-related current signal is obtained from the cathode. A background baseline is determined for a given sensor when acting as cathode, for example, from the last two data points of the current signal detected for the same sensor in a previous half-cycle when the sensor acted as an anode. This background baseline is subtracted from the analyte-related current signal and if over-subtraction of the analyte-related current signal occurs, one of the following integration methods is used to determine an analyte-related charge signal based on the analyte-related current signal: (i) stopping integration when the maximum integral is reached and using the maximum integral as the analyte-related charge signal; or (ii) recalculating a background baseline based on the last two data points from the analyte-related current signal at the cathode, subtracting the recalculated background baseline from the analyte-related current signal, and integrating the background subtracted analyte-related current signal to obtain the analyte-related charge signal. In another embodiment, this aspect of the invention comprises an analyte monitoring system. The analyte monitoring system typically comprises one or more microprocessors just described and sensing device used to provide the analyte-related signal (e.g., related to glucose amount or concentration), wherein the one or more microprocessors are further programmed to control operation of the sensing device. The sensing device may, for example, comprise a two sensor system. The monitoring device may further comprise a sampling device, wherein the one or more microprocessors are further programmed to control operation of the sampling device to provide a sample comprising the analyte, for example, glucose. In one embodiment the present invention relates to methods for selecting an integration method for an analyte-related current signal.

In an eighth aspect, the present invention relates to optimization of parameters for use in a model that requires optimization of adjustable parameters. In one embodiment, this aspect of the present invention comprises one or more computer programs that execute one or more algorithms to optimize parameters for use in a model that requires optimization of adjustable parameters, the one or more algorithms comprising dividing a data set into a training set and a validation set. The model is then trained to determine the adjustable parameters using the training set. The training is stopped before the model parameters have fully converged and the parameters are validated using the validation set, wherein the validated parameters are optimized parameters for use in the model. The validation step insures that the predictions of the model are accurate relative to the independent data of the validation set. One exemplary model that requires optimization of adjustable parameters is a MOE model. The present invention also includes software or firmware comprising such one or more algorithms.

The present invention also includes hardware (e.g., computer systems) for use of such software comprising the algorithms of the present invention. In one embodiment the present invention relates to methods for optimizing parameters for use in a model that requires optimization of adjustable parameters.

In a ninth aspect, the present invention relates to optimization of parameters for use in a prediction model used by an analyte monitoring device, wherein the prediction model requires optimization of adjustable parameters. In one embodiment, this aspect of the present invention comprises one or more computer programs that execute one or more algorithms, wherein the one or more algorithms comprise optimizing the parameters based on multiple analyte readings that quantify two or more regions corresponding to various levels of accuracy for the prediction model used by the analyte monitoring device. One or more of the regions have an associated higher risk (e.g., relative to a clinical outcome such as severe impairment or death) relative to one or more other regions (e.g., an analyte target regions). The optimization of the parameters is carried out until the error associated with the prediction model is minimized in the regions associated with higher risk and acceptable in the one or more other regions. In one embodiment of this aspect of the present invention, the optimizing comprises optimizing a distribution of paired points by, for example, constructing an x-y plane of paired points representing (i) a target analyte amount or concentration measured independently as the x coordinate, and (ii) a corresponding model prediction of target analyte amount or concentration as a paired y coordinate. The model is employed by an analyte monitoring device typically for the estimation or prediction of analyte-related values. The x-y plane is divided into two or more regions corresponding to various levels of accuracy for the model prediction of the analyte monitoring device. Individual mathematical risk functions (F) are constructed that assign a numerical value to each paired point (pp) for a particular region. The individual risk functions are summed to provide a total risk function and the total risk function is minimized to result in optimized parameters for the model. One such exemplary model is a MOE model. An exemplary analyte is glucose. When the exemplary analyte is glucose, the two or more regions corresponding to various levels of accuracy for the prediction model may comprise a hypoglycemic region, a glucose target range, and a hyperglycemic region, and the one or more of the regions that have an associated higher risk relative to one or more other regions comprise the hypoglycemic region and the hyperglycemic region.

The present invention also includes software or firmware comprising such one or more algorithms. The present invention also includes hardware (e.g., computer systems) for use of such software or firmware comprising the algorithms of the present invention. In one embodiment the present invention relates to methods for optimizing parameters for use in a prediction model used by an analyte monitoring device, wherein the prediction model requires optimization of adjustable parameters.

These and other embodiments of the present invention will readily occur to those of ordinary skill in the art in view of the disclosure herein.

BRIEF DESCRIPTION OF THE FIGURES

FIG. 17, panel (b) presents data of 7-minute-integral calibrated charge signal (corresponding to FIG. 16, panel (a)) compensated for signal decay by the normalized gain factor. In this panel, GlucoWatch biographer readings are indicated by a line (where individual measurements are represented as diamonds), BG readings are indicated by circles, and the calibration point is indicated by an asterisk. In the panel, the vertical axis is blood glucose (BG) in mg/dL and the horizontal axis is Elapsed Time in hours (hr).

FIG. 20A (Normal Integration) illustrates a biosensor reading where the previous anodal baseline (based on the last two current readings from the sensor when it acted as anode, sensor B, represented with diamonds) is used to subtract the current signal when the sensor acts as a cathode (sensor B, represented as open circles). If the anodal baseline is used for baseline subtraction an oversubtraction occurs resulting, after integration of the baseline subtracted data, in the integral (represented with open circles and the associated curve) presented in FIG. 20B (Integral=2005 nC). In FIG. 20A the vertical axis is the current reading from the biosensor and the horizontal axis is the elapsed time (ET) in hours:minutes (hh:mm). In FIG. 20 B the vertical axis is the integral (in nC) and the horizontal axis is the elapsed time (ET) in hours:minutes (hh:mm). FIG. 20C presents an alternative approach to integration (Maximum Cumulative Integration) and illustrates a biosensor reading where the previous anodal baseline (based on the last two current readings from the sensor when it acted as anode, sensor B, represented with diamonds) is used to subtract the current signal when the sensor acts as a cathode (sensor B, represented as open circles). However, oversubtraction is not permitted. In this case maximum cumulative integration is employed to provide the integral as shown in FIG. 20D (represented with open circles and the associated curve) (Integral=6325 nC). In FIG. 20C the vertical axis is the current reading from the biosensor and the horizontal axis is the elapsed time (ET) in hours:minutes (hh:mm). In FIG. 20D the vertical axis is the integral (in nC) and the horizontal axis is the elapsed time (ET) in hours:minutes (hh:mm). FIG. 20E presents another alternative approach to integration (Maximum of Previous or This Integration) and illustrates a biosensor reading where the previous anodal baseline (based on the last two current readings from the sensor when it acted as anode, sensor B, represented with diamonds) would have resulted in oversubtraction of the current signal when the sensor acts as a cathode (sensor B, represented as open circles). Instead, the last two readings from the cathodic cycle are used to provide the baseline for baseline subtraction. This results in the maximum integral as shown in FIG. 20F (represented with open circles and the associated curve) (Integral=12273 nC). In FIG. 20E the vertical axis is the current reading from the biosensor and the horizontal axis is the elapsed time (ET) in hours:minutes (hh:mm). In FIG. 20F the vertical axis is the integral (in nC) and the horizontal axis is the elapsed time (ET) in hours:minutes (hh:mm).

DETAILED DESCRIPTION OF THE INVENTION

Figure 1:
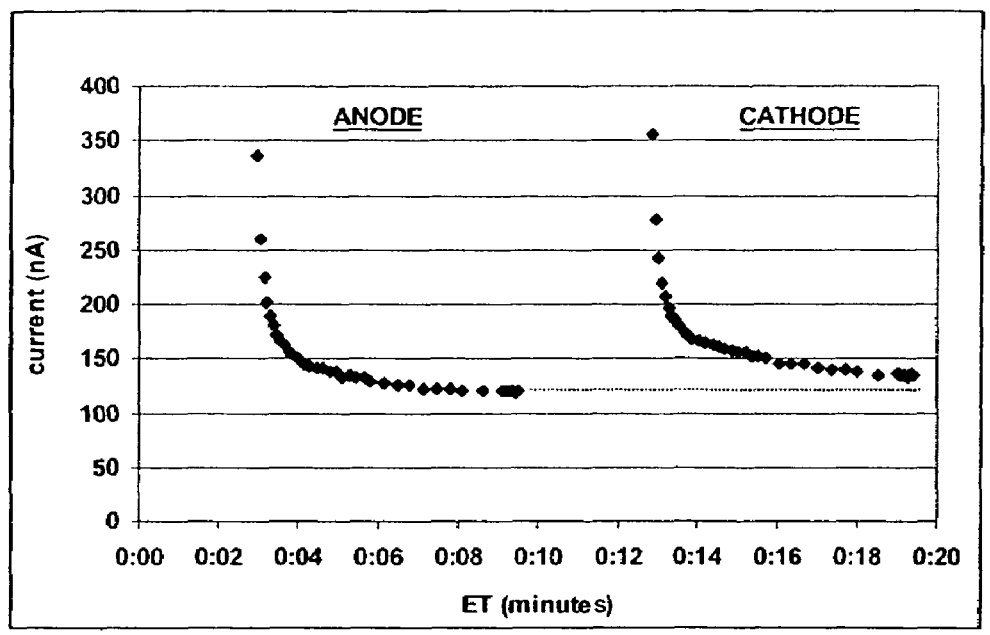
FIG. 1 shows a plot of current (nA) versus elapsed time (ET; minutes)) of a typical full measurement cycle (anode and cathode; i.e., sample anode and cathode cycles) of raw GlucoWatch biographer data.

All patents, publications, and patent applications cited in this specification are herein incorporated by reference as if each individual patent, publication, or patent application was specifically and individually indicated to be incorporated by reference in its entirety for all purposes.

1.0.0 Definitions

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a reservoir" includes a combination of two or more such reservoirs, reference to "an analyte" includes one or more analytes, mixtures of analytes, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "microprocessor" refers to a computer processor contained on an integrated circuit chip, such a processor may also include memory and associated circuits. A microprocessor may further comprise programmed instructions to execute or control selected functions, computational methods, switching, etc. Microprocessors and associated devices are commercially available from a number of sources, including, but not limited to, Cypress Semiconductor Corporation, San Jose, Calif.; IBM Corporation, White Plains, N.Y.; Applied Microsystems Corporation, Redmond, Wash.; Intel Corporation, Chandler, Ariz.; and National Semiconductor, Santa Clara, Calif.

The terms "analyte" and "target analyte" are used to denote any physiological analyte of interest that is a specific substance or component that is being detected and/or measured in a chemical, physical, enzymatic, or optical analysis. A detectable signal (e.g., a chemical signal or electrochemical signal) can be obtained, either directly or indirectly, from such an analyte or derivatives thereof. Furthermore, the terms "analyte" and "substance" are used interchangeably herein, and are intended to have the same meaning, and thus encompass any substance of interest. In preferred embodiments, the analyte is a physiological analyte of interest, for example, glucose, or a chemical that has a physiological action, for example, a drug or pharmacological agent.

A "sampling device," "sampling mechanism," or "sampling system" refers to any device and/or associated method for obtaining a sample from a biological system for the purpose of determining the concentration of an analyte of interest. Such "biological systems" include any biological system from which the analyte of interest can be extracted, including, but not limited to, blood, interstitial fluid, perspiration and tears. Further, a "biological system" includes both living and artificially maintained systems. The term "sampling" mechanism refers to extraction of a substance from the biological system, generally across a membrane such as the stratum corneum or mucosal membranes, wherein said sampling is invasive, minimally invasive, semi-invasive or non-invasive. The membrane can be natural or artificial, and can be of plant or animal nature, such as natural or artificial skin, blood vessel tissue, intestinal tissue, and the like. Typically, the sampling mechanism is in operative contact with a "reservoir," or "collection reservoir," wherein the sampling mechanism is used for extracting the analyte from the biological system into the reservoir to obtain the analyte in the reservoir. Non-limiting examples of sampling techniques include iontophoresis, sonophoresis (see, e.g., PCT International Patent Application No. WO 91/12772; U.S. Pat. No. 5,636,632), suction, electroporation, thermal poration, passive diffusion (see, e.g., PCT International Patent Application Nos.: WO 97/38126; WO 97/42888, WO 97/42886, WO 97/42885, and WO 97/42882; and WO 97/43962), microfine (miniature) lances or cannulas, biolistic (e.g., using particles accelerated to high speeds), subcutaneous implants or insertions, and laser devices (see, e.g., Jacques et al. (1978) J. Invest. Dermatology 88:88-93; PCT International Patent Application No. WO 99/44507; PCT International Patent Application No. WO 99/44638; and PCT International Patent Application No. WO 99/40848). Iontophoretic sampling devices are described, for example, in PCT International Patent Application No. WO 97/24059; European Patent Application No. EP 0942 278; PCT International Patent Application No. WO 96/00110; PCT International Patent Application No. WO 97/10499; U.S. Pat. Nos. 5,279,543; 5,362,307; 5,730,714; 5,771,890; 5,989,409; 5,735,273; 5,827,183; 5,954,685 and 6,023,629. Further, a polymeric membrane may be used at, for example, the electrode surface to block or inhibit access of interfering species to the reactive surface of the electrode.

The term "physiological fluid" refers to any desired fluid to be sampled, and includes, but is not limited to, blood, cerebrospinal fluid, interstitial fluid, semen, sweat, saliva, urine and the like.

The term "artificial membrane" or "artificial surface" refers to, for example, a polymeric membrane, or an aggregation of cells of monolayer thickness or greater which are grown or cultured in vivo or in vitro, wherein said membrane or surface functions as a tissue of an organism but is not actually derived, or excised, from a pre-existing source or host.

A "monitoring system," "analyte monitoring system," or "analyte monitoring device" refers to a system useful for obtaining frequent measurements of a physiological analyte present in a biological system (e.g., analyte amount or concentration in blood or interstitial fluid). Such a system may comprise, but is not limited to, a sensing device and one or more microprocessors in operative combination with the sensing device, or a sampling device, a sensing device, and one or more microprocessors in operative combination with the sampling device and the sensing device.

A "measurement cycle" typically comprises extraction of an analyte from a subject, using, for example, a sampling device, and sensing of the extracted analyte, for example, using a sensing device, to provide a measured signal, for example, a measured signal response curve. A complete measurement cycle may comprise one or more sets of extraction and sensing.

The term "frequent measurement" refers to a series of two or more measurements obtained from a particular biological system, which measurements are obtained using a single device maintained in operative contact with the biological system over a time period in which a series of measurements (e.g., second, minute or hour intervals) is obtained. The term thus includes continual and continuous measurements.

The term "subject" encompasses any warm-blooded animal, particularly including a member of the class Mammalia such as, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex and, thus, includes adult and newborn subjects, whether male or female.

The term "transdermal" includes both transdermal and transmucosal techniques, i.e., extraction of a target analyte across skin, for example, stratum corneum, or mucosal tissue. Aspects of the invention, which are described herein in the context of "transdermal," unless otherwise specified, are meant to apply to both transdermal and transmucosal techniques The term "transdermal extraction" or "transdermally extracted" refers to any sampling method, which entails extracting and/or transporting an analyte from beneath a tissue surface across skin or mucosal tissue. The term thus includes extraction of an analyte using, for example, iontophoresis (reverse iontophoresis), electroosmosis, sonophoresis, microdialysis, suction, and passive diffusion. These methods can, of course, be coupled with application of skin penetration enhancers or skin permeability enhancing technique such as various substances or physical methods such as tape stripping or pricking with micro-needles. The term "transdermally extracted" also encompasses extraction techniques which employ thermal poration, laser microporation, electroporation, micro fine lances, micro fine cannulas, subcutaneous implants or insertions, combinations thereof, and the like.

The term "iontophoresis" refers to a method for transporting substances across tissue by way of an application of electrical energy to the tissue. In conventional iontophoresis, a reservoir is provided at the tissue surface to serve as a container of (or to provide containment for) material to be transported iontophoresis can be carried out using standard methods known to those of skill in the art, for example by establishing an electrical potential using a direct current (DC) between fixed anode and cathode "iontophoretic electrodes," alternating a direct current between anode and cathode iontophoretic electrodes, or using a more complex waveform such as applying a current with alternating polarity (AP) between iontophoretic electrodes (so that each electrode is alternately an anode or a cathode). For example, see U.S. Pat. Nos. 5,771,890, 6,023,629, 6,298,254, and PCT International Patent Application No. WO 96/00109.

The term "reverse iontophoresis" refers to the movement of a substance from a biological fluid across a membrane by way of an applied electric potential or current. In reverse iontophoresis, a reservoir is provided at the tissue surface to receive the extracted material, as used in GlucoWatch biographer monitoring devices.

"Electroosmosis" refers to the movement of a substance through a membrane by way of an electric field-induced convective flow. The terms iontophoresis, reverse iontophoresis, and electroosmosis, will be used interchangeably herein to refer to movement of any ionically charged or uncharged substance across a membrane (e.g., an epithelial membrane) upon application of an electric potential to the membrane through an ionically conductive medium.

The term "sensing device" or "sensing mechanism" encompasses any device that can be used to measure the concentration or amount of an analyte, or derivative thereof, of interest. Preferred sensing devices for detecting analytes (e.g., in blood or interstitial fluid) generally include electrochemical devices, optical and chemical devices and combinations thereof. Examples of electrochemical devices include the Clark electrode system (see, e.g., Updike, et al., (1967) Nature 214:986-988), and other amperometric, coulometric, or potentiometric electrochemical devices, as well as, optical methods, for example UV detection or infrared detection (e.g., U.S. Pat. No. 5,747,806). For example, U.S. Pat. No. 5,267,152 to Yang et al. describes a noninvasive technique of measuring blood glucose concentration using near-IR radiation diffuse-reflection laser spectroscopy. Near-IR spectrometric devices are also described in U.S. Pat. No. 5,086,229 to Rosenthal, et al., U.S. Pat. No. 5,747,806, to Khalil, et al., and U.S. Pat. No. 4,975,581, to Robinson, et al. Additional examples include sensing systems used for continuous monitoring of an analyte amount or concentration in a subject, for example, as described in U.S. Pat. Nos. 6,134,461 and 6,175,752.

A "biosensor" or "biosensor device" includes, but is not limited to, a "sensor element" that includes, but is not limited to, a "biosensor electrode" or "sensing electrode" or "working electrode" which refers to the electrode that is monitored to determine the amount of electrical signal at a point in time or over a given time period, which signal is then correlated with the concentration of a chemical compound. The sensing electrode comprises a reactive surface that converts the analyte, or a derivative thereof, to electrical signal. The reactive surface can be comprised of any electrically conductive material such as, but not limited to, platinum-group metals (including, platinum, palladium, rhodium, ruthenium, osmium, and iridium), nickel, copper, and silver, as well as, oxides, and dioxides, thereof, and combinations or alloys of the foregoing, which may include carbon as well. Some biosensor electrode embodiments are described in EP 0 942 278 and GB 2 335 278. Some catalytic materials, membranes, and fabrication technologies suitable for the construction of amperometric biosensors are described by Newman, J. D., et al.(1995) Analytical Chemistry 67:4594-4599.

The "sensor element" can include components in addition to the sensing electrode, for example, it can include a "reference electrode" and a "counter electrode." The term "reference electrode" is used to mean an electrode that provides a reference potential, for example, a potential can be established between a reference electrode and a working electrode. The term "counter electrode" is used to mean an electrode in an electrochemical circuit that acts as a current source or sink to complete the electrochemical circuit. Although it is not essential that a counter electrode be employed where a reference electrode is included in the circuit and the electrode is capable of performing the function of a counter electrode, it is preferred to have separate counter and reference electrodes because the reference potential provided by the reference electrode is most stable when it is at equilibrium. If the reference electrode is required to act further as a counter electrode, the current flowing through the reference electrode may disturb this equilibrium. Consequently, separate electrodes functioning as counter and reference electrodes are preferred.

In one embodiment, the "counter electrode" of the "sensor element" comprises a "bimodal electrode." The term "bimodal electrode" typically refers to an electrode which is capable of functioning non-simultaneously as, for example, both the counter electrode (of the "sensor element") and the iontophoretic electrode (of the "sampling mechanism") as described, for example, U.S. Pat. No. 5,954,685.

The terms "reactive surface" and "reactive face" are used interchangeably herein to mean the surface of the sensing electrode that: (1) is in contact with the surface of an ionically conductive material which contains an analyte or through which an analyte, or a derivative thereof, flows from a source thereof; (2) is comprised of a catalytic material (e.g., a platinum group metal, platinum, palladium, rhodium, ruthenium, or nickel and/or oxides, dioxides and combinations or alloys thereof) or a material that provides sites for electrochemical reaction; (3) converts a chemical signal (e.g., hydrogen peroxide) into an electrical signal (e.g., an electrical current); and (4) defines the electrode surface area that, when composed of a reactive material, is sufficient to drive the electrochemical reaction at a rate sufficient to generate a detectable, reproducibly measurable, electrical signal when an appropriate electrical bias is supplied, that is correlatable with the amount of analyte present in the electrolyte.

An "ionically conductive material" refers to any material that provides ionic conductivity, and through which electrochemically active species can diffuse. The ionically conductive material can be, for example, a solid, liquid, or semi-solid (e.g., in the form of a gel) material that contains an electrolyte, which can be composed primarily of water and ions (e.g., sodium chloride), and generally comprises 50% or more water by weight. The material can be in the form of a hydrogel, a sponge or pad (e.g., soaked with an electrolytic solution), or any other material that can contain an electrolyte and allow passage of electrochemically active species, especially the analyte of interest. Some exemplary hydrogel formulations are described in PCT International Patent Application Nos. WO 97/02811 and WO 00/64533. The ionically conductive material may comprise a biocide. For example, during manufacture of an AutoSensor assembly, one or more biocides may be incorporated into the ionically conductive material. Biocides of interest include, but are not limited to, compounds such as chlorinated hydrocarbons; organometallics; metallic salts; organic sulfur compounds; phenolic compounds (including, but not limited to, a variety of Nipa Hardwicke Inc. liquid preservatives registered under the trade names Nipastat®, Nipaguard®, Phenosept®, Phenonip®, Phenoxetol®, and Nipacide®); quaternary ammonium compounds; surfactants and other membrane-disrupting agents (including, but not limited to, undecylenic acid and its salts), combinations thereof, and the like.

"Hydrophilic compound" refers to a monomer that attracts, dissolves in, or absorbs water. The hydrophilic compounds for use according to the invention are one or more of the following: carboxy vinyl monomer, a vinyl ester monomer, an ester of a carboxy vinyl monomer, a vinyl amide monomer, a hydroxy vinyl monomer, a cationic vinyl monomer containing an amine or a quaternary ammonium group. The monomers can be used to make the polymers or co-polymers including, but not limited to, polyethylene oxide (PEO), polyvinyl alcohol, polyacrylic acid, and polyvinyl pyrrolidone (PVP).

The term "buffer" refers to one or more components which are added to a composition in order to adjust or maintain the pH of the composition.

The term "electrolyte" refers to a component of the ionically conductive medium which allows an ionic current to flow within the medium. This component of the ionically conductive medium can be one or more salts or buffer components, but is not limited to these materials.

The term "collection reservoir" is used to describe any suitable containment method or device for containing a sample extracted from a biological system. For example, the collection reservoir can be a receptacle containing a material that is ionically conductive (e.g., water with ions therein), or alternatively it can be a material, such as a sponge-like material or hydrophilic polymer, used to keep the water in place. Such collection reservoirs can be in the form of a sponge, porous material, or hydrogel (e.g., in the shape of a disk or pad). Hydrogels are typically referred to as "collection inserts." Other suitable collection reservoirs include, but are not limited to, tubes, vials, strips, capillary collection devices, cannulas, and miniaturized etched, ablated or molded flow paths.

A "collection insert layer" is a layer of an assembly or laminate comprising one or more collection reservoir (or collection insert) located, for example, between a mask layer and a retaining layer.

A "laminate" refers to structures comprised of, at least, two bonded layers. The layers may be bonded by welding or through the use of adhesives. Examples of welding include, but are not limited to, the following: ultrasonic welding, heat bonding, and inductively coupled localized heating followed by localized flow. Examples of common adhesives include, but are not limited to, chemical compounds such as, cyanoacrylate adhesives, and epoxies, as well as adhesives having such physical attributes as, but not limited to, the following: pressure sensitive adhesives, thermoset adhesives, contact adhesives, and heat sensitive adhesives.

A "collection assembly" refers to structures comprised of several layers, where the assembly includes at least one collection insert layer, for example a hydrogel. An example of a collection assembly as referred to in the present invention is a mask layer, collection insert layer, and a retaining layer where the layers are held in appropriate functional relationship to each other but are not necessarily a laminate (i.e., the layers may not be bonded together. The layers may, for example, be held together by interlocking geometry or friction).

The term "mask layer" refers to a component of a collection assembly that is substantially planar and typically contacts both the biological system and the collection insert layer. See, for example, U.S. Pat. Nos. 5,827,183, 5,735,273, 6,141,573, 6,201,979, and 6,370,410.

The term "gel retaining layer" or "gel retainer" refers to a component of a collection assembly that is substantially planar and typically contacts both the collection insert layer and the electrode assembly. See, for example, U.S. Pat. Nos. 6,393,318, 6,341,232, and 6,438,414.

The term "support tray" typically refers to a rigid, substantially planar platform and is used to support and/or align the electrode assembly and the collection assembly. The support tray provides one way of placing the electrode assembly and the collection assembly into the sampling system.

An "AutoSensor assembly" refers to a structure generally comprising a mask layer, collection insert layer, a gel retaining layer, an electrode assembly, and a support tray. The AutoSensor assembly may also include liners where the layers are held in approximate, functional relationship to each other. Exemplary collection assemblies and AutoSensor structures are described, for example, U.S. Pat. Nos. 5,827,183, 5,735,273, 6,141,573, 6,201,979, 6,370,410, 6,393,318, 6,341,232, and 6,438,414. These exemplary collection assemblies and AutoSensors may be modified by use of the Ionically conductive materials (e.g., hydrogels) of the present invention. The mask and retaining layers are preferably composed of materials that are substantially impermeable to the analyte (chemical signal) to be detected; however, the material can be permeable to other substances. By "substantially impermeable" is meant that the material reduces or eliminates chemical signal transport (e.g., by diffusion). The material can allow for a low level of chemical signal transport, with the proviso that chemical signal passing through the material does not cause significant edge effects at the sensing electrode.

The terms "about" or "approximately" when associated with a numeric value refers to that numeric value plus or minus 10 units of measure (i.e. percent, grams, degrees or volts), preferably plus or minus 5 units of measure, more preferably plus or minus 2 units of measure, most preferably plus or minus 1 unit of measure.

By the term "printed" is meant a substantially uniform deposition of a conductive polymer composite film (e.g., an electrode ink formulation) onto one surface of a substrate (i.e., the base support). It will be appreciated by those skilled in the art that a variety of techniques may be used to effect substantially uniform deposition of a material onto a substrate, for example, Gravure-type printing, extrusion coating, screen coating, spraying, painting, electroplating, laminating, or the like.

The term "physiological effect" encompasses effects produced in the subject that achieve the intended purpose of a therapy. In preferred embodiments, a physiological effect means that the symptoms of the subject being treated are prevented or alleviated. For example, a physiological effect would be one that results in the prolongation of survival in a patient.

"Parameter" refers to an arbitrary constant or variable so appearing in a mathematical expression that changing it give various cases of the phenomenon represented (McGraw-Hill Dictionary of Scientific and Technical Terms, S. P. Parker, ed., Fifth Edition, McGraw-Hill Inc., 1994). In the context of GlucoWatch biographer monitoring devices, a parameter is a variable that influences the value of the blood glucose level as calculated by an algorithm.

"Decay" refers to a gradual reduction in the magnitude of a quantity, for example, a current detected using a sensor electrode where the current is correlated to the concentration of a particular analyte and where the detected current gradually reduces but the concentration of the analyte does not.

"Skip" or "skipped" signals refer to data that do not conform to predetermined criteria (e.g., error-associated criteria as described in U.S. Pat. No. 6,233,471). A skipped reading, signal, or measurement value typically has been rejected (i.e., a "skip error" generated) as not being reliable or valid because it does not conform with data integrity checks, for example, where a signal is subjected to one or more data screens that invalidate incorrect signals based on one or more detected parameters indicative of a poor or incorrect signal 1.1.0 GlucoWatch Biographer Monitoring Devices The terms "GlucoWatch biographer" and "GlucoWatch G2 biographer" refer to two exemplary devices in a line of GlucoWatch biographer monitoring devices developed and manufactured by Cygnus, Inc., Redwood City, Calif.

GlucoWatch biographers analyte monitoring devices provide automatic, frequent, and noninvasive glucose measurements. The first-generation device, the GlucoWatch® (Cygnus, Inc., Redwood City, Calif.) biographer, provides up to 3 readings per hour for as long as 12 hours after a 3-hour warm-up period and a single blood glucose (BG) measurement for calibration. The second-generation device, the GlucoWatch®G2™ (Cygnus Inc., Redwood City, Calif.) biographer, provides up to six readings per hour for as long as 13 hours after a single BG measurement for calibration. These devices utilize a reverse iontophoresis to extract glucose through the skin. The glucose is then detected by an amperometric biosensor. GlucoWatch biographer monitoring devices are small devices typically worn on the forearm that contain sampling and detection circuitry, and a digital display. Clinical trials on subjects with Type 1 and Type 2 diabetes have shown excellent correlation between GlucoWatch biographer readings and serial finger-stick BG measurements (see, e.g., Garg, S. K., et al., Diabetes Care 22, 1708 (1999); Tamada, J. A., et al., JAMA 282, 1839 (1999)). However, the first-generation GlucoWatch biographer measurement period is limited to 12 hours, due to decay of the biosensor signal during use. The second-generation device extends the measurement period to up to 13 hours. Similar signal decay has also been observed for implantable glucose monitors (Gross, T. M., et al., Diabetes Technology and Therapeutics 2, 49 (2000); Meyerhoff, C., et al., Diabetologia, 35, 1087 (1992); Bolinder, J., et al., Diabetes Care 20, 64 (1997)), for which up to four calibrations per 24 hours of monitoring is recommended to maintain the device accuracy (Medtronic-MiniMed Web Page: *Continuous Glucose Monitoring System, Frequently Asked Questions*, www.minimed.com/doctors/md_products_cgms_cgmsfaq.shtml).

GlucoWatch biographer monitoring devices have several advantages. Clearly their non-invasive and non-obtrusive nature encourages more glucose testing among people with diabetes. Of greater clinical relevance is the frequent nature of the information provided. GlucoWatch biographer monitoring devices provide the more frequent monitoring desired by physicians in an automatic, non-invasive, and user-friendly manner. The automatic nature of the systems also allow monitoring to continue even while the patient is sleeping or otherwise unable to test. The GlucoWatch biographer and GlucoWatch G2 biographer are the only non-invasive, frequent and automatic glucose-monitoring devices approved by the U.S. Food and Drug Administration and commercially available.

1.1.1 Device Description of GlucoWatch Biographer Monitoring Devices

GlucoWatch biographer monitoring devices contain the electronic components that supply iontophoretic current and controls current output and operating time. They also control the biosensor electronics, as well as receive, process, display and store data. Data can also be uploaded from GlucoWatch biographer monitoring devices to a personal computer, a computer network, personal digital assistant device, etc. They have bands to help secure them to sites on the forearm.

The AutoSensor is a consumable part of the devices that provides up to 13 hours of continuous glucose measurement (in the second-generation device). The AutoSensor is discarded after each wear period. It fits into the back of a GlucoWatch biographer monitoring device and contains electrodes for delivery of iontophoretic current, sensor electrodes for sensing the glucose signal, and glucose-oxidase-containing hydrogel pads for glucose collection and conversion to hydrogen peroxide. There are two gel/electrode sets on each AutoSensor, denoted as A and B.

Figure 9:
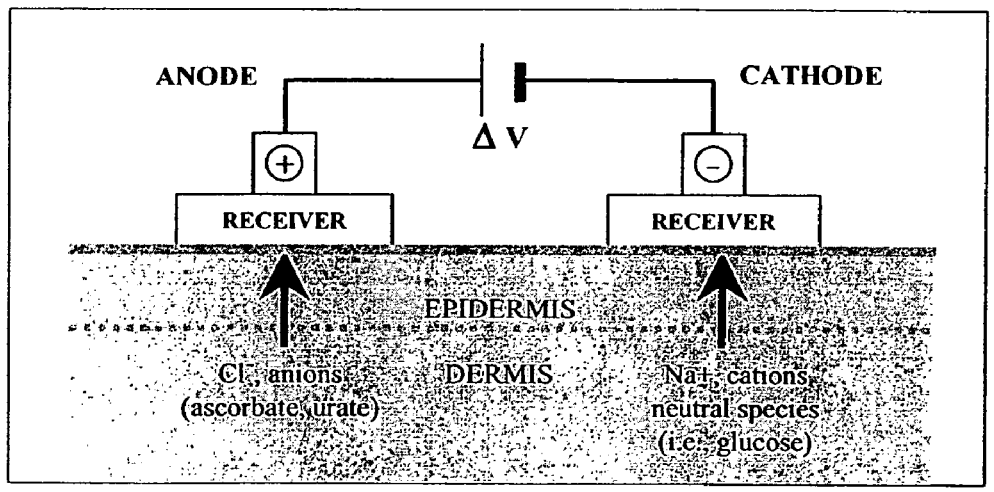
FIG. 9 presents a schematic representation of reverse iontophoresis showing the anode and cathode associated with receivers (e.g., collection reservoirs), and molecules that are extracted across dermis and epidermis that collect at the anode (e.g., $Cl^{-1}$, anions such as ascorbate and urate) and the cathode (e.g., $Na^+$, cations, neutral species such as glucose).

Iontophoresis utilizes the passage of a constant low-level electrical current between two electrodes applied onto the surface of the skin. This technique has been used, for example, to deliver transdermally ionic (charged) drugs (Sinh J., et al., *Electrical properties of skin*, in "Electronically controlled drug delivery," Berner B, and Dinh S M, eds., Boca Raton, La.: CRC Press (1998), pp. 47-62.). On the other hand, electrolyte ions in the body can also act as the charge carriers and can lead to extraction of substances from the body outward through the skin. This process, known as "reverse iontophoresis" or iontophoretic extraction (Rao, G. et al., Pharm. Res. 10, 1751 (2000)) is schematically illustrated in FIG. 9. Because skin has a net negative charge at physiological pH, positively charged sodium ions are the major current carriers across the skin. The migration of sodium ions toward the iontophoretic cathode creates an electro-osmotic flow, which carries neutral molecules by convection. However, only compounds with small molecular weight pass through the skin, so that, for example, no proteins are extracted. Moreover, major interfering species (e.g., ascorbate and urate) are collected at anode. As a result of these unique charge and size exclusion properties of reverse iontophoresis, glucose is preferentially extracted at the cathode, and the obtained sample is very clean. This is in contrast to implantable glucose monitoring devices (Gross, T. M., Diabetes Technology and Therapeutics 2, 49 (2000); Meyerhoff, C., et al., Diabetologia, 35, 1087 (1992); Bolinder, J., et al., Diabetes Care 20, 64 (1997)) for which ascorbate and urate (as well as some proteins) are known to produce an interfering signal.

The feasibility of iontophoretic glucose extraction was demonstrated both in cadaver skin (Glikfeld, P., et al., Pharm. Res. 6, 988 (1989)) and in human subjects (Tamada, J. A., et al., Nat. Med. 1, 1198 (1995)). In feasibility studies with human subjects, glucose transport correlated well with BG in a linear manner. However, the sensitivity (i.e., the amount of glucose extracted) varied among individuals and skin sites (Tamada, J. A., et al., Nat. Med. 1, 1198 (1995)). A single-point calibration was found to compensate for this variability. Reverse iontophoresis yields micromolar concentrations of glucose in the receiver solution, which is about three orders of magnitude less than that found in blood.

To accurately measure this small amount of glucose, GlucoWatch biographer monitoring devices utilize an amperometric biosensor (Tiemey, M. J., et al., Clin. Chem. 45, 1681

(1999)). The glucose oxidase (GOx) enzyme in hydrogel disks (where glucose is collected via reverse iontophoresis) catalyzes the reaction of glucose with oxygen to produce gluconic acid and hydrogen peroxide,

$$\text{Glucose} + O_2 \xrightarrow{\text{GOx}} \text{Gluconic Acid} + H_2O_2$$

Glucose exists in two forms: α and β-glucose, which differ only in the position of a hydroxyl group. At equilibrium (also in blood and in interstitial fluid), the two forms are in proportion of about 37%α and about 63%β. As glucose enters the hydrogel, it diffuses throughout, and only the β-form of glucose reacts with the glucose oxidase enzyme. As β-form is depleted, the α-form then converts (mutarotates) to the β-form. The products of the glucose oxidase reaction (hydrogen peroxide and gluconic acid) also diffuse throughout the gel. Finally, hydrogen peroxide ($H_2O_2$) is detected at a platinum-containing working electrode in the sensor via the electro-catalytic oxidation reaction,

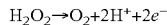

$$H_2O_2 \rightarrow O_2 + 2H^+ + 2e^-$$

producing measurable electrical current, and regenerating $O_2$. Thus, ideally, for every glucose molecule extracted, two electrons are transferred to the measurement circuit. Integration over time of the resulting electric current leads to the total charge liberated at the electrode, and the latter is correlated to the amount of glucose collected through the skin.

Figure 10:
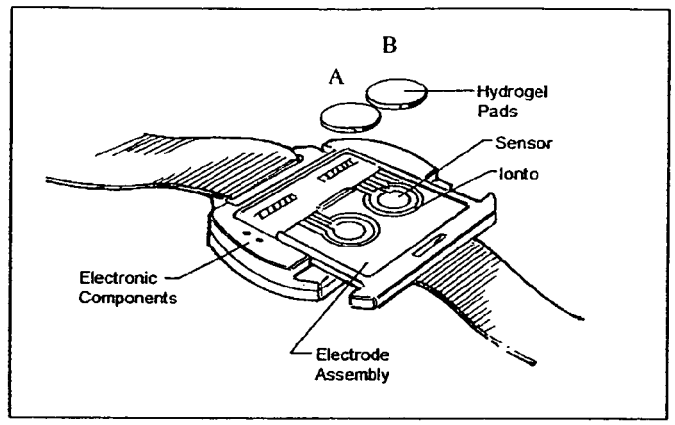
FIG. 10 presents a schematic diagram of exemplary GlucoWatch biographer components including hydrogel pads (A and B), sensor, iontophoretic electrode (ionto), electrode assembly, and electronic components.

An exemplary GlucoWatch biographer monitoring device is shown schematically in FIG. 10. The structure of the second-generation device is very similar (and there are no differences in the AutoSensor). Extraction and detection are achieved using two hydrogel pads (A and B) placed against the skin. The side of each pad away from the skin is in contact with an electrode assembly containing two sets of iontophoretic and sensing elements. The two electrode sets complete the iontophoretic circuit. During operation, one iontophoretic electrode is cathodic and the other anodic, enabling the passage of current through the skin. As a consequence, glucose and other substances are collected in the hydrogel pads during the iontophoretic extraction period. The iontophoretic time interval is adjusted to minimize skin irritation and power requirements, yet extract sufficient glucose for subsequent detection. It has been found that a useful time for extraction of glucose is about three minutes.

On the side of each hydrogel pad, away from the skin and adjacent to the annular iontophoretic electrode, are the sensing electrodes ("Sensor" in FIG. 10). There are two sensing electrodes, noted as sensor A and B. These circular sensing electrodes are composed of a platinum composite, and are activated by applying a potential of 0.3-0.8 V (relative to a Ag/AgCl reference electrode). At these applied potentials, a current is then generated from the reaction of $H_2O_2$ (generated from extracted glucose) that has diffused to the platinum sensor electrode.

1.1.2 Device Operation of GlucoWatch Biographer Monitoring Devices

Figure 11:
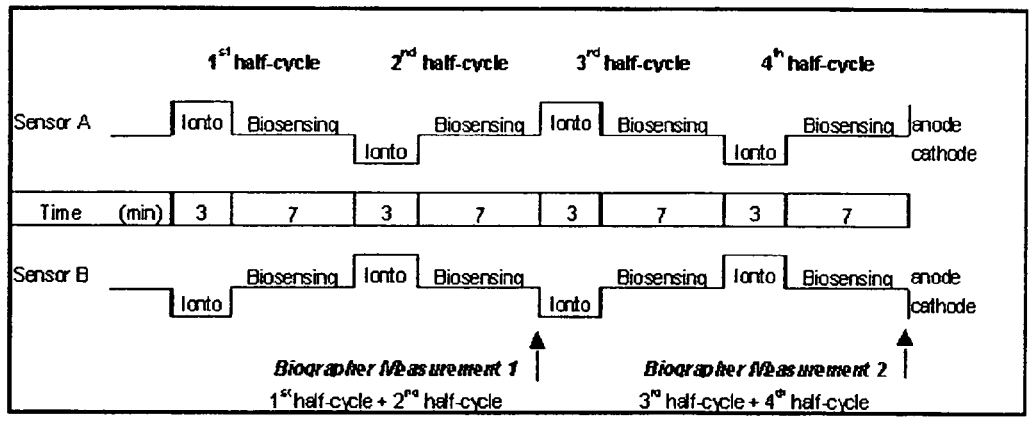
FIG. 11 presents a schematic of the iontophoretic current profile of the extraction (ionto) and detection (biosensing) cycles ($1^{st}$ half-cycle, $2^{nd}$ half-cycle, $3^{rd}$ half-cycle, $4^{th}$ half-cycle) at both sensors (A and B) over time (in minutes) of the GlucoWatch biographer. At the bottom of the figure the GlucoWatch biographer measurement 1 (corresponding to the $1^{st}$ and $2^{nd}$ half-cycles) and GlucoWatch biographer measurement 2 (corresponding to the $3^{rd}$ and $4^{th}$ half-cycles) are illustrated.

Each 20 minute glucose measurement cycle consists of three minutes of extraction, and seven minutes of biosensor activation, followed by three minutes of extraction at the opposite iontophoresis current polarity, and seven additional minutes of biosensor activation. This is schematically illustrated in FIG. 11 for the first-generation GlucoWatch biographer.

In the first half-cycle, glucose is collected in the hydrogel at the iontophoretic cathode (Sensor B). As the glucose is collected, it reacts with the glucose oxidase in the hydrogel to produce hydrogen peroxide ($H_2O_2$). At the end of the three-minute collection period, the iontophoretic current is stopped, and the biosensors activated for seven minutes to measure the accumulated $H_2O_2$. This period is chosen so that the vast majority of the extracted glucose is converted to $H_2O_2$, and that the vast majority of this peroxide diffuses to the platinum electrode, and subsequently oxidizes to generate a current. Because the underlying physical and chemical processes (including, but not limited to, diffusion, glucose mutarotation, and electro-catalytic oxidation reaction at the sensing electrodes) are rather slow, not all of the extracted glucose and $H_2O_2$ is consumed during the seven-minute measurement cycle. However, the integrated current (or charge) signal over this seven-minute interval is sufficiently large and remains proportional to the total amount of glucose that entered the hydrogel pad during the iontophoresis interval. In the process of detection, majority of $H_2O_2$ is depleted. This cleans out the hydrogel to be ready for the next collection period. Moreover, before sensor B will be collecting and measuring glucose again, it has to act as an iontophoretic anode first. The extraction-sensing cycles have been designed so that there will be no peroxide left in the hydrogel after this period. During the initial three-minute period, there is also extraction at the anode (sensor A), primarily of anionic species such as urate and ascorbate. These electrochemically active species are also purged from the anodic reservoir during the seven-minute biosensor period.

In the second half-cycle of the measurement cycle, the Iontophoretic polarity is reversed, so that glucose collection at the cathode occurs in the second reservoir (sensor A), and the anionic species are collected in the first reservoir (sensor B). The biosensor is again activated to measure glucose at the cathode (now sensor A) and to purge electrochemically active species for the anode (sensor B). The combined twenty-minute process is repeated to obtain each subsequent glucose reading.

Figure 12:
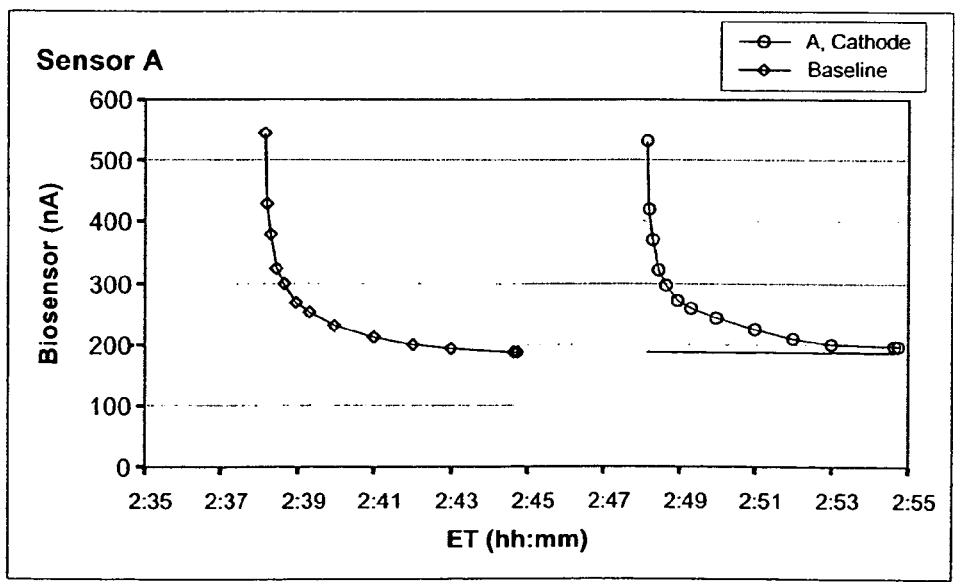
FIG. 12 presents an illustration of raw sensor A current signals for the anodic (diamonds, left-hand side curve) and cathodic (circles, right-hand side curve) cycles. The line in the cathodic cycle represents the anodal baseline background based on the last two readings of the anodic cycle at sensor A. In the figure, the vertical axis is Biosensor (nA) current versus the horizontal axis ET (elapsed time) in hours:minutes (hh:mm).

The raw data for each half-cycle are collected for both A and B sensors as 13 discrete current values measured as functions of time over the seven minutes (providing a measured signal response curve, see, e.g., FIG. 12). Typical current signals for one of the sensors obtained in an anodic (curve with points represented with diamonds) and a subsequent cathodic (curve with points represented with circles) cycle are shown in FIG. 12. When the sensor circuits are activated in the cathodic cycle, $H_2O_2$ (converted from glucose) reacts with the platinum electrode to produce a current, which monotonically declines with time over the seven-minute detection cycle. A current signal of similar shape is also generated in the anodic cycle (curve with data points represented with diamonds). This signal is due, in large part, to ascorbic and uric acids. In both cases the current transients come down to a background of approximately 180 nA rather than zero. The background current, termed the baseline background, does not vary much over time, indicating that it is likely the result of the sum of a number of low concentration species. In order to extract the glucose-related signal only, the background is subtracted from the total current signal. Although the background, once subtracted, does not introduce a significant bias to the glucose measurement, it does significantly decrease the signal-to-noise ratio of the measurement in the hypoglycemic region. This increased noise increases the potential error in the glucose measurement in the hypoglycemic range. It is therefore important to determine the background current as accurately as possible. In some cases there is not enough time in the seven-minute cathodic cycle to consume $H_2O_2$ completely and the current at the end of this cycle is still decreasing. Therefore this measurement cannot be used as a good estimation of the background. On the other hand, it was found that the current stabilizes earlier more consistently in anodic cycles. Therefore, the baseline background is typically determined as the average of the last two current readings of the preceding anodic cycle. This approach (called previous background approach) is illustrated in FIG. 12.

Figure 13:
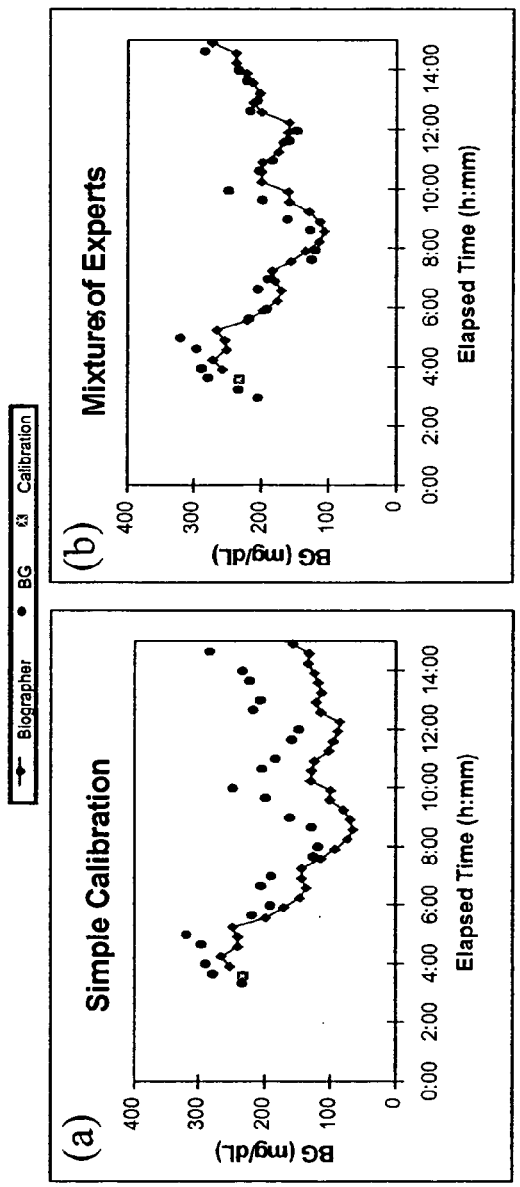
FIG. 13 presents an example of a blood glucose profile as measured by a GlucoWatch biographer calibrated at three hours by matching known blood glucose to the charge signal (panel (a))—these data are shown together with the actual finger stick blood glucose (BG) data. Signal can be seen to decline over time. Panel (b) presents an example of compensation of the signal decay by the Mixtures of Experts (MOE) algorithm. In the figure, GlucoWatch biographer readings are indicated by a line (where individual measurements are represented as diamonds), BG readings are indicated by circles, and the calibration point is indicated by an asterisk. In the figure, the vertical axis is blood glucose (BG) in mg/dL and the horizontal axis is Elapsed Time in hours:minutes (h:mm).

After the background subtraction, the cathodic current signal is integrated to calculate the electrical charge (on the order of µC) liberated at the cathode, which is proportional to the total amount of glucose extracted through the skin. In graphical terms, this corresponds to the calculation of the area between the curve and the line on the right-hand side of FIG. 13. Integration has the added value that it compensates for variations in gel thickness and temperature, as these variables affect only the rate, not the extent of reaction. The integrated signal at the cathodal sensor for each half cycle are averaged as $(C_A+C_B)/2$, a procedure that improves signal-to-noise ratio of the system.

Finally, the averaged charge signal is converted into a glucose measurement based on a patient's finger-stick calibration value (entered at the beginning of the monitoring period). From the calibration, a relationship between charge signal detected by the sensor and blood glucose is determined. This relationship is then used to determine glucose values based on biosensor signal measurements. The latter is achieved by utilizing a signal processing algorithm called Mixtures of Experts (MOE) (Kurnik, R. T., Sensors and Actuators B 60, 1 (1999); U.S. Pat. Nos. 6,180,416, and 6,326,160). The MOE algorithm incorporates: integrated charge signal, calibration glucose value, charge signal at calibration, and time since calibration (i.e., elapsed time). It calculates each glucose reading as a weighted average of predictions obtained from three independent linear models (called Experts), which depend on the four inputs and a set of 30 optimized parameters. Equations to perform this data conversion have been developed, optimized, and validated on a large data set consisting of GlucoWatch biographer and reference BG readings from clinical trials on diabetic subjects. This data conversion algorithm is programmed into a dedicated microprocessor in the GlucoWatch biographer.

The GlucoWatch G2 biographer reduces warm-up time (from three to two hours), increases the number of readings per hour (up to six versus up to three), extends AutoSensor duration (from 12 to 13 hours), and provides predictive low-alert alarms. The increase in the number of readings provided by the GlucoWatch G2 biographer is the result of a modified data processing algorithm that provides a series of moving average values based on the glucose-related signals from sensors A and B. The GlucoWatch G2 biographer uses the same AutoSensor as the first-generation GlucoWatch biographer.

One substantial reason for the limitation of the GlucoWatch biographer and GlucoWatch G2 biographer to measurement periods of about 12-13 hours is substantial signal decay. Both first- and second-generation GlucoWatch biographers, when worn by a subject for an extended period of time, exhibit a decline in response. This is illustrated in FIG. 13(a), where an example blood glucose profile, as measured by a first-generation GlucoWatch biographer calibrated at three hours by matching known blood glucose to the charge signal, is shown together with the actual finger stick BG data. It is seen that the GlucoWatch biographer signal declines over time. As shown in FIG. 13(b), the MOE algorithm, described above, can compensate to some extent for this signal decay.

Figure 14:
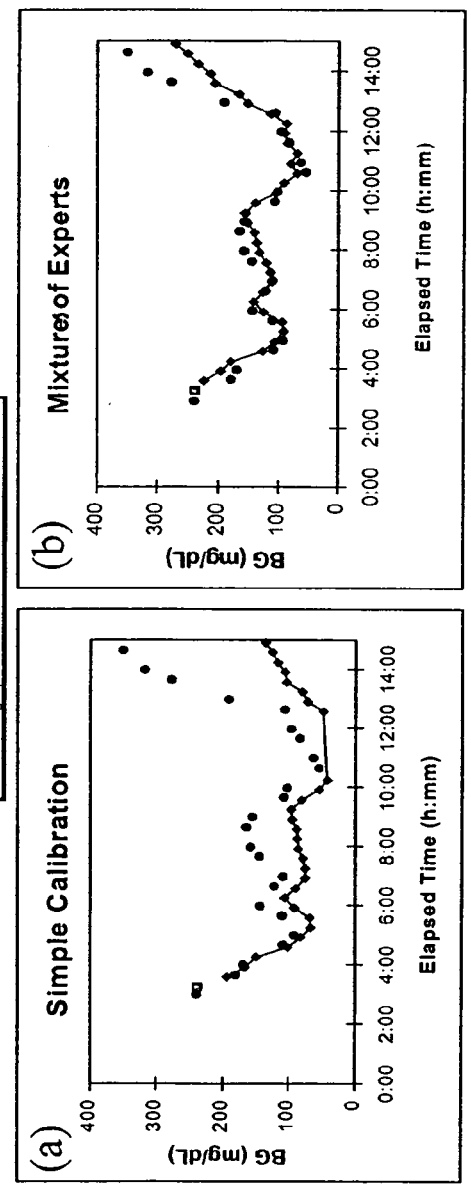
FIG. 14 presents an example of a blood glucose profile as measured by a GlucoWatch biographer calibrated at three hours by matching known blood glucose to the charge signal (panel (a))—these data are shown together with the actual finger stick blood glucose (BG) data. Signal can be seen to decline over time. Panel (b) presents an example of compensation of the signal decay by the MOE algorithm MOE compensation becomes insufficient towards the end of this monitoring period. In the figure, GlucoWatch biographer readings are indicated by a line (where individual measurements are represented as diamonds), BG readings are indicated by circles, and the calibration point is indicated by an asterisk. In the figure, the vertical axis is blood glucose (BG) in mg/dL and the horizontal axis is Elapsed Time in hours:minutes (h:mm).

However, as illustrated in FIG. 14, MOE compensation begins to become insufficient towards the end of the 12-hours monitoring period (for the first-generation device). FIG. 14a presents an example of a blood glucose profile as measured by a GlucoWatch biographer calibrated at three hours by matching known blood glucose to the charge signal. Signal can be seen to decline over time. FIG. 14b presents an example of compensation of the signal decay by the MOE algorithm. As can be seen in FIG. 14b, MOE compensation becomes insufficient towards the end of the 12-hours monitoring period (for the first-generation device). For the second-generation device, MOE compensation becomes insufficient towards the end of the 13-hours monitoring period.

It is not quite clear what causes the observed signal decay. One of the reasons may be the declining sensitivity of the platinum-carbon sensing electrode. However, in contrast to the signal decay observed with human subjects, it is not present in diffusion cells experiments using cadaver skin and applying known amount of glucose. Another possibility is that some peroxide-depleting species come out of the skin, accumulate in the hydrogel and increasingly interfere with glucose detection. Yet another possible reason is that pH of the hydrogel disks (initially phosphate-buffered to pH 7.5) may change after a long contact with the skin, causing reduction of the skin permeability and consequently leading to the observed signal decay. Temporary reduction of skin permeability at the application sites after GlucoWatch biographer use has also been observed, independent of the pH changes.

The glucose readings provided by the GlucoWatch biographers lag the actual blood glucose by about 15-20 minutes. This lag is derived not only from the inherent measurement lag resulting from the time-averaging of glucose signals performed by the GlucoWatch biographers, but also from the physiological differences between the concentration of glucose in interstitial fluid (which is measured by the GlucoWatch biographers) and the instantaneous glucose concentration in blood (as typically measured via a finger prick). The measurement lag is 13.5 minutes. A GlucoWatch biographer glucose reading corresponds to the average glucose concentration in interstitial fluid during the two preceding 3-minute extraction periods (separated by the first 7-minute sensing period) and it is provided to the user after the second 7-minute sensing period, resulting in the 13.5 minute measurement lag, $(3+7+3)/2+7=13.5$, FIG. 11). The additional physiological lag is estimated as about 5 minutes.

The GlucoWatch biographers perform a series of data integrity checks before computing each glucose value. The checks, called screens, selectively prevent certain glucose values from being reported to the user based on certain environmental, physiological, or technical conditions. The screens are based on four measurements taken during the course of wear: current (electrochemical signal), iontophoretic voltage, temperature, and skin surface conductance. Removed points are called skips. For example, if sweat is detected by an increased skin surface conductance, the glucose reading is skipped because the sweat could contain glucose, which could interfere with the glucose extracted from the skin during the iontophoretic period. Other skips are based on noise detected in the signal.

2.0.0 Predictive Kinetics (PK)

Several researchers have investigated Predictive Kinetics (PK) as a quantitative application based on transient response of a system to predict the signal that would be measured if the response were monitored to completion (steady state or equilibrium) (see, e.g., published U.S. Patent Application No. US/2002/0026110 and PCT International Patent Application No. WO 01/88534). In order to predict values at completion, transient data was collected during the early part of the electrode response (typically the kinetic region of the curve) and then modeled with appropriate mathematical functions and curve fitting algorithms as a function of time. The mathematical function is then calculated (via estimation of parameters employing an error minimization algorithm) at time infinity to predict the completion. In these applications, a group of exponential functions was used with the assumption that the time constants should be independent of glucose concentration, thus the glucose concentration should be proportional only to the coefficients.

PK was previously studied as a method to model a first order reaction using kinetic analyses which was insensitive to variables such as pH and temperature (Mieling, G. E., and Pardue H. L., *Anal. Chem.* Page 1611, Vol. 50, 1978.). The method computed the values of rate constant (k), initial absorbance ($S_o$) and final absorbance ($S_\infty$) that fit experimental data to a first order model. Then, the same group applied this method for glucose determination (Mieling G. E. et. al., *Clin. Chem.*, Page 1581, Vol. 25, 1979). In this study, absorbance vs. time data was recorded for a certain period of time ($t_f$) and used to compute the final absorbance ($S_\infty$) that would occur if the reaction were monitored to completion. Also, the change was calculated from the last measured data ($S_f$). A linear relationship was reported between glucose concentration and computed absorbance.

A third study was conducted using the same principle to design enzyme reaction-based reactor/sensor systems (Uhegbu, E. C., et al., *Am. Chem. Soc.*, Page 2443, Vol. 65, 1993). This study was designed to measure the response to reaction of all substrate in a fixed solution, extend the linear measurement range and reduce the dependencies on experimental variables.

A PK application (PK ($S_\infty$)) has been proposed to improve the performance of analyte monitoring devices, for example, GlucoWatch biographer monitoring devices, by increasing the sensitivity (charge vs. reference BG slope), improving the correlation with reference BG and reducing the signal decay in time (see, e.g., published U.S. Patent Application No. US20020026110 and PCT International Patent Application No. WO 01/88534).

This PK ($S_\infty$) method modeled charge vs. time, for example, as a bi-exponential empirical model using PK, and obtained an infinite time charge estimation ($S_\infty$) to be used as the input in the Mixtures of Experts (MOE) algorithm (Kurnik, R. T., Sensors and Actuators B 60, 1 (1999); U.S. Pat. Nos. 6,180,416, and 6,326,160) instead of a employing a 7-minute integral. Estimating the charge with PK ($S_\infty$) improved the sensitivity when it was compared to 7-minute integral method. Following herein this method is discussed in more detail.

Figure 15:
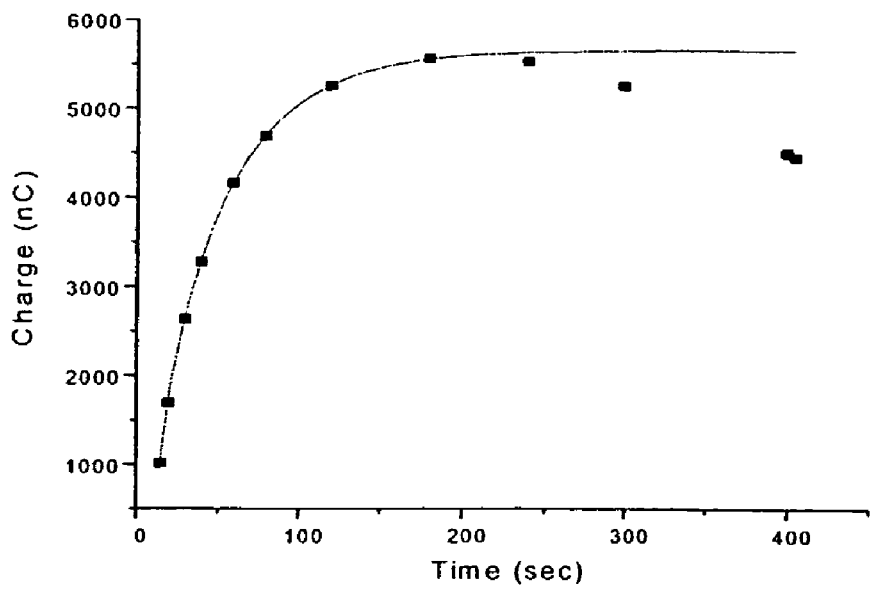
FIG. 15 presents exemplary GlucoWatch biographer charge signal data obtained from direct integration of the background-corrected current signal (points), and by fitting a PK model to the first three-minutes of data. In the figure, the vertical axis is charge (nC) and the horizontal axis is time (seconds). The line represents the maximum integral. The squares represent the data points.

The PK ($S_\infty$) methods are error-compensating data processing methods that use signal from the initial part of a time dependent response curve (transient region) to predict the signal that would be measured for the system at equilibrium (or at completion of all the relevant reactions) (see, e.g., PCT International Patent Application No. WO 01/88534). This is achieved with suitable models and curve-fitting methods. The PK ($S_\infty$) method is exemplified herein with reference to FIG. 15. In FIG. 15, the kinetic portion of the curve is the region from approximately 0-180 seconds and the equilibrium part of the curve is from approximately 180 seconds to 400 seconds. Here an appropriate mathematical model is used to fit to the first three-minute data of a GlucoWatch biographer charge signal. This charge signal (shown in FIG. 15 as points) was obtained from the direct integration of the background-corrected current signal described above. (This method, referred to as the 7-minute fixed-point integration, is used, for example, in the GlucoWatch biographer.) The curve in FIG. 15 represents the result of the nonlinear fitting procedure. It predicts a final charge signal at seven minutes that is substantially larger than the one obtained from direct fixed-point integration of the current signal. Clearly, there is some error with the fixed-point integration result, as negative contributions to the accumulated charge signal should not be obtained (i.e., the true charge signal should not exhibit a downturn). The reason for the error in this particular case is an overestimation of the background current derived from the anodic cycle by using the previous background method. FIG. 12 provides a graphical representation of the previous background method. In the previous background method, the last two data points of the anodic cycle are averaged to establish a baseline value that is then subtracted from the data provided by the cathodic detection cycle (this is described further below). When the previous background is larger than the true background current, the overcorrected current signal becomes negative for long enough times, and leads to the observed downturn in the charge signal. However, as shown in FIG. 15, the PK method effectively compensated for this error. Moreover, one can show that glucose concentration computed from the charge predicted by the PK-type methods should also show reduced dependencies on other experimental variables such as fluctuations of pH, buffer concentration, hydrogel thickness, temperature, and electrode kinetics (sensitivity) of a Pt/C electrode.

In one embodiment, the empirical PK model used to fit the experimental data has the form of a sum of two exponential functions of time, plus a constant term that corresponds to the current background. In other words, the current signal is approximated by the formula, $$I(t) = c_0 + c_1 e^{-k_1 t} + c_2 e^{-k_2 t} \quad \text{(Eq. 1)}$$

where t represents time, I(t) is the current signal at time "t," the baseline background is given by $c_0$, and the pairs ($c_1$, $k_1$) and ($c_2$, $k_2$) could in principle be interpreted as describing two separate first-order-type processes, one of which is faster (e.g., the one indexed by 1) than the other (e.g., the one indexed by 2). Then, $k_1$ and $k_2$ are the apparent decay rates of these hypothetical processes. The terms $c_0$, $c_1$, and $c_2$ are pre-exponential terms that correspond to the electric current contribution at t=0 for the background, first, and second reactions, respectively. In fact, this simple interpretation is justified only to some extent: in the case of glucose detection, mutarotation is one possible physical process that leads to a separate current-signal contribution in the form of an exponential function such as $c_2 e^{-k_2 t}$ in Eq. (1). (While not wishing to be constrained by any particular model, the following discussion is presented to help promote general understanding of the invention. Because mutarotation is usually the slowest process, for the sake of discussion in the present case, it is assigned index 2 herein. However, although mutarotation matches this form it is not necessarily responsible for it.) Parameters describing all the other relevant physical and chemical processes (e.g., diffusion, electrode kinetics, peroxide depletion, etc.) are convoluted in parameters $c_1$ and $k_1$ (as well as in the parameters of additional exponential terms that appear in the exact formula for the current signal, and that are omitted in Eq. (1)).

Consequently, the exponential functions, $c_1 e^{-k_1 t}$ and $c_2 e^{-k_2 t}$, strictly speaking, cannot be interpreted as each describing a single physical process. Nevertheless, Eq (1) (see also, Model (1), below) is called a first-order parallel model. Further, the terms first reaction (or fast reaction) and second reaction (or slow reaction), as used herein, are typically used for convenience of reference to such defined physical processes (e.g., first reaction, $c_1 e^{-k_1 t}$, and second reaction, $c_2 e^{-k_2 t}$) and are not intended to simply imply reference to single-step chemical reactions.

Integration of Eq. (1) leads to the formula for the charge signal as follows:

$$Q(t) = c_o t + \frac{c_1}{k_1}(1 - e^{-k_1 t}) + \frac{c_2}{k_2}(1 - e^{-k_2 t}) \quad \text{(Eq. 2)}$$

In Eq. (2), the terms are the same as defined above and Q(t) is the charge at time "t." Assuming that the background current $c_0$ has been accurately determined and subtracted, and introducing an extra term $S_0$ for additional flexibility, the following PK model for the charge signal is obtained:

$$Q(t) = S_o + \frac{c_1}{k_1}(1 - e^{-k_1 t}) + \frac{c_2}{k_2}(1 - e^{-k_2 t}) \quad \text{(Eq. 3A)}$$

Replacing $c_i/k_i$ with $S_i$ gives the following equation:

$$Q(t) = S_o + S_1(1 - e^{-k_1 t}) + S_2(1 - e^{-k_2 t}) \quad \text{(Eq. 3B)}$$

In this application of PK (referred to herein as $S_\infty$ PK or PK ($S_\infty$)) a bi-exponential model (parallel first order, Eq. 3B) was fit to integral data and the parameters $\{S_0, S_1, S_2, k_1, \text{ and } k_2\}$ were optimized to minimize the error between measured and the estimated charge values. Then, the coefficients $\{S_0, S_1, \text{ and } S_2\}$ were summed to estimate the final charge at $t=\infty$. In Eq. (3B), $\{S_0, S_1 \text{ and } S_2\}$ and Q(t) have units of charge (nC), and $\{k_1 \text{ and } k_2\}$ have units of time$^{-1}$ (1/sec.).

This $S_\infty$ PK application assumes the time constants $\{k_1$ and $k_2\}$ to be independent of glucose concentration and employs only $\{S_0, S_1 \text{ and } S_2\}$ to estimate the charge at time infinity $S_\infty = S_0 + S_1 + S_2$ (final absorbance).

In principle, either Eq. (1) can be fit to the current signal or Eq. (3A or 3B) can be fit to the charge signal, and the resulting parameters should be consistent (e.g., the resulting $k_1$ and $k_2$ should be the same). However, since the charge signal is in general less noisy, the charge curve is preferably used for cycle characterization. The curve shown in FIG. 15 was obtained using Eq. (3A).

The nonlinear fitting (optimization of the model parameters) can be performed using one of the appropriate minimization algorithms, for example, the Levenberg-Marquardt algorithm (a nonlinear curve-fitting algorithm, Press W. H., et al, "Numerical recipes in FORTRAN. The art of scientific computing." Second edition. Cambridge University Press, New York (1994)). Other suitable algorithms will be apparent to one of ordinary skill in the art in view of the present specification. The Levenberg-Marquardt algorithm is a standard nonlinear least-squares routine that works well in practice. It is robust enough to handle noisy signals, and fast enough, so that it can be implemented in a small and not very powerful microprocessor.

Once the PK model has been fitted to an initial portion (typically the first three minutes) of a charge signal, and the parameters $S_i$ and $k_i$ have been determined, the total charge signal $S_\infty$ that would be measured at the completion of the chemical reactions can be estimated from Eq. (3B) by taking $t \to \infty$. The result is the following equation:

$$S_\infty = S_o + S_1 + S_2 \quad \text{(Eq. 4)}$$

Note that $S_\infty$ does not depend on the values of the apparent decay rates $k_1$ and $k_2$. It should give an estimation of the equilibrium charge signal. In some situations, $S_\infty$ correlates with the actual BG values better than the charge signal obtained from the conventional 7-minute fixed-point integration method.

3.0.0 General Overview of the Inventions

Before describing the present invention in detail, it is to be understood that this to invention is not limited to particular types of microprocessors, monitoring systems, computational methods or process parameters, as use of such particulars may be selected in view of the teachings of the present specification. It is also to be understood that the terminology used herein is for the purpose of describing particular embodiments of the invention only, and is not intended to be limiting.

Experiments performed in support of the present invention uncovered an unexpected phenomenon, herein referred to as $1/k_2$ effect. Fitting a bi-exponential model to data from human subjects led to the observation that inverse of the smaller of the apparent rate constants ($k_2$) tracks analyte concentration or amount in a subject being monitored (e.g., blood glucose) surpassingly well. Moreover, the $1/k_2$ signal exhibits little signal decay and can be employed in superior signal processing algorithms. The present invention describes methods to improve of the performance of analyte monitoring devices (e.g., GlucoWatch biographer monitoring devices) and reliability of such devices by utilizing the $1/k_2$ effect. The present invention includes further PK-type signal processing methods useful, for example, to help compensate for decreasing sensitivity of sensors over time. Advantages of the present invention include, but are not limited to, (i) reduction of the signal decay (which, in the context of GlucoWatch biographer monitoring devices, consequently extends monitoring time beyond the typical 12 hours of the GlucoWatch biographer, (ii) reduction of the analyte measurement time (e.g., reduction of the lag time between glucose extraction and GlucoWatch biographer monitoring device reading), (iii) reduction of the number of analyte readings that are not displayed as a result of, for example, data integrity checks (e.g., due to various types of noise in the GlucoWatch biographer monitoring device signal), and (iv) improvement of the overall accuracy of analyte monitoring devices (this method is discussed in further detail herein, e.g., Section 2.0.0 Predictive Kinetics (PK)).

Unlike the previously described methods, the present invention proposes to extract the analyte concentration, for example, glucose concentration, information from the time constants of exponential functions. Although the present invention initially uses a similar principle and processing techniques to fit a curve and model the transient data, it employs different predicted variables to extract the relevant information.

In one aspect of the invention, the slow-reaction constant ($k_2$) is used to calculate analyte amount or concentration. In an exemplary embodiment, Eq. (3A) above is used to model the transient region of a signal response curve (see, e.g., 0-180 seconds of the signal response curve shown in FIG. 15). Other exemplary mathematical equations (models) are presented below. The mathematical model (e.g., Eq. (3A)) is iteratively applied to fit the transient region of the signal response curve. Further, an error minimization algorithm (e.g., Levenberg-Marquart minimization algorithm) is employed in fitting the mathematical function to the curve. Typically, the iterative calculations are continued until an error minimum is located (i.e., when parameters are adjusted outside of their minimized values the error increases). Alternatively, the iterative calculations are concluded when no further significant change is seen in the associated error. After the curve fitting is complete, estimated values of $c_1$, $c_2$, $k_1$ and $k_2$ have been obtained. As described below, $K_{min}$, $K_{ratio}$, and/or $K_{max/min}$ can be used, coupled with a calibration factor to provide an analyte amount or concentration.

$$AC = K_{min}\left(\frac{AC_{calib}}{K_{min/calib}}\right)$$

wherein, AC is the analyte concentration or amount, $K_{min}$ is the slowest time constant (e.g., based on Eq. 3A, $K_{min}$ is $1/k_2$), $AC_{calib}$ is the analyte concentration or amount at the time of calibration, and $K_{min/calib}$ is the slowest time constant at the time of calibration (i.e., obtained from curve fitting and iterative calculation, as described above, where the curve is the signal response curve that corresponds to the analyte calibration measurement taken at the time of calibration).

In another aspect of the present invention, uncorrected charge values, which are subject to signal decay, are multiplied by a corresponding $(1/c_2)$ value to provide a correction for signal decay. For example, for a given charge measurement corresponding to a signal response curve, the slow "c" values are calculated as described above. The reciprocal of this values is then multiplied by the uncorrected charge value to compensate for any signal decay. Because $c_2$ is proportional to signal decay, reciprocals of that value may be used as a gain factor (G) for each cycle to compensate for the signal decay in estimated charge, for example, with the GlucoWatch biographer the 7-minute integral or PK estimated charge. Such a gain factor may be estimated as follows:

$$G = \frac{1}{c_2}$$

As illustrated in FIGS. 14 and 15 (see, Definitions Section, 1.1.2 Device Operation of GlucoWatch biographer monitoring devices), within a limited time framework, a sophisticated algorithm such as Mixtures of Experts (MOE) can be used to compensate for signal decay. Here, however, one aspect of the present invention sets forth a new method to deal with the signal decay problem. In addition to the applications described above, the exponential and pre-exponential factors (e.g., $c_1$, $c_2$, $k_1$, and $k_2$) may be used as input parameters into a MOE algorithm.

In yet another aspect of the present invention, conditional screening of data points is employed in order to reduce skipped measurements in an analyte monitoring device. In one embodiment, if a data screen associated with a measurement value indicates that the measurement value should be skipped, then further, selected data screens associated with that measurement value are examined. If these further, selected data screens fall within acceptable ranges then the measurement value is accepted rather than skipped. In one embodiment of the present invention, measurement values (e.g., glucose amounts or concentrations obtained using an iontophoretic sampling device and electrochemical detection of a signal related to glucose amount or concentration) are screened based on sweat values. If a sweat value (e.g., a skin conductance reading) indicates that an associated measurement value should be skipped, then further data integrity screens are examined (e.g., peak sensor current and/or background current). If the further data integrity screens fall within acceptable ranges, typically empirically determined, then the measurement value is accepted. If one or more of the further data integrity screens fall outside of acceptable ranges then the measurement value is skipped. Because multiple data integrity screens are employed this method is referred to as a composite data integrity screen. In another embodiment of this aspect of the present invention, if data points demonstrating non-monotonicity suggest that an associated measurement value be skipped, then the degree of contribution of the non-monotonic event to the overall signal associated with the measurement value is evaluated. If the degree of contribution (e.g., percentage of signal) of the non-monotonic event is less than a predetermined threshold value or within a predetermined range then the measurement value is accepted. The threshold value or predetermined range is typically, empirically determined. If the degree of contribution (e.g., percentage of signal) of the non-monotonic event is greater than a predetermined threshold value or outside of a predetermined range then the measurement value is skipped. The present invention includes methods related to such composite data integrity screens (typically in the form of a decision tree (i.e., a series of logical if/then statements), one or more microprocessors comprising programming to control execution of the methods, and analyte monitoring systems comprising such one or more microprocessors.

In yet another aspect, the present invention relates to methods for screening interpolated and/or extrapolated analyte measurement values. Typically the screens are carried out before calculation of an interpolated or extrapolated value to determined whether such an interpolated/extrapolated value would be associated with higher than acceptable error, that is, the screens can be used as qualifying factors or criteria. Alternatively, the interpolated/extrapolated value may be calculated then submitted to further screens. Further, additional data screens (such as the composite data integrity checks described herein below) may be applied as well to determine if interpolation and/or extrapolation to provide a missing analyte-related measurement value is even necessary.

For example, interpolated and/or extrapolated values are submitted to data screens in order to identify the best interpolated and/or extrapolated candidate. Additional screens are applied to interpolated and/or extrapolated values to prevent those with a higher than acceptable error from contributing to analyte readings. Exemplary additional screening criteria include, but are not limited to, use of a sensor consistency check (described herein below), screening measurement cycles associated with interpolated/extrapolated measurement values by background drift from calibration (i.e., change in background measurements) and/or delta temperature (i.e., change in temperature measurement over time) values. If such background drift or delta temperature values fall outside of a predetermined, acceptable range or beyond a predetermined threshold value then the corresponding measurement cycle is not used for interpolation and/or extrapolation of a measurement value, i.e., these screens are used to qualify interpolated or extrapolated measurement values.

Further screens may be applied as well to determine if interpolation and/or extrapolation should be carried out for a missing signal. For example, in a two sensor system such as a GlucoWatch biographer monitoring device, another screen for an interpolation or extrapolation is that the ratio between the two sensors used in the interpolation/extrapolation calculation must be calculated within a certain amount of time to from the skipped cycle integral that is being calculated. This may be applied to single sensor systems as well, wherein a time limit is set relative to the length of time that has elapsed since the last clean measurement that will be used in the interpolation/extrapolation calculations. Likewise this approach can be applied to multiple sensor systems having more than two sensors.

Further screens may be applied as well to determine if interpolation and/or extrapolation is actually necessary. For example, if a signal (and corresponding measurement value) have been skipped based on a single screen, a composite data integrity check (as described herein) may indicate that the signal should be accepted rather than skipped.

The present invention comprises methods of screening measurement values obtained by interpolation and/or extrapolation (or a determination if interpolation and/or extrapolation of a measurement value should be carried out), one or more microprocessors comprising programming to control execution of such methods, and analyte monitoring systems comprising such one or more microprocessors.

In yet another aspect of the present invention, various integration methods can be used single or in combinations to obtain maximum integrals (e.g., charge measurements related to analyte amount or concentration). Anodal baseline subtraction can be used for baseline correction before integration. This method may be coupled with a Maximum Cumulative Integration method and/or a Maximum This or Previous Integration method (both further described herein below). Further, a decision tree can be used for selection of an appropriate integration strategy. For example, if there is no over-subtraction, then use the previous anodal baseline for subtraction before integration. If there is over-subtraction, then use Maximum Cumulative Integration. Or in another embodiment, if there is no over-subtraction, then use the previous anodal baseline for subtraction before integration. If there is over-subtraction, then use the last two cathodal measurements for the current cycle to establish the baseline for subtraction before integration.

The present invention comprises methods of alternative integration, methods of selecting the integration mode, one or more microprocessors comprising programming to control execution of such methods, and analyte monitoring systems comprising such one or more microprocessors.

In yet another aspect the present invention relates to improved optimization of parameters for use in MOE-like algorithms (i.e., any model that requires optimization of adjustable parameters). In one embodiment of this aspect of the present invention, one improved optimization method is to stop the MOE training process early, i.e., before the model coefficients have fully converged. One method for choosing when to stop training is cross-validation. In another embodiment of this aspect of the invention, use of alternative penalty functions can lead to a more robust model. Exemplary penalty functions includes, but are not limited to, MARE (mean absolute relative error; used singly or in combination with other functions), Lorenzian Error, Kovatchev's Low/High BG Risk Index (see, e.g., Kovatchev, B. P., et al., J. Theoretical Medicine 3:1-10 (2001)), cost functions (see, e.g., Bellazzi, R. et al., IEEE Engineering in Medicine and Biology, January/February 2001, pages 54-64). Moreover, in order to develop MOE models that exhibit minimal bias the penalty function can be extended to include the absolute difference between the actual Deming slope determined from the MOE model and the desired Deming slope. For example, the penalty function in the MOE training process may be MARE+W|m−$m_T$|, where m is the Deming slope predicted by the MOE model, $m_T$ is the target Deming slope (typically $m_T$=1), and W is a weighting factor that depends on the estimated value of MARE. In yet another embodiment of this aspect of the present invention, optimization of a particular distribution of paired points is used to optimize MOE-type models (and other models with adjustable parameters). A paired point is constructed, for example, by representing the target analyte amount or concentration, for example, glucose concentration value, measured independently as the x coordinate, and the corresponding model prediction value as the paired y coordinate. The x-y plane is then divided into several regions corresponding to various levels of the analyte monitoring device accuracy and possibility of adverse clinical outcome. In one embodiment of the present invention, a mathematical risk function F is constructed that assigns a numerical value to each paired point (pp) in a particular category (region). Individual risk functions are then used to provide a total risk function which can be minimized.

This aspect of the present invention comprises methods of improved optimization of parameters for use in MOE-like algorithms, methods of providing such parameters to such algorithms, algorithms comprising programming to control execution of such methods, and analyte monitoring systems employing such optimized parameters.

In addition to the methods described herein, the present invention comprises one or more microprocessors comprising programming to control the execution of any of the methods described herein singly or in combination. The one or more microprocessors may comprise further programming to control operation of one or more associated devices that are in operative combination (e.g., sensing, sampling, delivery, etc.), execution of one or more measurement cycles, providing values (e.g., measurement values, current values, charge values, etc.), and/or repeating steps. The one or more microprocessors of the present invention may also comprise additional programming, for example, to execute $1/k_2$ methods, $1/c_2$ methods, decision trees, conditional screening methods, interpolation/extrapolation methods, data screening criteria, alternative integration methods, and/or employing optimized parameters. Further, the present invention comprises analyte monitoring systems comprising, for example, one or more microprocessors of the present invention in operative combination with a sensing device, wherein said one or more microprocessors typically further comprise programming to control operation of the sensing device. In addition, analyte monitoring systems may further comprise a sampling device, wherein said one or more microprocessors typically further comprise programming to control operation of the sampling device.

This invention and its application to analyte monitoring devices, for example, GlucoWatch biographer monitoring devices, are explained herein. Although the following description is exemplified with regard to glucose as an analyte, the invention is broadly applicable to analyses related to other analytes as will be apparent to one of ordinary skill in the art in view of the teachings of the present specification.

3.1.0 Employing Curve-Fitting and Parameter Estimation Based on Predictive-Kinetics (PK) in the $1/k_2$-Related Methods of the Present Invention The above general methods and devices can, of course, be used with a wide variety of detection systems, target analytes, and/or sensing techniques. The determination of particularly suitable combinations is within the skill of the ordinarily skilled artisan when directed by the present disclosure. Although these methods are broadly applicable to measuring any chemical analyte and/or substance in a system, the invention is expressly exemplified for use in an iontophoretic sampling system that uses an electrochemical biosensor to quantify or qualify glucose or a glucose metabolite.

3.1.1 Processing Steps to Extract the Glucose Concentration Information from the Time Constants The general functioning of GlucoWatch biographer monitoring device, as an exemplary analyte monitoring device, has been described above in the Definitions Section 1.0.0-1.1.2.

A. Calculate the Averaged Baselines.

An average baseline for the analyte measurement method is determined. Averaged baselines can be calculated in a variety of ways. For example, the last two current readings of an anodic cycle can be used to estimate the baseline (e.g., by using the last two current readings to obtain an average reading which is used to represent the baseline). FIG. 1 shows a plot of a typical full measurement cycle of raw GlucoWatch biographer data. In this example, cathode cycle has the Blood Glucose (BG) information and anode cycle provides the sensor baseline information. Other methods of estimating baseline can be employed (e.g., see published U.S. Patent Application No. U.S. 20020026110 and PCT International Patent Application No. WO 01/88534).

B. Subtract the Averaged Anode Baselines from Cathode Cycle Measurements.

Figure 2:
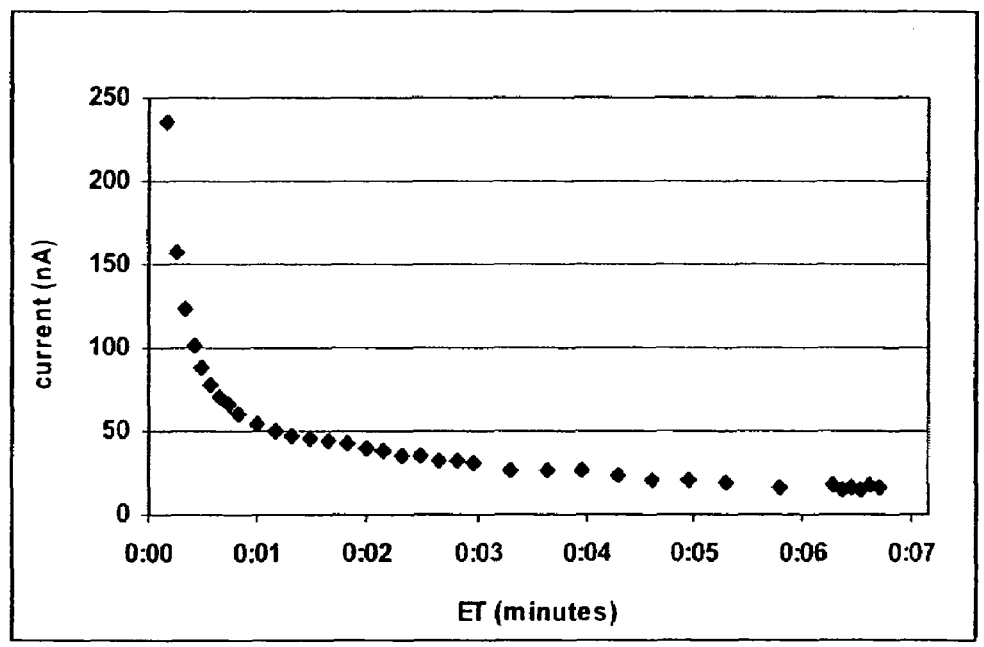
FIG. 2 shows a plot of current (nA) versus elapsed time (ET; minutes)) of previous baseline subtracted cathode cycle data.

After the data is collected, previous averaged baseline from anode cycle is subtracted from the cathode data (FIG. 2).

C. Take Integral of Baseline Subtracted Cathode Cycle with Respect to Time.

Next, the data is integrated over time to obtain the total charge at different measurement times. The charge and measured current values are shown in FIG. 3.

D. Use First 3 Minutes of Integrated Data (Transient Data) and Fit Model in Eq. (3A) Starting from 15$^{th}$ Second, Which Corresponds to the First Calculated Charge Value and Calculate $\{c_0, c_1, c_2, k_1, \text{ and } k_2\}$ Values for Each Cathode Cycle.

Figure 3:
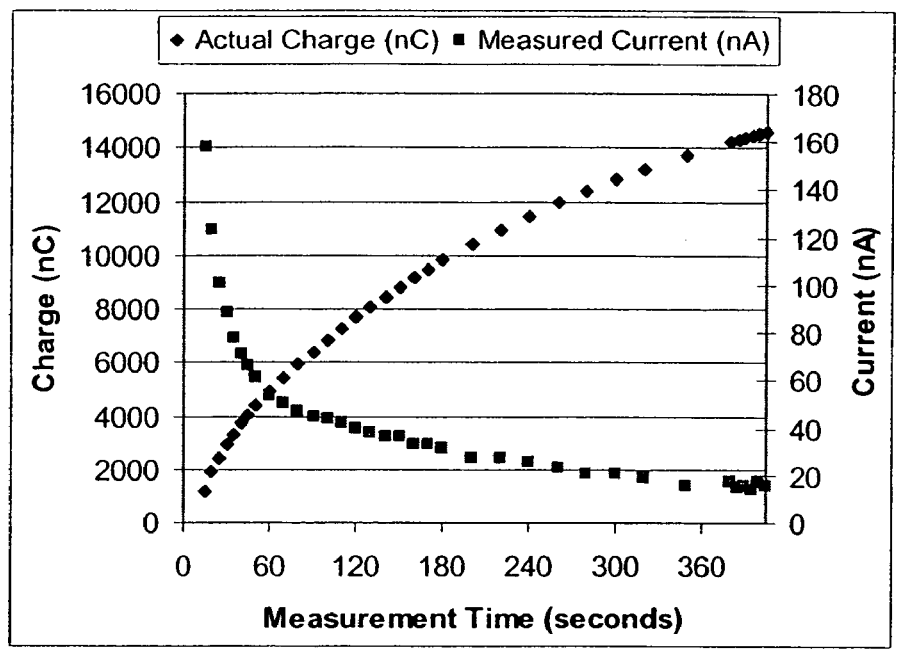
FIG. 3 shows a plot of charge (nC) (left vertical axis) (actual charge (nC) represented as diamonds) and current (nA) (right vertical axis) (measured current (nA) represented as squares) versus elapsed measurement time (ET; seconds)) of previous baseline subtracted cathode cycle data.

It is possible to mathematically model either of the curves in FIG. 3, for example, using a parallel first order model and optimize the model parameters by an appropriate minimization algorithm. Other mathematical models are presented below. In this study Levenberg-Marquart minimization algorithm is employed, however any other well-studied error minimization technique may also be used, for example, simplex optimization method. (See, e.g., error minimization methods described in "Numerical Recipes in C," Second Edition, Cambridge Univ. Press, 1992.)

Eq. 1 is a parallel first order model to express a previous averaged baseline subtracted cathode cycle current values (e.g., FIG. 3, squares). In Eq. 1, "i(t)" is current at elapsed time "t," "$c_0$" represents the final current value due to difference in actual baseline and measured baseline, "$c_1$" and "$c_2$" are pre-exponential terms that correspond to the electric current contribution at t=0 for the first and second reactions, respectively, "$k_1$" and "$k_2$" are rate constants for first and second reactions, respectively, and "t"

$$I(t) = c_o + c_1 e^{-k_1 t} + c_2 e^{-k_2 t} \qquad (\text{Eq. 1})$$

represents the elapsed time.

The fast reaction is approximated by "$c_1, k_1$" pair. The slow reaction is modeled by "$c_2, k_2$" pair. In this equation, $\{c_0, c_1 \text{ and } c_2\}$ have units of current (nA), and $\{k_1 \text{ and } k_2\}$ have units of time$^{-1}$ (1/sec.).

When the current model is integrated with respect to time, the charge model is obtained. Eq. 2 is the parallel first order model for charge curve (FIG. 3, diamonds).

$$Q(t) = c_o t + \frac{c_1}{k_1}(1 - e^{-k_1 t}) + \frac{c_2}{k_2}(1 - e^{-k_2 t}) \qquad (\text{Eq. 2})$$

In Eq. 2, "Q(t)" represents the charge at elapsed time "t," "$c_0$," "$c_1$," "$c_2$," "$k_1$," and "$k_2$" are as defined above. The estimated $\{c_0, c_1, c_2, k_1, \text{ and } k_2\}$ parameters from either current or charge data should be the same if there were no noise in the measurement. The current signal at the baseline, $c_0$, is determined and subtracted so that it is zero, thus making the term $c_o t \sim 0$. Further, empirical observations indicated that it was useful to add the additional term $S_0$ (a fitted parameter) into the equation for flexibility. By applying these changes to Eq. (2), Eq. (3A) is obtained.

$$Q(t) = S_o + \frac{c_1}{k_1}(1 - e^{-k_1 t}) + \frac{c_2}{k_2}(1 - e^{-k_2 t}) \qquad (\text{Eq. 3A})$$

Because the charge values are results of integration of current values over time and less sensitive to measurement noise, the charge curve (Eq. 3A) is preferable to estimate the cycle characteristics. However, the same analysis can be conducted by using the current values modeled by Eq. 1.

E. Obtain Glucose Concentration Information for Each Cycle from Time Constants $\{k_1 \text{ and } k_2\}$.

Following here are three exemplary methods to provide a correlation with analyte amount or concentration, for example, glucose concentration in a hydrogel of the GlucoWatch biographer. The second and third methods present similar information so only data for the second method is presented (a) $K_{min}$: Calculate reciprocal of slower time constant.

$$K_{min} = \frac{1}{\min(k_1, k_2)} = \frac{1}{k_2}$$

Figure 4:
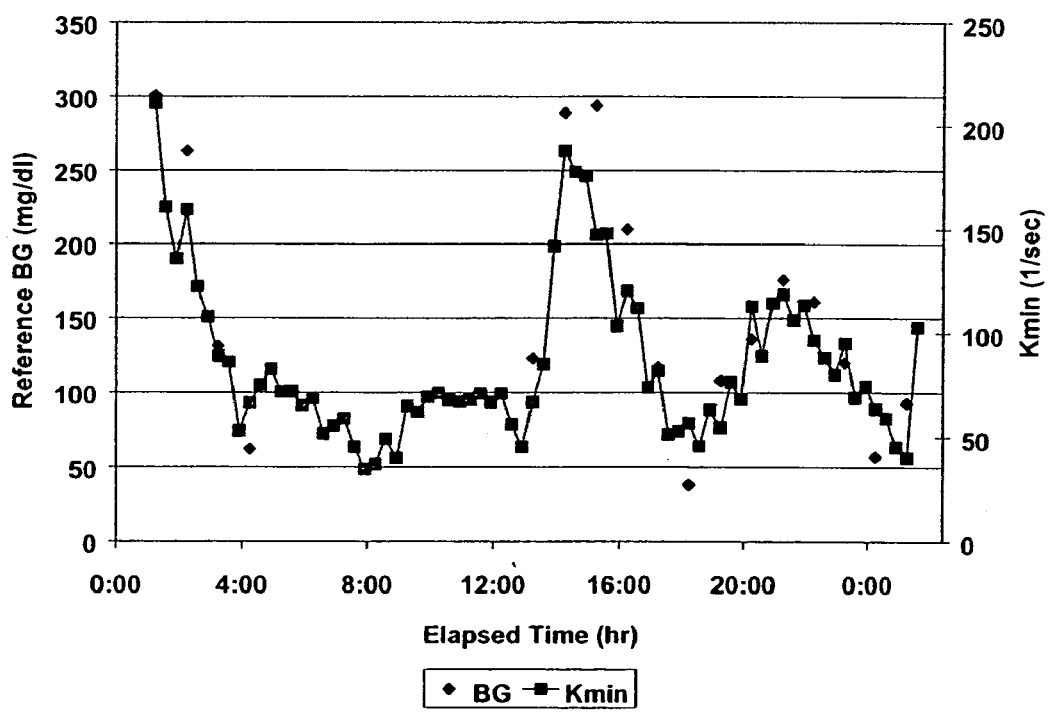
FIG. 4 shows a plot of Reference Blood Glucose (BG) in mg/dL (left vertical axis) (BG values represented as diamonds) and $K_{min}$ (right vertical axis) (this is a $1/k_2$ value; 1/seconds; represented as squares) versus Elapsed Time (hours)) of exemplary data obtained from one GlucoWatch biographer.

In FIG. 4 the data demonstrate that the $K_{min}$ ($1/k_2$) follows the reference BG pattern and it is capable of capturing all three BG peaks. The $K_{min}$ was not subject to signal decay.

(b) $K_{ratio}$: Calculate sum of ratios of time constants.

$$K_{ratio} = \frac{k_1}{k_2} + \frac{k_2}{k_1} \approx \frac{k_1}{k_2} \qquad (k_1 > k_2)$$

Figure 5:
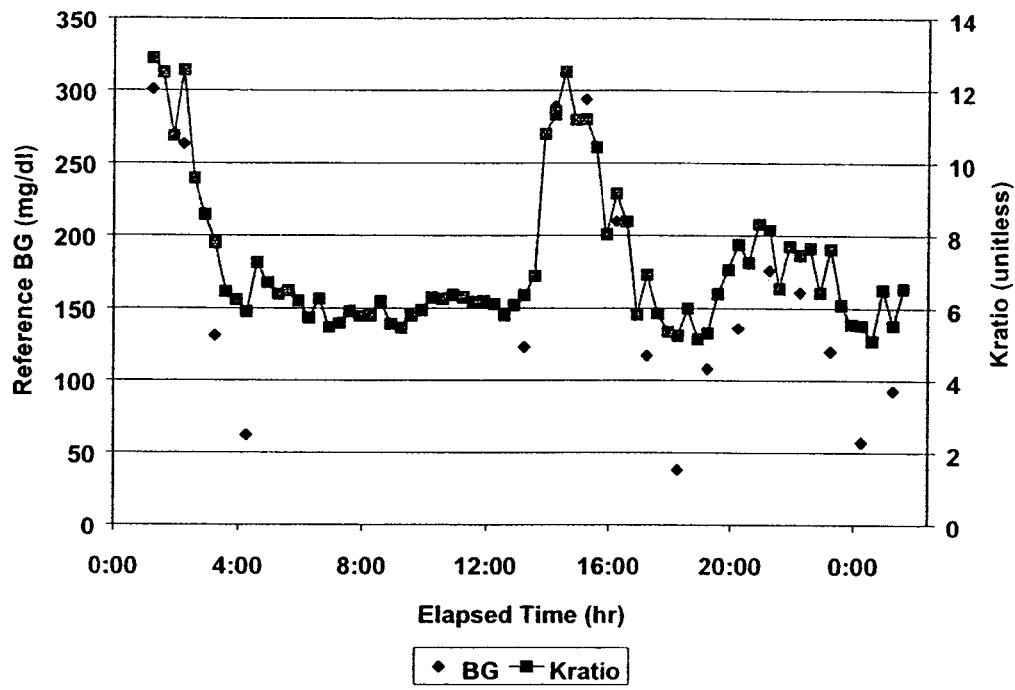
FIG. 5 shows a plot of Reference Blood Glucose (BG) in mg/dL (left vertical axis) (BG values represented as diamonds) and $K_{ratio}$ (right vertical axis) ($K_{ratio}=k_1/k_2+k_2/k_1$; unit less; $K_{ratio}$ represented as squares) versus Elapsed Time (hours) of exemplary data obtained from one GlucoWatch biographer.

The data presented in FIG. 5 show similar characteristics as FIG. 4. $K_{ratio}$ is also capable of capturing all three peaks and it is an alternative method to $K_{min}$.

c) $K_{max/min}$: Calculate the ratio of time constants of faster mechanism to slower one.

$$K_{max/min} = \frac{\max(k_1, k_2)}{\min(k_1, k_2)} = \frac{k_1}{k_2}$$

The $K_{max/min}$ can be correlated to analyte amount or concentration, for example, glucose concentration, as shown above for $K_{ratio}$.

Alternatively, a series of $1/k_2$ values can each be differentially weighted, using a weighting factor, wherein the sum of the weighting factors equals 1 (i.e., 100%), for example, as follows:

$$\sum_{i=0}^{n} w_i \left(\frac{1}{k_2}\right)_i = w_1 \left(\frac{1}{k_2}\right)_1 + w_2 \left(\frac{1}{k_2}\right)_2 + w_3 \left(\frac{1}{k_2}\right)_3 + \ldots$$

where the sum of $w_1+w_2+w_3+w_n=1.0$

3.1.2 Obtaining Signal Decay Information from the Coefficients

Empirically, it has been observed that the signal obtained from analyte monitoring systems in contact with biological fluids can decay over time. This is observed in implanted sensors (e.g., glucose sensors), as well as with other analyte monitoring systems (e.g., GlucoWatch biographer monitoring devices). Signal decay may result in relatively smaller signal at later elapsed times. The $c_2$ coefficient is related to this signal decay. Experiments performed in support of the present invention indicate it is also subject to signal decay and demonstrate a relationship with signal decay pattern. While not wishing to be bound by any particular theory or hypothesis, the following explanation is presented to encourage further understanding of the present invention. If $1/k_2$ is correlated to an analyte amount or concentration (e.g., glucose) and is not subject to signal decay (as illustrated by the data presented herein) and $Q_{(t)}$ is subject to signal decay, then $c_2$ is proportional to signal decay (refer to Eq. 2) assuming the "2" term dominates. Accordingly, $1/c_2$ can be used to compensate for signal decay.

Because $c_2$ is proportional to signal decay, reciprocals of that value may be used as a gain factor (G) for each cycle to compensate for the signal decay in estimated charge, for example, 7-minute integral or PK estimated charge. The $c_2$ value for a particular signal response curve may be employed. Alternatively, averaged (normalized) and/or smoothed $c_2$ values for a number of response curves may be employed. Methods of obtaining normalized and/or smoothed values, based on a series of values, are known in the art and can be applied to the present invention in view of the teachings herein. For example, a simple averaging of a series of $1/c_2$ values can be used, for example, averaging the $1/c_2$ values from t, t-1, t-2, to t-n, where n can be up to a large number. Alternatively, a series of $1/c_2$ values can each be differentially weighted, using a weighting factor, wherein the sum of the weighting factors equals 1 (i.e., 100%), for example, as follows:

$$\sum_{i=0}^{n} w_i \left(\frac{1}{c_2}\right)_i = w_1 \left(\frac{1}{c_2}\right)_1 + w_2 \left(\frac{1}{c_2}\right)_2 + w_3 \left(\frac{1}{c_2}\right)_3 + \ldots$$

where the sum of $w_1+w_2+w_3+w_n=1.0$.
An exemplary gain factor is as follows:

$$G = \frac{1}{c_2}$$

Figure 6:
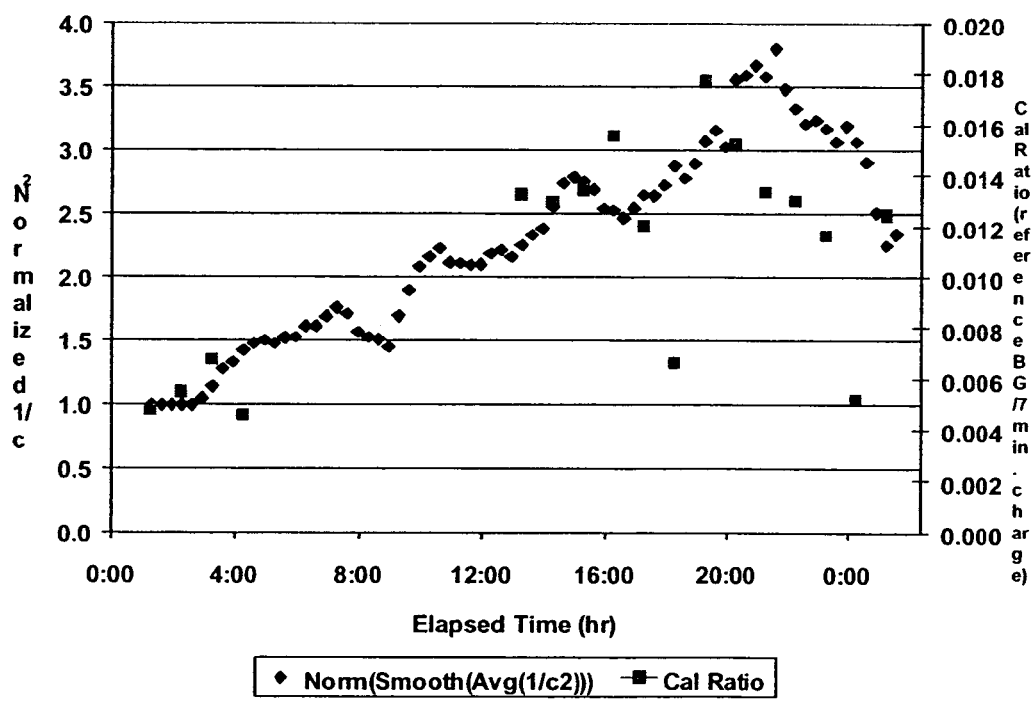
FIG. 6 shows a plot of normalized $1/c_2$ (left vertical axis) (Norm(Smooth(Avg($1/c_2$))) represented as diamonds) values and Calibration ratio (right vertical axis) (Reference Blood Glucose value/seven minute charge at the same time point; represented as squares) versus elapsed time (hours).

The data presented in FIG. 6 are for $(1/c_2)$ versus elapsed time. In this figure, diamonds are normalized smoothed $(1/c_2)$ using the first point of smoothed $(1/c_2)$. Smoothed $(1/c_2)$ is calculated by using a five-point moving average. Since first four points of averaged $(1/c_2)$ were lost while smoothing the data, these points were replaced with "1" in the normalized version. This substitution does not affect the results because there was no signal decay observed in the first two hours of data collection.

In FIG. 6, normalized $(1/c_2)$ is compared with different calibration ratios (CalRatio). The CalRatio is each Reference Blood Glucose (BG) measurement divided by the 7-minute integral charge calculated for that time point. The CalRatio is the inverse of the sensitivity of the GlucoWatch biographer. Thus an increasing CalRatio includes is signal decay. If normalized $c_2$ has a correlation with signal decay, normalized $1/c_2$ should follow calibration ratios in time. It is seen that normalized $(1/c_2)$ follows calibration ratios in time with a time delay. This delay may be a result of the smoothing applied to raw $(1/c_2)$ values (the 5-point moving average may lead to 100-minute delay).

Figure 7:
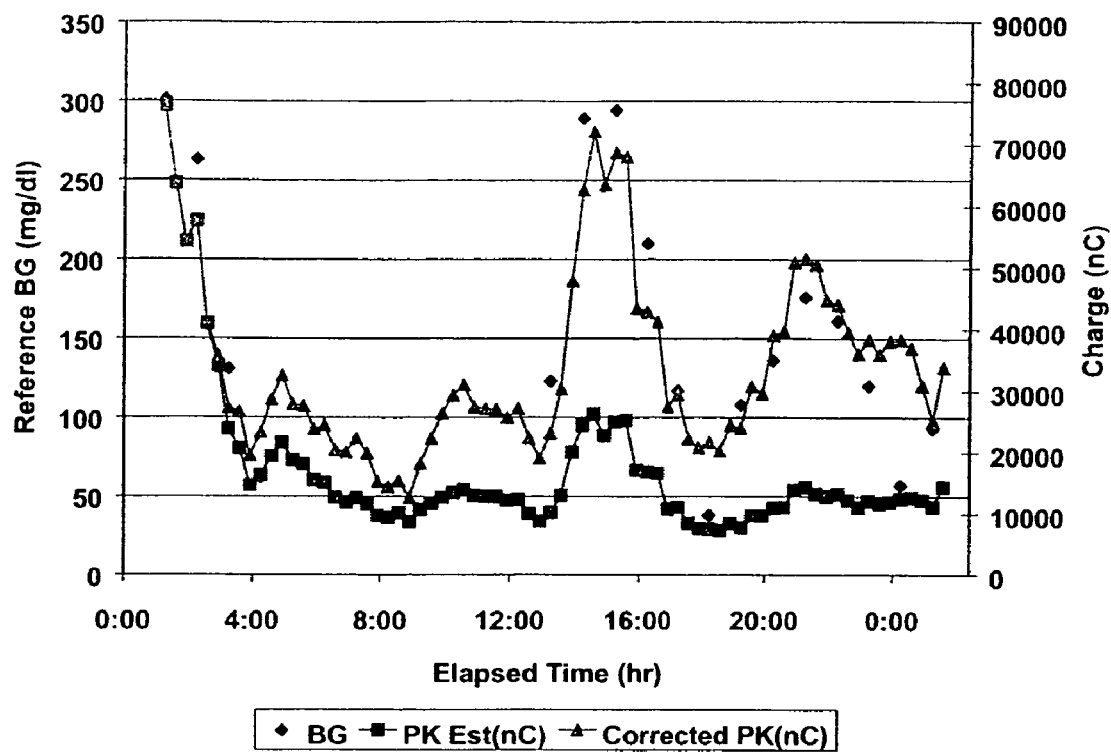
FIG. 7 shows a plot of Reference Blood Glucose (BG) values mg/dL (BG values represented as diamonds) and Charge in nC (corrected (signal decay compensated) PK estimated charge values (nC; represented as triangles) and uncorrected PK estimated charge values (nC; represented as squares)) versus Elapsed Time in hours (hr).

In FIG. 7, normalized smooth $(1/c_2)$ values were used to compensate for the signal decay in original PK charge estimates in an exemplary set of GlucoWatch biographer data. The uncorrected charge values (squares), which were subject to signal decay, were multiplied by corresponding $(1/c_2)$ value and corrected PK charge estimates (triangles), which has less signal decay, were calculated. Blood glucose is shown as closed diamonds. This correction did not change the performance of the PK charge estimates in the first 8 hours; however, this correction provided more effective performance in the second and the third eight hour periods of monitoring, and helped to capture the late peaks.

These data demonstrate that $c_2$ is proportional to signal decay and that reciprocals of the value may be used as a gain factor (G) for each cycle to compensate for the signal decay, for example, current or charge signal at time t may be multiplied by the gain factor to obtain a more precise current or charge signal in which signal decay has been compensated

3.1.3 Performance

The performance of the $1/k_2$ related methods of the present invention was evaluated for a glucose analyte using data sets obtained from GlucoWatch biographers. The functioning of GlucoWatch biographer monitoring devices is described herein (see, e.g., the Definitions Section 1.0.0-1.1.2).

Data obtained from GlucoWatch biographers was evaluated for signal decline over time. The data were processed in two ways, the $S_\infty$ PK application method and the seven minute integration method. Both of these methods showed that charge signal estimates exhibited similar signal decline (Example 1). The results suggest that direct application of the $S_\infty$ PK method may not completely compensate for signal decay.

The $1/k_2$ effect (i.e., one aspect of the present invention) appears when the first 3-minute data of charge (nC) signals calculated from the previous-background-subtracted current signals are fitted to the PK bi-exponential model given by, for example, Eq. (3A). Then, typically, the inverse of $k_2$, $1/k_2$, where $k_2$ is the smaller of apparent decay rates obtained from the fitting, tracks reference BG very well. In other words, $1/k_2$ is proportional to the glucose concentration in the hydrogel. Though not being bound by any particular theory or hypothesis, one hypothesis that may help facilitate understanding of the present invention is that higher glucose concentration leads to a slowdown of the slowest chemical process in the hydrogel, and this is reflected in the corresponding time constant calculated by the nonlinear fitting. Moreover, the $1/k_2$ signal as a function of the elapsed time exhibited very little signal decay. Exemplary data showing the $1/k_2$ effect are presented in Example 2.

In order to demonstrate the advantages of the methods of the present invention (i.e., the $1/k_2$ method for estimation of analyte amount or concentration, and the use of a gain factor to correct for signal decay) the following experiments were performed. Analysis of both $K_{min}$ (relative to Eq. 3A this corresponds to $1/k_2$) and $K_{ratio}$ (relative to Eq. 3A this corresponds to $\{k_1/k_2+k_2/k_1\}$) were performed on a data set obtained from 119 GlucoWatch biographers. The calculation of the $\{c_0, c_1, c_2, k_1, \text{and } k_2\}$ values for each cathode cycle was described above and in Example 3. $K_{min}$ and $K_{ratio}$ analysis were calculated and paired with reference BG values.

The slope of the linear regression line of $K_{min}$ or $K_{ratio}$ versus blood glucose indicates the stability of the signal over time. A decaying signal will show a decrease in slope over time. The measurement time of the GlucoWatch biographer in this experiment was approximately 26 hours. This time was divided into three intervals of approximately eight hours each.

In Table 5 (Example 3), averaged correlation values for each method ($K_{min}$ and $K_{ratio}$) at different time intervals are presented. Although correlation values for the new application were slightly low, the low correlation of $K_{min}$ in the smaller segments might be due to the variations in the $k_2$ estimation and may be corrected by optimizing the prediction parameters. However, even these slight variations in $k_2$ estimation did not affect the overall performance of this application. The data presented in Table 5 indicate that $K_{min}$ and $K_{ratio}$ showed a good averaged correlation in the 25-hour run (ALL, in Table 3).

In Table 6 (Example 3), averaged slopes for each method at different time intervals are presented. The $K_{min}$ and $K_{ratio}$ showed consistent slope for all intervals indicating no signal decay. Further, overall $K_{min}$ had higher averaged slope, which means higher sensitivity.

In order to investigate whether $K_{min}$ and $K_{ratio}$ are subject to signal decay slope ratios between intervals were calculated to quantify the signal decay from one interval to another.

In Table 7 (Example 3), averaged slope ratios for each method at different time intervals are presented. Both $K_{min}$ and $K_{ratio}$ keep the signal level almost steady for whole run indicating that these parameters provided estimates of analyte concentration or amount that were largely independent of effects of signal decay.

$K_{min}$ ($1/k_2$) is proportional to the analyte concentration or amount (e.g., concentration of glucose in the hydrogel of the GlucoWatch biographer). The high correlation of $K_{min}$ ($1/k_2$) to reference BG with less signal decay makes it a valuable candidate as an input to an alternative algorithm that may increase the useable duration of future generation GlucoWatch biographer monitoring devices having shorter warm up time. Accordingly, $K_{min}$ and $K_{ratio}$ values themselves can be used as estimates of analyte amount or concentration or these values may be used as input parameters in more complicated algorithms (such as MOE) to provide analyte amounts or concentrations.

Further, the data discussed in Example 4 illustrated that the $1/k_2$ method provides an improvement relative to the $S_\infty$ PK method and the standard 7-minute integration method. The $1/k_2$ method gave higher sensitivity, less signal decay, and higher overall correlation.

While analyzing data obtained from experiments performed in support of the present invention, (e.g., the $1/k_2$ effect), a related observation about the PK parameters $S_2$ and $k_2$ (Eq. (3a) and Eq. (3b)) was made. Multiplying coefficients $S_2$ and $k_2$ (where both quantities were obtained from fitting PK Eq (3A) to the first 3 minutes data of charge signal) led to an estimation of the coefficient $c_2$ in Eq. (2), $c_2=S_2k_2$. Coefficient $S_1$ (or, equivalently, $c_1/k_1$) was about an order of magnitude smaller than $S_2$, so that the latter provided a good approximation of the total PK charge signal $S_\infty$ (Eq. (4)). Because (as shown in the preceding section), due to the $1/k_2$ effect, $1/k_1$ includes all the relevant information about BG, and because the $S_\infty$ PK signal $S_\infty$ exhibits a significant signal decay, then equation $$S_\infty \approx \frac{c_2}{k_2} \qquad \text{(Eq. 5)}$$

indicates that all the relevant information about signal decay is included in the time dependence of $c_2$. Moreover, $c_2$ should be independent of BG. In this case, the quantity $$G = \frac{1}{c_2} \qquad \text{(Eq. 6)}$$

can be considered as a gain factor. It is useful for compensation of the signal decay in charge signal estimations obtained not only within the framework of $S_\infty$ PK method, but also within the 7-minute integration method Example 5 shows data relating to compensation for signal decay using the Gain Factor. In Example 5, charge signal was calculated using the 7-minute fixed-point method (plotted in FIG. 16 panel (a)). The charge signal was corrected for signal decay by multiplying it by the normalized and smoothed gain factor G. The resulting signal was plotted in FIG. 17 panel (b) together with the reference BG data. The data demonstrate that the described procedure of signal decay compensation (correcting the 7-minute charge signal using the gain factor) works very well.

Direct application of the $1/k_2$ effect as a method to track analyte concentration or amount (e.g., glucose levels in a subject being monitored) provides good results. Moreover, the $1/k_2$ effect can be used as a basis to develop various new methods to compensate sensor signal decay. The $1/k_2$-based methods described herein gave higher sensitivity, less signal decay, and higher overall correlation with the analyte concentration or amount (e.g., reference BG).

As can be seen from the data described in the preceding section, close tracking of blood glucose by GlucoWatch biographers is observed. However, although the GlucoWatch biographer performance is quite adequate for general monitoring of blood glucose levels, improvements may be desirable for the making GlucoWatch biographer monitoring devices still more user-friendly, more efficient, more accurate, and better at detection and prediction of hypoglycemic events.

3.1.4 Improvements of the $1/k_2$-Related Methods of the Present Invention Relative to GlucoWatch Biographer Monitoring Devices Experiments performed in support of the present invention demonstrated that the discovered $1/k_2$ effect can be used to develop new signal processing methods and new superior algorithms as well as, devices employing such methods and/or algorithms, further the present invention comprises one or more microprocessors programmed to execute such methods and/or algorithms. In addition, such one or more microprocessors may also be programmed to control measurement cycles, sampling devices, sensing devices. The methods of the present invention provide significant improvements in analyte monitoring device (e.g., GlucoWatch biographer monitoring devices) performance and reliability.

Advantages of the present invention include, but are not limited to, the following advantages. As demonstrated herein, algorithms based on the $1/k_2$ effect can be used to compensate the signal decay in analyte monitoring devices. This in turn may allow extension of the usable monitoring time of the analyte monitoring device. Because $1/k_2$-based signal processing requires current signal data only for the first three minutes of the 7-minutes biosensing period, application of this method leads to a reduction of the glucose measurement lime (i.e., reduction of the lag time between glucose extraction and GlucoWatch biographer monitoring device reading). Also, many of the skips that appear as part of data integrity check are due to sensitivity of the GlucoWatch biographers to various types of noise in the current or charge signals and due to the low signal-to-noise ratio when the glucose signal is low, (i.e., in the hypoglycemic range). Development of more robust algorithms based on $1/k_2$ effect and on the error-compensating $S_\infty$ PK methods will lead to reduction of the number of skips and to an improvement of the signal-to-noise ratio. This results in an improvement of the overall GlucoWatch biographer monitoring device accuracy, particularly in the hypoglycemic range.

Because $1/k_2$-type signals may comprises some noise compared to the 7-minute-integration or $S_\infty$ PK charge signal, one aspect of the present invention includes signal smoothing methods that simultaneously preserve all the relevant information about blood glucose.

In another aspect, the present invention includes self-consistent data-integrity-check system (i.e., screens) that fit the $1/k_2$-based signal processing method. For example, a screen to check the convergence of the nonlinear fitting of the error minimization algorithm can be added (e.g., employing the Levenberg-Marquardt algorithm). Empirical data can be used to optimize screen parameters.

In another aspect of the present invention, the MOE signal-processing algorithm (used in the GlucoWatch biographer to convert raw signals into a glucose measurement) is redesigned to fit the $1/k_2$ method and retrained using new data. As described in U.S. Pat. Nos. 6,180,416, and 6,326,160, MOE uses input parameters to estimate analyte amount or concentration, for example, parameters such as, elapsed time, nC signals, CalRatios, and blood glucose at the time of calibration to estimate glucose amount or concentration. As an alternative (or in addition to previously described parameters), $1/k_2$ and/or $c_2$ (or $1/c_2$) may be added as parameters in MOE to obtain a better estimate of glucose amount or concentration. It is likely that modification of the MOE algorithm will include changing input parameters, adding more Experts and testing large number of new models.

Accordingly, algorithms based on the $1/k_2$ effect may be used to develop new signal processing methods and algorithms for monitoring of analyte amount or concentration in a subject. As shown above, algorithms based on the $1/k_2$ effect may be used to compensate for signal decline. This, in turn, leads to extension of the effective monitoring time of analyte monitoring devices, for example, GlucoWatch biographer monitoring devices. In the case of GlucoWatch biographer monitoring devices, monitoring time may be extended to 24 hours and more. Further, in the case of GlucoWatch biographer monitoring devices, because the $1/k_2$-based signal processing can use current signal data for the first three minutes of a seven minute biosensing period, application of the $1/k_2$ methods leads to a reduction of the analyte measurement time (that is, a reduction in the lag time between glucose extraction and a measurement value presented by GlucoWatch biographer monitoring devices). Finally, many of the skips that appear as a result of data integrity checks are due to the sensitivity of the GlucoWatch biographer to various type of noise in the current or charge signals (e.g., due to a low signal-to-noise ratio when glucose signal is low). Development of more robust algorithms based on the $1/k_2$ effect and on the conventional error-compensating PK methods will lead to a reduction of the number of skips and to an improvement of the signal-to-noise ratio. As a consequence, overall accuracy of GlucoWatch biographer monitoring device performance may be improved, for example, in the hypoglycemic range.

3.1.5 Other Applications and Models

The same analysis can be conducted with different combinations of data segments and models. Six possible models are listed below:

$$i(t) = c_o + c_1 e^{-k_1 t} + c_2 e^{-k_2 t} \quad \text{(Model 1)}$$

$$i(t) = c_o + c_2 e^{-k_2 t} \quad \text{(Model 2)}$$

$$Q(t) = S + \frac{c_1}{k_1}(1 - e^{-k_1 t}) + \frac{c_2}{k_2}(1 - e^{-k_2 t}) \quad \text{(Model 3)}$$

$$Q(t) = S + c_o t + \frac{c_1}{k_1}(1 - e^{-k_1 t}) + \frac{c_2}{k_2}(1 - e^{-k_2 t}) \quad \text{(Model 4)}$$

$$Q(t) = S + \frac{c_2}{k_2}(1 - e^{-k_2 t}) \quad \text{(Model 5)}$$

$$Q(t) = S + c_o t + \frac{c_2}{k_2}(1 - e^{-k_2 t}) \quad \text{(Model 6)}$$

Model 1 corresponds to Eq. (1). Model 3 corresponds to Eq. (3A), and Eq (3B). In Table 1, the baseline subtraction and data intervals to be used in error minimization calculations are set forth for each of the six models.

TABLE 1

| | | Application options | | | |
|---|---|---|---|---|---|
| Start Time | End Time | Baseline Subtraction | From Current | From Charge | Remarks |
| Ts1 | Tf1 | Yes | Model 1 | Model 3 | Fast and slow process |
| Ts1 | Tf1 | No | Model 1 | Model 4 | Fast and slow process |
| Ts2 | Tf2 | Yes | Model 2 | Model 5 | Only Slow Process |
| Ts2 | Tf2 | No | Model 2 | Model 6 | Only Slow Process |

Figure 18:
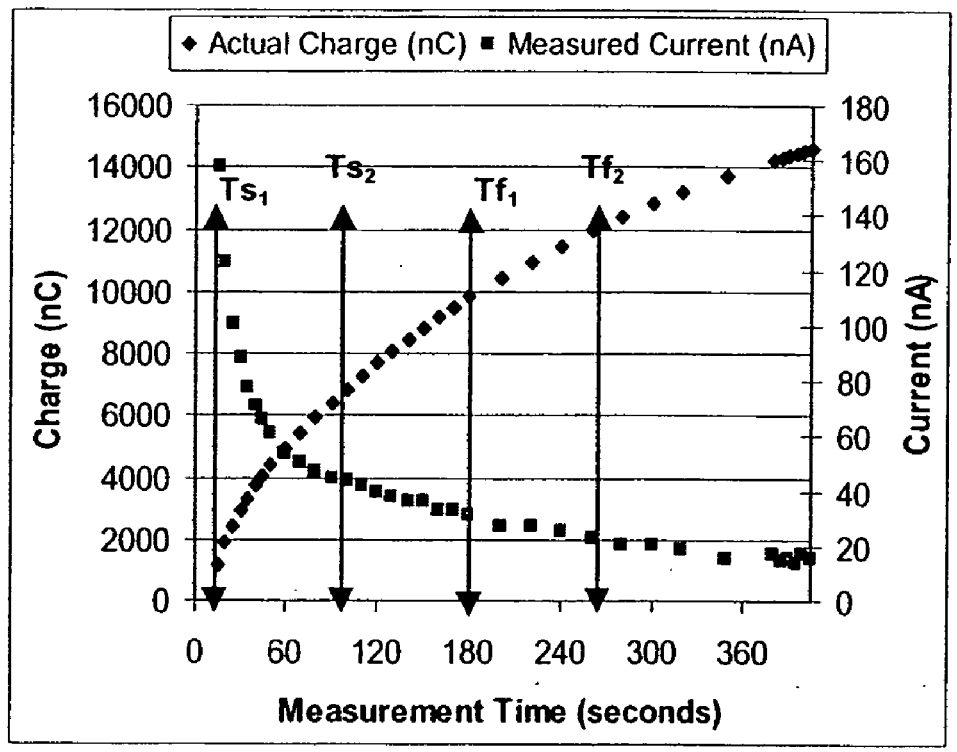
FIG. 18 provides exemplary data curves. Start times are presented as Ts1 and Ts2. End times are presented as Tf1 and Tf2. Start and end times are represented as vertical lines with arrowheads on either end. Actual charge (nC) is presented as a curve designated with diamonds and measured current (nA) is presented as a curve designated with squares. The left vertical axis is Charge (nC) and the right vertical axis is Current (nA) both plotted versus Measurement Time in seconds (horizontal axis).

The start time (Ts1, Ts2) and end time (Tf1 and Tf2) are given with reference to the exemplary data curves shown in FIG. 18. In FIG. 18, actual charge (nC) is presented as a curve designated with diamonds and measured current (nA) is presented as a curve designated with squares. Measurement time in seconds is provided along the bottom axis. For example, Model 1 (for current) or Model 3 (for charge) can be employed using Ts1 and Tf1 as start and end times defining the curve to which the model is fitted. Baseline subtraction is employed. Exponential and pre-exponential terms are obtained for both processes (i.e., $k_1$, $k_2$, $c_1$, and $c_2$) by fitting the model to the curve and employing an error minimization algorithm.

3.1.6 Advantages of the $1/k_2$-Related Methods of the Present Invention

The $1/k_2$ methods of the present invention yield higher analyte sensitivity and less signal decay. Further, the gain factor of the present invention provides a way to correct analyte signal for signal decay. The $1/k_2$ methods proposes to extract the analyte concentration information from the time constants ($k_1$ and/or $k_2$), whereas the previous $S_\infty$ PK application was assuming the time constants $\{k_1$ and $k_2\}$ to be independent of analyte concentration and employing only $\{S_0, S_1$ and $S_2\}$ to estimate a charge at time infinity ($S_\infty$). Further, experiments performed in support of the present invention demonstrate that the predicted coefficients in Eq.2 ($c_1$, and in particular $c_2$) were decreasing in time in a way correlated with signal decay.

In one aspect the present invention relates to a method of providing an analyte, for example, glucose, amount or concentration in a subject. In the method, a measured charge signal over time is obtained that comprises a measured charge signal response curve specifically related to the amount or concentration of the analyte extracted from the subject. The measured charge signal response curve comprises a kinetic region. The method uses (i) a mathematical model, for example, the model presented in Eq. (3A)

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively. Other models are described herein. The method also uses an error minimization method to iteratively estimate values of parameters $c_1$, $c_2$, $k_1$, and $k_2$ using the model and error minimization method to fit a predicted response curve to the kinetic region of the measured charge signal response curve. The error minimization method provides a calculated error based on differences between kinetic regions of the predicted and measured charge signal response curves. Also, the estimating is iteratively performed until the calculated error between the predicted and measured charge signal response curves is minimized or until no further statistically significant change is seen in the calculated error, at which time iterative estimation of the parameters is stopped. The iterative estimation and error minimization results in estimated values of the parameters. The method then correlates $1/k_2$ with a glucose amount or concentration to provide a measurement of the amount or concentration of the analyte in the subject. $K_{min}$, $K_{ratio}$, or $K_{max/min}$ may be similarly employed.

In one embodiment, $1/k_2$ is correlated with a glucose amount or concentration to provide a measurement of the amount or concentration of glucose by a method comprising applying a calibration value, for example, using the following equation:

$$[Glu]_t = \frac{[Glu]_{cal}}{(1/k_2)_{cal}}(1/k_2)_t$$

wherein $Glu_t$ is glucose concentration at time t, $Glu_{cal}$ is glucose concentration at a time of calibration that corresponds to an estimated $1/k_2$ at the time of calibration, and $(1/k_2)_t$ is the estimated $1/k_2$ at time t.

In one embodiment, the measured charge signal response curve was obtained by integration of a measured current signal response curve. Before the integration is performed a background value may be used to perform a background subtraction correction of the measured current signal response curve.

The obtaining step of the method may be performed two or more times to obtain a series of measurements. When a series of measurements is being used, after estimation of each predicted response curve for each measured charge signal response curve in the series of measurements an amount or concentration of the glucose may be determined based on each estimated parameter $1/k_2$.

In one embodiment of the invention, the obtaining step comprises extracting a sample comprising the analyte from the subject into a collection reservoir to obtain a concentration of the analyte in the reservoir. More than one collection reservoirs are typically employed. The collection reservoir may be in contact with a skin or mucosal surface of the subject. The analyte may be extracted across the skin or mucosal surface, using, for example, an Iontophoretic current applied to the skin or mucosal surface. Another exemplary method of extraction employs sonophoresis or a laser device. The collection reservoir may comprise an enzyme (e.g., glucose oxidase) that reacts with the extracted analyte to produce an electrochemically detectable signal. For example, when glucose oxidase is used, the electrochemically detectable signal is peroxide, and the signal is detected at a reactive surface of a biosensor electrode. In this embodiment the kinetic region of the measured charge signal response curve may corresponds to a measurement time period of 0 to about 180 seconds. The present invention also includes one or more microprocessors comprising programming to execute the above described $1/k_2$ methods. Further, the present invention includes analyte monitoring systems comprising such one or more microprocessors, wherein the one or more microprocessors are in operative combination with a sensing device. The analyte monitoring systems may also comprise a sampling device, also in operative combination. Some exemplary analyte monitoring systems are described herein, including, but not limited to, GlucoWatch biographer monitoring devices.

In another aspect, the present invention includes a method of correcting for signal decay of an electrochemical sensor used for the detection of an amount or concentration of analyte in a subject. The method includes obtaining a measured charge signal over time using the electrochemical sensor. The measured charge signal comprises a measured charge signal response curve specifically related to the amount or concentration of analyte extracted from the subject. The measured charge signal response curve comprises a kinetic region. The method uses (i) a mathematical model, for example, as presented in Eq. (3A)

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

wherein "Q" represents the charge, "t" represents the elapsed time, "$S_o$" is a fitted parameter, "$c_1$" and "$c_2$" are pre-exponential terms that correspond to the electric current contribution at t=0 for first and second reactions, respectively, "$k_1$" and "$k_2$" are rate constants for the first and second reactions, respectively, (other mathematical models are described herein) and (ii) an error minimization method, to iteratively estimate values of parameters $c_1$, $c_2$, $k_1$, and $k_2$ using the model and error minimization method to fit a predicted response curve to the kinetic region of the measured charge signal response curve. The error minimization method provides a calculated error based on differences between kinetic regions of the predicted and measured charge signal response curves. The estimating is iteratively performed until the calculated error between the predicted and measured charge signal response curves is minimized or until no further statistically significant change is seen in the calculated error, at which time iterative estimation of the parameters is stopped. The iterative estimation and error minimization results in estimated values of the parameters. A correction for signal decay of the electrochemical sensor is accomplished by multiplying the measured charge signal by a gain factor estimated based on $1/c_2$. The method may also employ $1/c_n$ terms, where $1/c_n$ is the pre-exponential factor associated with the $K_{min}$, reaction.

In this aspect of the present invention, the measured charge signal response curve may be obtained by integration of a measured current signal response curve. Before the integration is performed a background value may be used to perform a background subtraction correction of the measured current signal response curve. The obtaining step of the method may be performed two or more times to obtain a series of measurements. When a series of measurements is used, after estimation of each predicted response curve for each measured charge signal response curve in the series of measurements a gain factor may be determined based on each estimated parameter $1/c_2$ and each gain factor multiplied by the measured charge signal corresponding to the predicted response curve from which the gain factor was estimated. Such a series of measurements may comprise, for example, measured charge signal response curves at times t, t-1, t-2, etc. Two or more gain factors from the series of measurements may be normalized and/or smoothed to obtain a normalized and/or smoothed gain factor that is used to correct for signal decay of the electrochemical sensor by multiplying the measured charge signal at time t by the normalized and/or smoothed gain factor. For example, the series may comprises at least five measured charge signal response curves, and the normalized and/or smoothed gain factor may be calculated based on $(1/c_2)_t$, $(1/c_2)_{t-1}$, $(1/c_2)_{t-2}$, $(1/c_2)_{t-3}$, and $(1/c_2)_{t-4}$.

In one embodiment, the obtaining step comprises extracting a sample comprising the analyte, for example, glucose, from the subject into one or more collection reservoirs to obtain a concentration of the analyte in one or more reservoirs. The collection reservoirs may be contact with a skin or mucosal surface of the subject and the analyte may be extracted across the skin or mucosal surface using, for example, iontophoretic current applied to the skin or mucosal surface, sonophoresis, or a laser device. One or more collection reservoir may comprise an enzyme, for example, glucose oxidase, that reacts with the extracted analyte to produce an electrochemically detectable signal. For example, when glucose oxidase is used the electrochemically detectable signal is peroxide, and the signal may be detected at a reactive surface of the electrochemical sensor. In this embodiment, the kinetic region of the measured charge signal response curve may correspond to a measurement time period of 0 to about 180 seconds. The present invention also includes one or more microprocessors comprising programming to execute the above described methods.

Further, the present invention includes analyte monitoring systems comprising such one or more microprocessors, wherein the one or more microprocessors are in operative combination with a sensing device. The analyte monitoring systems may also comprise a sampling device, also in operative combination. Some exemplary analyte monitoring system are described herein, including, but not limited to, GlucoWatch biographer monitoring devices.

Accordingly, the methods of the present invention define novel ways for determining analyte amount or concentration, as well as ways to compensate for signal decay, when using an analyte monitoring device that employs the PK based methods described herein.

3.2.0 Conditional Screening.

The present invention provides methods to reduce the number of skips in an analyte monitoring device, for example, a GlucoWatch biographer monitoring device, during periods of perspiration. One method to achieve such a reduction in the number of skips is to combine two or more data integrity checks for any data point in question to make a composite data integrity check.

In one embodiment, a composite data integrity check takes the form of a classification or decision tree (i.e., a logical series of if/then statements). For example, if one or more data points related to a measurement value at a given time point (e.g., an electrochemical signal from a biosensor) demonstrate an aberrant behavior (e.g., shows non-monotonicity of the signal), then a second data integrity screen related to the time point is evaluated. If the second data integrity screen is within an acceptable range (wherein the acceptable range is typically empirically determined) then measurement value at that time point may be accepted even though it demonstrated some abnormality.

Typically, as many data screens that are available for the given time point are evaluated to insure that an acceptable number of the data screens are each within acceptable ranges.

For example, a measurement value at a given time point may be skipped (i.e., screened out) if a skin conductance value (i.e., sweat measurement) at the same time point falls outside of a predetermined range. In one embodiment of the present invention, rather than a single data screen, i.e., the skin conductance value, a series of data screens, comprising the composite data integrity check, may be used to determine whether the measurement value should be skipped. For example, if a measurement value is skipped because the skin conductance value is out of range, then further data integrity checks at the same time point may be examined. If all of the other further data integrity checks for that time point are acceptable then the measurement value may be accepted even though the skin conductance value was out of range. On the other hand, if one or more of the further data integrity checks are not acceptable (e.g., the values fall outside of acceptable ranges) then the measurement value is skipped. All of the further data integrity checks may be equally weighted so that, for example, when one of the further data integrity checks is aberrant the point is measurement is skipped. Alternatively, data screens that are empirically known to be more important than others to data integrity may be weighted more heavily such that more than one data integrity check may be aberrant, but a threshold is set for some number of data integrity checks having normal values (e.g., falling within an acceptable range) in order for the measurement value to be accepted rather than skipped.

This type of discriminant analysis allows the integrity of a measurement value to be qualified by more than one data integrity check before the decision is made to reject the measurement value. If one data integrity check indicates that there is an aberrant event, then further data integrity checks are examined. If these further data integrity checks do not indicate the presence of an artifact then the measurement value would not be eliminated (i.e., screened out), rather it would be accepted.

This aspect of the present invention provides a method to prevent a single aberrant reading from invalidating a measurement value when that single reading represents a limited problem. A data check that invalidates a measurement value can be qualified by further data checks, wherein if the further data checks indicate that no other important events are being adversely affected (i.e., their values falls within acceptable ranges) then the measurement value is not skipped. With reference to the above-described perspiration associated skips, a measurement value at a given time point is screened by a skin conductance value at that time point. If the skin conductance value is outside of an acceptable range, then further data integrity screens are examined. If the further data integrity screens are within acceptable ranges then the measurement value is accepted rather than rejected solely on the basis of the skin conductance (i.e., sweat) value.

In the case of the an analyte monitoring device that employs iontophoretic extraction of an analyte from a biological system followed by electrochemical detection of the analyte (e.g., a GlucoWatch biographer monitoring device), such further data integrity checks may include, but are not limited to, one or more of the following: sensor current, peak sensor current, background current, iontophoretic voltage, subject temperature, and/or analyte monitoring device operating temperature. Further exemplary screens are described, for example, in U.S. Pat. No. 6,233,471.

For other analyte monitoring devices the composite data integrity check may comprise different screens. For example, for subcutaneous sensors providing continuous analyte measurement further screens may include, but are not limited to, temperature of the subject, peak sensor signal, and trend analysis of the data.

With specific reference to reducing the number of skips related to sweat-related skips, the acceptable threshold for a perspiration screen (i.e., above which threshold an associated measurement value is screened out) can be modified in a number of ways including, but not limited to, the following. The following examples are described with reference to a GlucoWatch biographer monitoring device as an exemplary analyte monitoring device. One perspiration screen that has been employed looks at the maximum sweat value for a measurement half-cycle (i.e., iontophoretic extraction followed by sensing of the analyte with a sensing device in operative contact with a first cathode—a full measurement cycle would include a second iontophoretic extraction followed by sensing of the analyte at a second cathode). In one embodiment of the present invention, instead of using the maximum reading in any given half-cycle an aggregate sweat measurement for two or more half cycles is used. Such an aggregate value may, for example, be an average, a sum, a median, or other statistical parameter.

In another embodiment, instead of using absolute values of skin conductance as the sweat value, a change from one measurement cycle to the next measurement cycle (or one half-cycle to the next half-cycle) is used. While not wishing to be limited by any particular theory, the following is included to help further understanding of possible mechanisms. This change value (delta sweat) may be advantageous, for example, if the concentration of glucose in sweat is proportional to the derivative of the sweat rate (i.e., skin conductance over time). If glucose gathers in the sweat duct passively over time and then is secreted in a first episode of sweating, thereafter the concentration of glucose in sweat would be low and would not lead to an artifact.

In another embodiment related to iontophoretic extraction of analyte, a time-dependent sweat screen is optimized that takes advantage of the antiperspirant effects of iontophoresis (see, e.g., Tapper, R., J. Clin. Eng. 8(3):253-259 (1983); U.S. Pat. No. 4,325,367). In this embodiment, the sweat threshold would start with a tight threshold (e.g., 1 micro-Siemen) and then it would be loosened over time as the sweat secretion at the extraction site decreases (e.g., to about 2 micro-Siemen).

In yet another embodiment, the sweat threshold is based, for a current use period of an analyte monitoring device, on the sweat measured during a pre-calibration period (e.g., a period of time a subject is wearing a GlucoWatch biographer monitoring device before a calibration to blood glucose is performed).

Another exemplary situation, in addition to sweat monitoring (described above), wherein a composite data integrity check may be employed is as follows. If a signal from a sensor comprises data showing an aberrant trend then a composite data integrity check may be invoked. For example, in the case of a series of data points from an electrochemical sensor (wherein the data points are related to a measurement value of analyte amount or concentration) the data points related to a measurement value may demonstrate non-monotonicity. In a simple scenario if the electrochemical signal demonstrates non-monotonicity then the associated measurement value would be skipped. However, the present invention would further qualify such a data check using further data checks. For example, if the electrochemical signal demonstrates non-monotonicity, then if the effect of the non-monotonicity event on the overall signal is below a predetermined threshold value or within a predetermined range then the associated measurement value is accepted; however, if the effect of the non-monotonicity event on the overall signal exceeds a predetermined threshold value or falls outside of a predetermined range then the associated measurement value is skipped.

Figure 19:
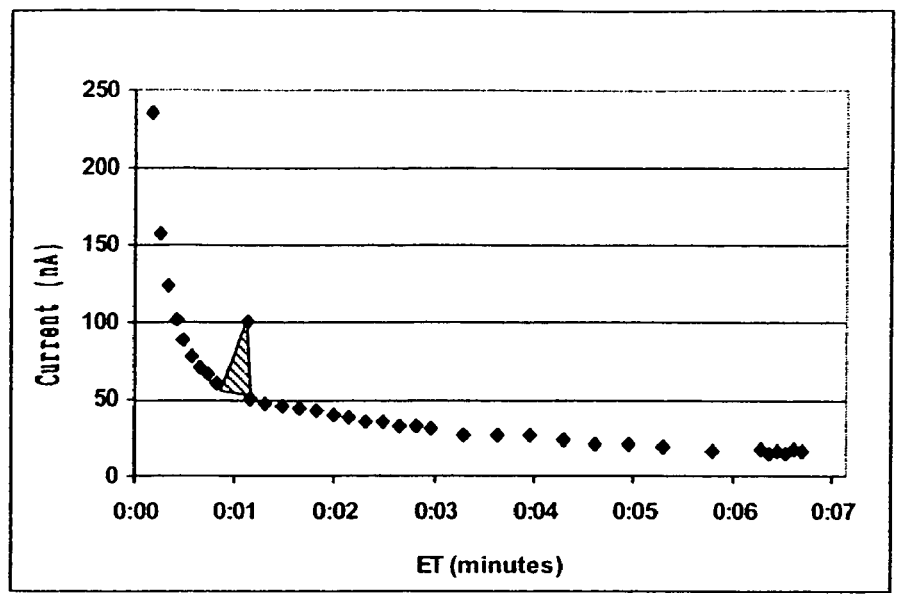
FIG. 19 illustrates a series of data points obtained from a sensor, wherein the data points are related to an analyte measurement value, and one of the data points (at elapsed time 0:01 minute) shows non-monotonicity with the trend of the other data points. A shaded area under this point shows this points contribution to overall signal. The vertical axis is Current (nA) and the horizontal axis is Elapsed Time (ET) in minutes.

FIG. 2 shows an example of an electrochemical signal demonstrating monotonicity. An example of an electrochemical signal showing non-monotonicity would be if the data point at Elapsed Time (ET) 0:01 of FIG. 2 fell outside of the trend of the other data points, for example, if that data point had a value of 100 nA instead of approximately 50 nA (illustrated in FIG. 19). In this situation, the percent that the particular data point contributes to the overall signal may be evaluated. If the percent contribution of that particular data point (e.g., by using the area under the curve as shown by shading in FIG. 19) is greater than a predetermined percentage of the overall signal (i.e., the area under the entire curve defined by the data points) then the associated measurement value is skipped. On the other hand, if the percent contribution of that particular data point (e.g., by using the area under the curve as shown by shading in FIG. 19) is less than a predetermined percentage of the overall signal (i.e., the area under the entire curve defined by the data points) then the associated measurement value is used. This method allows screens showing aberrant events to be qualified rather than just providing a simple accept/reject screen.

This method can be applied to any data screen to evaluate the overall effect of an aberrant event, which is associated with the screen, on (i) an associated signal (e.g., a background measurement) and/or (ii) a measurement value associated with the screen.

The present invention comprises methods of reducing the number of skipped measurement values provided by an analyte monitoring device by employing a composite data integrity check, one or more microprocessors comprising programming to control execution of such methods, and analyte monitoring systems comprising such one or more microprocessors. In one embodiment, this aspect of the invention comprises one or more microprocessors comprising programming to control providing a measurement value related to glucose amount or concentration in a subject, a skin conductance reading associated in time with the glucose measurement value, and one or more further data integrity screens associated with the glucose measurement value. The measurement value is accepted when either (i) the skin conductance reading and the one or more further data integrity screens fall within predetermined acceptable ranges or within predetermined threshold values or (ii) the skin conductance reading falls outside of predetermined acceptable range or beyond predetermined threshold value and the one or more further data integrity screens fall within predetermined acceptable ranges or with predetermined threshold values. The measurement value is skipped (i.e., screened out) when the skin conductance reading falls outside of predetermined acceptable range or beyond predetermined threshold value and one or more of the one or more further data integrity screens fall outside of predetermined acceptable ranges or beyond predetermined threshold values. Further data integrity screens include, but are not limited to peak sensor current and/or background current.

In another embodiment, this aspect of the present invention comprises one or more microprocessors comprising programming to control providing a measurement signal, comprising data points, related to glucose amount or concentration in a subject, wherein the data points typically have a monotonic trend. The data points are evaluated for one or more non-monotonic event, wherein (i) if the data points have an acceptable monotonic trend the measurement signal is accepted for further processing, or (ii) if the data points comprise one or more non-monotonic events then a percent contribution of the one or more non-monotonic events relative to total measurement signal is further evaluated. In situation (ii), if the percent contribution of the one or more non-monotonic events is less than a predetermined threshold value or falls within a predetermined range relative to total measurement signal, then the measurement signal is accepted for further processing. However, if the percent contribution of the one or more non-monotonic events is greater than a predetermined threshold value or falls outside a predetermined range relative to total measurement signal, then the measurement signal is not accepted for further processing and the measurement signal is skipped. Exemplary analyte-related measurement signals include, but are not limited to, current measurement or charge measurement.

3.3.0 Error-Limited Interpolation/Extrapolation Methods

Methods for obtaining missing measurement values based on interpolation and/or extrapolation have been previously described (see, e.g., PCT International Patent Application No. WO 03/000127). An examples of the uses of interpolated and/or extrapolated values includes, but is not limited to, when there is a skipped integral (i.e., charge measurement that is correlated to analyte amount or concentration) at calibration the skipped integral is provided by interpolation and/or extrapolation to prevent a failed calibration. This same technique is applied to post-calibration skips to recover measurement values that would have been removed by screens after calibration (exemplary screens are described, for example, in U.S. Pat. No. 6,233,471).

The present invention provides an improvement to the previously described interpolation and/or extrapolation methods. In the present invention, interpolated and/or extrapolated values may be submitted to data screens in order to identify the best candidate interpolated and/or extrapolated values. Additional screens are applied to interpolated and/or extrapolated values to prevent those with a higher than acceptable error from contributing to analyte readings (e.g., GlucoWatch biographer monitoring device glucose readings associated with a high error). Exemplary additional screening criteria include, but are not limited to the following. First, a signal comparison screen can be employed to insure adequate tracking of signal (e.g., a sensor consistency check as described below. Second, limitations on the types of skipped measurement values that can be provided by interpolation and/or extrapolation may be applied. For example, interpolation and/or extrapolation may be prohibited for cycles with background drift from calibration or delta temperature (i.e., change in temperature measurement over time) values outside of a predetermined, acceptable range or beyond a predetermined threshold value. Such changes in background measurement (e.g., background current for one or more electrochemical sensors) may indicate measurement cycles in which background current is highly variable. This type of aberrant behavior frequently interferes with interpolation/extrapolation calculations, leading to higher error for the interpolated and/or extrapolated values during these types of skips.

One exemplary additional screen that can be employed is a sensor consistency check, described herein with reference to an analyte monitoring device having a two sensor electrochemical detection system (e.g., a GlucoWatch biographer monitoring device). In this example a measurement cycle includes obtaining analyte related reading from both sensors. This additional screen is referred to as a sensor consistency check. For a given measurement cycle, the ratio $(I_t - I_{cal})/I_{cal} * 100$ is calculated for each of the two sensors, wherein $I_t$ is the integrated current (i.e., charge) for the sensor at time t, $I_{cal}$ is the integrated current at the same sensor at calibration. This number represents the percentage change in signal with respect to the calibration point. If the difference in percentage change between the two sensors is greater than or equal to a predetermined threshold value or falls outside of a predetermined range then a skip-error is triggered for the measurement value related to the signals from the two sensors For example, in the case of the GlucoWatch G2 biographer the percentage change between the sensors that is routinely acceptable is approximately 60% (experiments performed in support of the present invention indicate that this level can be increased, for example, up to about 200%), the threshold is set lower as a screen for whether it is appropriate to interpolate or extrapolate a missing measurement value for a given measurement cycle (e.g., a percentage change between sensors in this case may be set at approximately 30% for interpolation and extrapolation cycles) Typically this percentage change between the sensors signals includes the difference from calibration, for example:

$$\left| \frac{A - Acal}{Acal} - \frac{B - Bcal}{Bcal} \right| \times 100$$

wherein A is the signal from sensor A, Acal is the signal from sensor A at calibration, wherein B is the signal from sensor B, Bcal is the signal from sensor B at calibration and the absolute value times 100 provides the percentage change since calibration. In one embodiment, the percent change is checked between an actual sensor value (typically the sensor value preceding an interpolated/extrapolated value) and a sensor value provided by interpolation/extrapolation.

This sensor consistency check verifies consistent signal response between the sensors (e.g., two sensors). A large difference indicates noise in the signals. Typically this data integrity check is invoked only if no other error has been declared or if it is being used as a check for validity of interpolated or extrapolated measurement values.

A second exemplary data screen that can be used to qualify interpolated and/or extrapolated measurement values is a background drift check. This data screen is described with reference to a GlucoWatch biographer monitoring device. In GlucoWatch biographer monitoring devices, analyte is iontophoretically extracted in interstitial fluid samples. During detection of analyte each of two sensing electrodes alternately function as anode and cathode. Glucose, as an exemplary analyte, predominantly accumulates at the cathode (e.g., see FIG. 9). Accordingly, a background current for a particular sensor can be determined from the last two data points of signal from that sensor electrode when it acts as anode (see, e.g., FIG. 1). This baseline can be used to make a background correction of the signal generated at the cathode (see, e.g., the dotted line in FIG. 1). The anodal background is known to decline at a predetermined rate. If the anodal background signal does not decline at a predetermined rate, then a skip error is triggered for an associated measurement value (i.e., a measurement value determined a corresponding time point for the anodal background signal being evaluated).

In one embodiment, the change in anodal background is determined as follows. The background signal is corrected with respect to the temperature at calibration. This operation may be carried out as follows:

$$i_{bkgd,j,corr} = i_{bkgd,j} \exp^{k\left(\frac{1}{T_j} - \frac{1}{T_{cal}}\right)}$$

In the above equation, k is an empirically derived constant (in this case 6228 K, which is the same constant used for baseline temperature correction). $T_{cal}$ is the temperature of the baseline at calibration for the respective sensor (in Kelvin). The terms $i_{bkgd,j}$ and $T_j$ are, respectively, the background current value and temperature of the baseline of the j-th post-calibration cycle for the respective sensor (e.g., anode background). The term $i_{bkgd,j,corr}$ represents the temperature corrected background current at the j-th post-calibration measurement cycle Then a change in the anodal background is determined. This change in anodal background is compared to the expected change in the anodal background and the rate of change is determined to be within or outside an error band. The error band is typically empirically determined based on previously observed performance of the anodal sensor background. In one embodiment, if the following condition below is met, then a skip error is triggered:

$$\left| \frac{i_{bkgd,j,corr}}{i_{bkgd,CAL}} - \exp(k_{bkgd\_decay} * (ET_j - ET_{cal})) \right| \geq P_{error\_band}$$

In the above equation, $k_{bkgd\_decay}$ is a constant having, for example, a value of—0.026746 hr$^{-1}$. $ET_j$ is the actual elapsed time of the baseline measurement for the respective sensor for the j-th cycle. (For example, in the two sensor system of a GlucoWatch biographer monitoring device, if the post-calibration cycle ends at 4:15 ET (elapsed time), then the $ET_j$ of Sensor A and B are 4:05 and 3:55, respectively.) $ET_{cal}$ is the actual elapsed time of the baseline measurement for the respective sensor for the calibration cycle. (For example, in the two sensor system of a GlucoWatch biographer monitoring device, if the calibration cycle ends at 2:15 ET, then the $ET_{cal}$ of Sensor A and B are 2:05 and 1:55, respectively.) The error band parameter, in this case, is $P_{error\_band}$, equals 0.4 (dimensionless).

As a general statement of the above-data screen, if the baseline background signal does not decline at a predetermined rate, it is an indication that the sensitivity of the sensors is not declining in a manner consistent with the general population of points. This situation leads to points that are biased either high or low. Accordingly, if the background signal is not declining at the pre-determined rate then an interpolated/extrapolated value for this time period would not be calculated. If, on the other hand, if the background signal is declining within the error band of the pre-determined rate then an interpolated/extrapolated value for this time period is acceptable to calculate.

Another exemplary data screen that can be used to qualify interpolated and/or extrapolated measurement values is a change-in-temperature check. In this data screen, the dTemp/dtime (change in temperature/change in time) reading detects temperature changes that may affect the accuracy of the analyte (e.g., glucose) readings. If the dTemp/dtime reading is greater than a predetermined threshold or falls outside of a predetermined range, a skip error for the corresponding measurement time period is be triggered and, in the case of a missing measurement value, an interpolated/extrapolated measurement value would not be calculated. In the case of a GlucoWatch biographer monitoring device as an exemplary analyte monitoring system, if the dTemp/dtime reading is greater than or equal to 0.35° C./min, then a dTemp/dtime skip error is triggered for that measurement cycle. On the other hand, if the dTemp/dtime reading is less than a predetermined threshold or falls within of a predetermined range, an interpolated/extrapolated measurement value for the corresponding measurement cycle is calculated.

As a general statement of the principle of this data screen, large and/or rapid temperature changes alter the background signal and render corresponding measurement values invalid. Thus, the data screen is useful, for example, as an indication to skip interpolation/extrapolation.

The background drift and dTemp/dtime screens, described above, are particularly useful screens in analyte monitoring devices like GlucoWatch biographer monitoring devices because when the values of these screens fall beyond a predetermined threshold value or outside of a predetermined range, corresponding interpolated/extrapolated measurement values have shown poor performance. Experiments performed in support of the present invention suggest that interpolated/extrapolated measurement values should be screened (e.g., by single screens, or combinations of screens) in order to insure usability and appropriateness of employing such measurement values. Measurement values associated with these two specific skip conditions (i.e., background drift and dTemp/dtime) may be poor candidates for interpolation and extrapolation because these conditions are not generally isolated to a single measurement half-cycle (as a non-monotonicity event typically is), so they can affect the adjacent cycles which are used for the interpolation and extrapolation calculations.

Accordingly, when a measurement value for a measurement cycle is to be provided by interpolation/extrapolation, if a dTemp/dtime or background drift error condition is observed, interpolation/extrapolation is not performed. On the other hand, when a measurement value for a measurement cycle is to be provided by interpolation/extrapolation, if no dTemp/dtime or background drift error condition is observed, interpolation/extrapolation is performed to supply the measurement value. Further screens may be applied as well to such interpolated and/or extrapolated measurement values. For example, in a two sensor system such as a GlucoWatch biographer monitoring device, another requirement for an interpolation or extrapolation is that the ratio between the two sensors used in the interpolation/extrapolation calculation must be calculated within a certain amount of time from the skipped cycle integral that is being calculated. Because the relationship between the signals from the two sensors can change over time, the use of a ratio that was last calculated a long time ago may contribute error to the calculation. This time frame can be empirically determined. For example, in a GlucoWatch biographer monitoring device typically after a pair of clean analyte measurements interpolation/extrapolation is performed for up to and including four measurement half-cycles after the pair of clean measurements.

The above-described screens are useful, for example, as exclusion criteria. For example, in a series of measurement values there is a missing measurement value. The measurement value may be provided by interpolation or extrapolation. First, the measurement cycle to which the missing value corresponds is examined. If (i) the background drift and the dTemp/dtime reading are less than predetermined thresholds or fall within of predetermined ranges and (ii) less than a predetermined amount of time has passed relative to a pair of clean measurements, then an interpolated/extrapolated measurement value for the corresponding measurement cycle may be calculated.

The present invention comprises methods of screening measurement values obtained by interpolation and/or extrapolation (or a determination if interpolation and/or extrapolation of a measurement value should be carried out), one or more microprocessors comprising programming to control execution of such methods, and analyte monitoring systems comprising such one or more microprocessors. In one embodiment, this aspect of the present invention comprises one or more microprocessors comprising programming to control qualifying whether an unusable analyte-related electrochemical current signal from a given measurement cycle should be replaced by interpolation or extrapolation by applying one or more of the following criteria: (i) if a sensor consistency check value for the measurement cycle falls within a predetermined acceptable range or within a predetermined threshold then the corresponding analyte-related signal may be replaced; (ii) if a change in background current for the measurement cycle falls within a predetermined acceptable range or within a predetermined threshold then the corresponding analyte-related signal may be replaced; (iii) if a change in temperature falls within a predetermined acceptable range or within a predetermined threshold then the corresponding analyte-related signal may be replaced; and (iv) any ratio between sensors that is used in the interpolation/extrapolation calculation must be calculated within a predetermined time period relative to the signals on which such ratio is based replacing, Then, if the unusable signal is to be replaced in the series of analyte-related signals (e.g., as described in PCT International Patent Application No WO 03/000127) the unusable analyte-related signal is estimated by either: (A) if one or more analyte-related signals previous to the unusable analyte-related signal and one or more analyte-related signals subsequent to the unusable analyte related signal are available, then interpolation is used to estimate the unusable, intervening analyte-related signal; or (B) if two or more analyte-related signals previous to the unusable analyte-related signal are available, then extrapolation is used to estimate the unusable, subsequent analyte-related signal. The series of analyte-related signals is typically obtained from an analyte monitoring device over time and each analyte-related signal is related to an amount or concentration of analyte (e.g., glucose) in a subject being monitored with the analyte monitoring device. The one or more microprocessors may be further programmed to control operation of a sensing device that provides analyte-related signal. Further, the one or more microprocessors may be further programmed to control operation of the sampling device that provides a sample comprising the analyte to the sensing device.

3.4.0 Alternative Integration Schemes

Baseline background subtraction methods (including, but not limited to temperature-corrected baseline subtraction) have been previously described (see, e.g., U.S. Pat. No. 6,233,471).

Figure 20A:
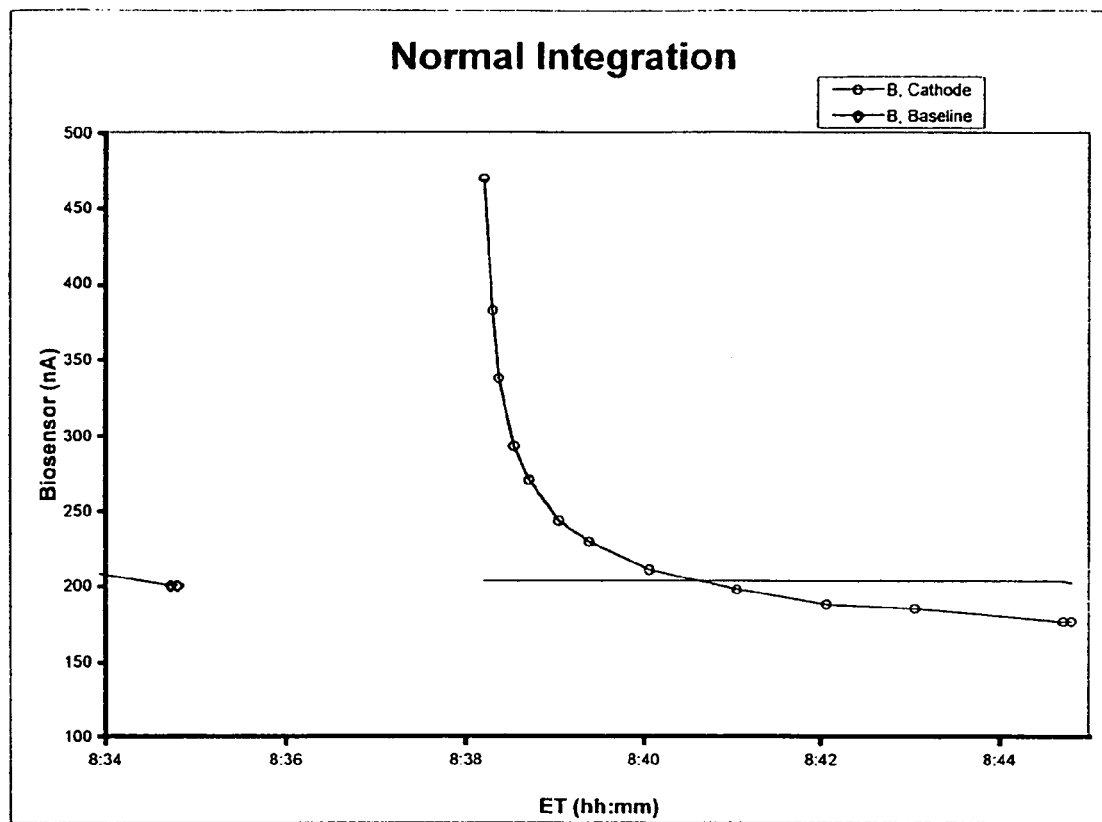
FIGS. 20A-20F present illustrations of a variety of integration methods.
Figure 20B:
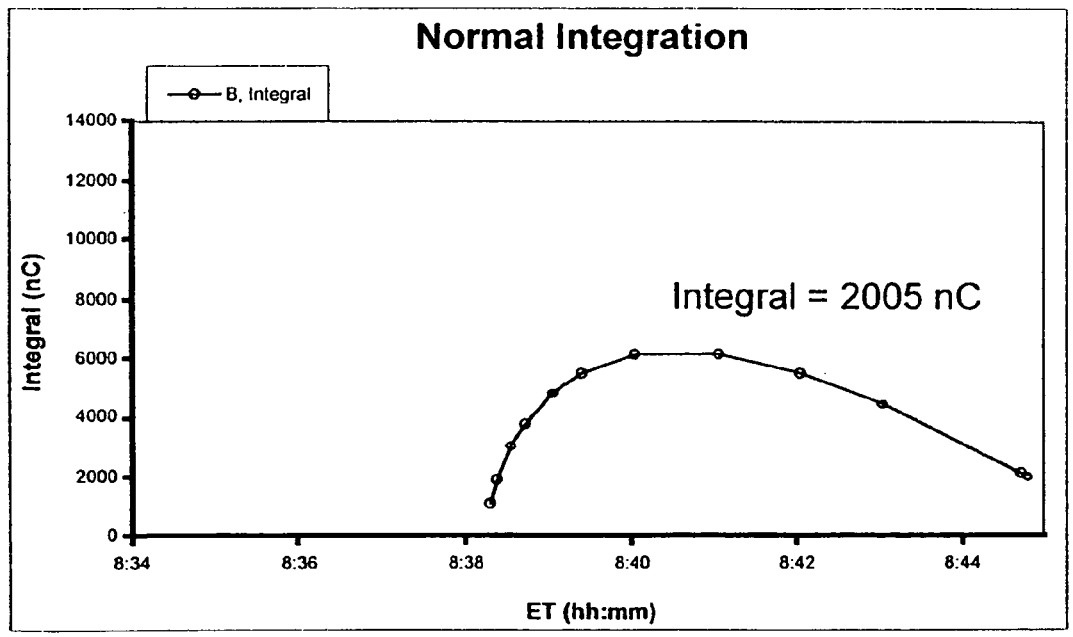

In some situations, for example when a previous anodal baseline for a given sensor is used for baseline subtraction of an analyte-related signal obtained from the same sensor when it is used as a cathode, previous baseline subtraction followed by integration can lead to negative charge measurements when the analyte-related signal drops below the previous anodal baseline. This situation can occur, for example, in the GlucoWatch biographer and GlucoWatch G2 biographer. In these situations, there is an over-subtraction, in which the cumulative integrated charge drops below its maximum value for a collection period. FIGS. 20A and 20B show this artifact, wherein after anodal background correction (in this case, temperature-corrected anodal background baseline) the concentration of analyte (e.g., glucose) declines over time. This does not make sense from a physical perspective, because the concentration of the glucose in the gel measured over time cannot drop below zero.

To eliminate this artifact derived from the previous-baseline subtraction method, alternative integration schemes that do not over-subtract for cycles where the previous baseline is larger than the biosensor signal can be used. These new integration schemes provide a larger, and potentially more relevant signal for use in calculation of analyte amount or concentration (e.g., glucose amount or concentration). The increased signal size will be realized particularly in the low signal range and may lead to an enhanced signal to noise ratio. This will provide improved performance for cycles with small analyte-related signal. The alternative integration schemes may also reduce the frequency of aborted calibrations due to small analyte-related signal.

Figure 20C:
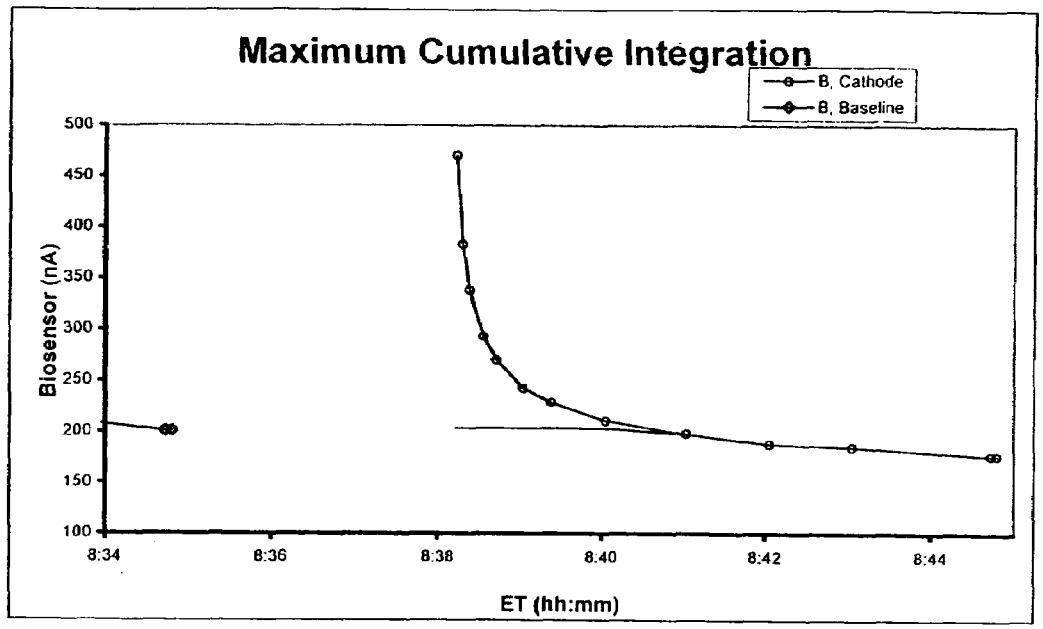
Figure 20D:
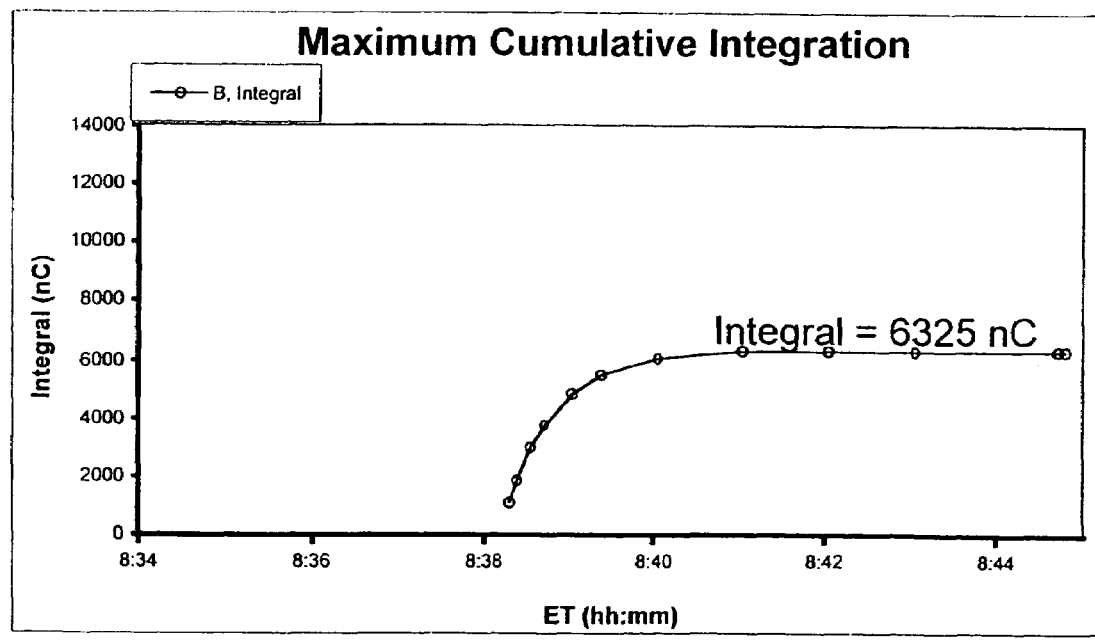

Two exemplary alternative integration schemes are described herein below with reference to the GlucoWatch G2 biographer. The signal is calculated by doing a trapezoidal integration of the area between the cathode current measurements and the temperature corrected background. The cumulative integral represents the total area for all of the trapezoidal areas between the current measurements. The cumulative integral can be plotted vs. time (FIG. 20B) similar to the cathode current measurements plotted vs. time (FIG. 20A). When there is over subtraction, the maximum cumulative integral is not the final integral reported by the trapezoidal integration. A first exemplary alternative integration scheme is a Maximum Cumulative Integration scheme (FIGS. 20C and 20D). In this scheme the integration is stopped when the maximum integral has been reached (thus the method is called the Maximum Cumulative Integration (FIG. 20D).

Figure 20E:
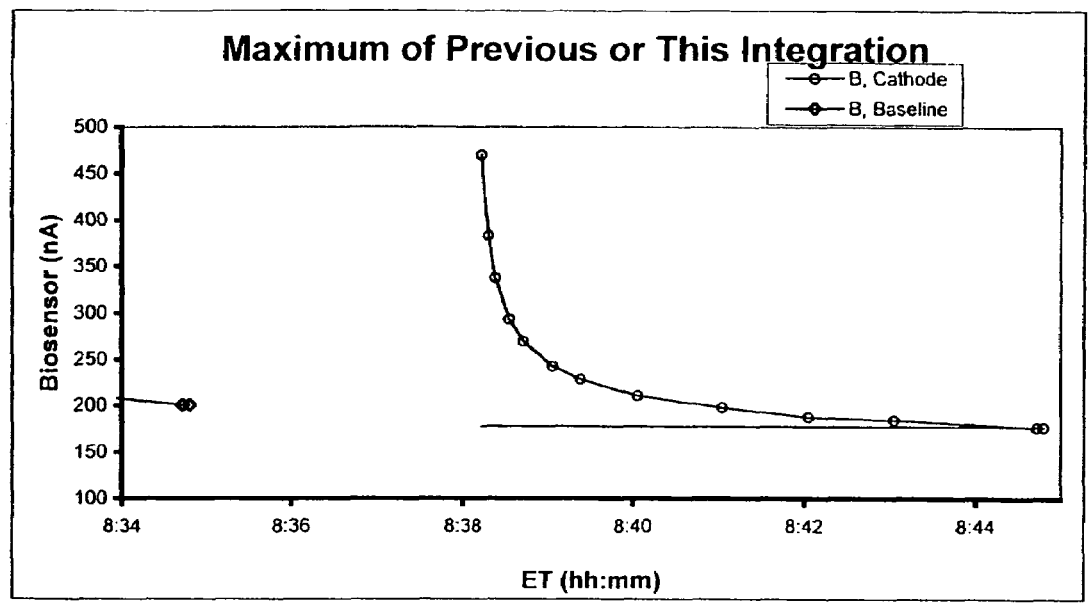
Figure 20F:
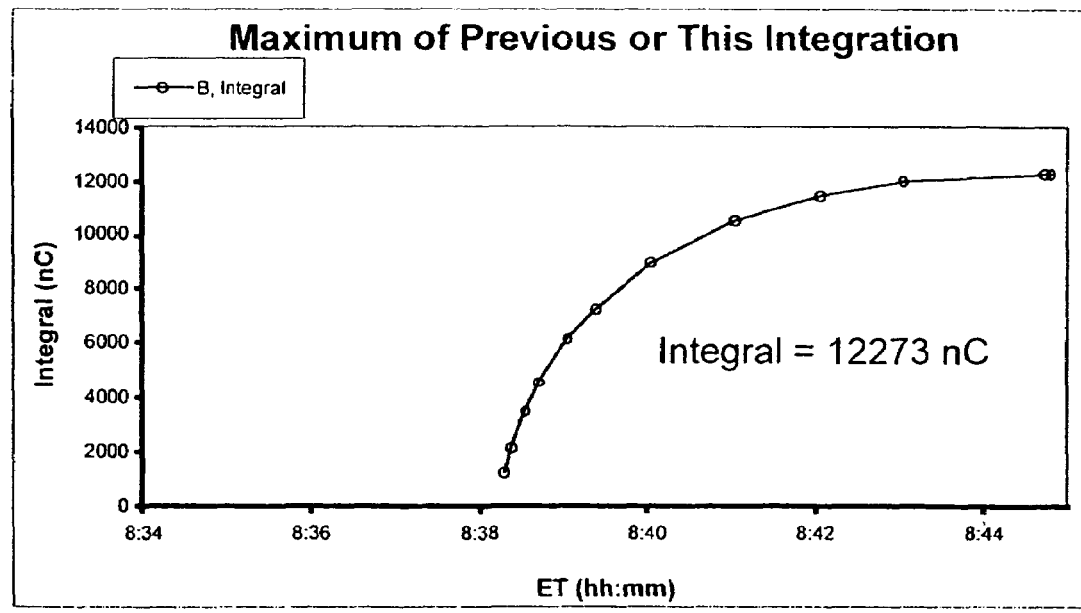

A second exemplary alternative integration scheme is a Maximum This or Previous Integration method. The name of the Maximum This or Previous Integration method is derived from the baseline subtraction method. For this method, if there is no over-subtraction, the standard previous anodal baseline subtraction (i.e., the last 2 measurements from the previous anode measurement cycle for this sensor is used to establish baseline) is used for baseline correction before integration. If there is over-subtraction, the last two cathodal measurements for the current cycle (i.e., "This" cycle) are used to establish the baseline for subtraction before integration (FIGS. 20E and 20F). If there is no over-subtraction, the "previous" baseline subtracted integral is larger. If there is over-subtraction, the "this" baseline subtracted integral is larger. Thus the method is called Maximum This or Previous Integration method.

The various integration methods can be used single or in combinations. Further, a decision tree can be used for selection of the appropriate integration strategy. For example, if there is no over-subtraction then use the previous anodal baseline for subtraction before integration. If there is over-subtraction, then use Maximum Cumulative Integration. Or in another embodiment, if there is no over-subtraction, then use the previous anodal baseline for subtraction before integration. If there is over-subtraction, then use the last two cathodal measurements for the current cycle to establish the baseline for subtraction before integration.

The present invention comprises methods of alternative integration, methods of selecting the integration mode, one or more microprocessors comprising programming to control execution of such methods, and analyte monitoring systems comprising such one or more microprocessors. In one embodiment, this aspect of the present invention comprises one or more microprocessors comprising programming to control selecting a current integration method for an analyte-related current signal, wherein the analyte-related current signal comprises data points. In one embodiment a two sensor system is used for detecting the analyte-related current signal and each of the two sensors are electrochemical sensors. Each sensor alternately acts as cathode and anode. A current signal, comprising data points, is detected in a half-measurement cycle from the anode and the cathode and the analyte-related current signal is obtained from the cathode. A background baseline is determined for a given sensor when acting as cathode, for example, from the last two data points of the current signal detected for the same sensor in a previous half-cycle when the sensor acted as an anode. This background baseline is subtracted from the analyte-related current signal and if over-subtraction of the analyte-related current signal occurs, one of the following integration methods is used to determine an analyte-related charge signal based on the analyte-related current signal: (i) stopping integration when the maximum integral is reached and using the maximum integral as the analyte-related charge signal or (ii) recalculating a background baseline based on the last two data points from the analyte-related current signal at the cathode, subtracting the recalculated background baseline from the analyte-related current signal, and integrating the background subtracted analyte-related current signal to obtain the analyte-related charge signal.

3.5.0 Improved Optimization Methods for Mixture of Experts (MOE) Parameters

The MOE algorithm for use in the determination of analyte amount or concentration in a subject has been previously described (see, e.g., U.S. Pat. Nos. 6,180,416 and 6,326,160. Briefly, the MOE method entails obtaining a raw signal from a biological system, wherein the raw signal is specifically related to analyte amount or concentration in the biological system. As the raw signals are obtained, a calibration step is performed to correlate the law signal with a measurement value indicative of the amount or concentration of analyte present in the biological system. These steps of detection and calibration are used to obtain a series of measurement values at selected time intervals. Once the series of measurement values is obtained, the MOE method provides for the determination of a measurement value using a MOE algorithm.

The raw signal can be obtained using any suitable sensing methodology. The sensing apparatus can employ any suitable sensing element to provide the raw signal including, but not limited to, physical, chemical, electrochemical, photochemical, spectrophotometric, polarimetric, calorimetric, radiometric, or like elements. In preferred embodiments of the invention, a biosensor is used which comprises an electrochemical sensing element.

The analyte can be any specific substance or component that one is desirous of detecting and/or measuring in a chemical, physical, enzymatic, or optical analysis. In one embodiment, a MOE algorithm is used to determine measurement values. The MOE algorithms rely on parameter sets in order to determine measurement values. The MOE algorithm is a generalized predictive technology for data analysis. This method uses a superposition of multiple linear regressions, along with a switching algorithm, to predict outcomes. Any number of input/output variables are possible. The unknown coefficients in this method are determined by a maximum posterior probability technique.

The method is typically implemented as follows. An experimental data set of input/output pairs is assembled that spans the expected ranges of all variables. These data are then used to train the MOE algorithm (i.e., used to determine the unknown coefficients). These coefficients are determined using, for example, the Expectation Maximization method (Dempster, A. P., N. M. Laird, and D. B. Rubin, J. Royal Statistical Society (Series B-Methodological) 39:(1), 1977). Once these coefficients are known, the MOE algorithm is easily applied to a new data set.

For the MOE algorithm, these parameters typically include, but are not limited to, the following: elapsed time since the monitor was applied to a subject; the active signal; the calibrated signal; the blood glucose value at the calibration point; the skin temperature; the skin conductivity; and the iontophoretic voltage. Changes in the values of any of these parameters can be expected to change the value of the calculated blood glucose value.

As described in U.S. Pat. Nos. 6,180,416, and 6,326,160, a MOE algorithm is used to provide analyte measurement values. The general MOE algorithm is represented by the following series of equations: where the individual experts have a linear form:

$$An = \sum_{i=1}^{n} An_i w_i \qquad \text{(MOE. 1)}$$

wherein (An) is an analyte of interest, n is the number of experts, $An_i$ is the analyte predicted by Expert i; and $w_i$ is a parameter, and the individual experts $An_i$ are further defined by the expression shown as Equation (MOE.2)

$$An_i = \sum_{j=1}^{m} a_{ij} P_j + z_i \qquad \text{(MOE. 2)}$$

wherein, $An_i$ is the analyte predicted by Expert i; $P_j$ is one of m parameters, m is typically less than 100; $a_{ij}$ are coefficients; and $z_i$ is a constant; and further where the weighting value, $w_i$, is defined by the formula shown as Equation (MOE.3).

$$w_i = \frac{e^{d_i}}{\left[\sum_{k=1}^{n} e^{d_k}\right]} \quad \text{(MOE. 3)}$$

where e refers to the exponential function and the $d_k$ (note that the $d_i$ in the numerator of Equation MOE.3 is one of the $d_k$) are a parameter set analogous to Equation MOE.2 that is used to determine the weights $w_i$. The $d_k$ are given by Equation MOE.4.

$$d_k = \sum_{j=1}^{M} \alpha_{jk} P_j + \omega_k \quad \text{(MOE. 4)}$$

where $a_{jk}$ is a coefficient, $P_j$ is one of m parameters, and where $\omega_k$ is a constant The MOE algorithm can be used, for example, to provide blood glucose values. In one aspect, this method is used in conjunction with an iontophoretic sampling device that provides frequent blood glucose measurements. In one embodiment the MOE algorithm is essentially as follows: where the individual experts have a linear form $$BG = w_1 BG_1 + w_2 BG_2 + w_3 BG_3 \quad \text{(MOE.5)}$$

wherein (BG) is blood glucose, there are three experts (n=3) and $BG_i$ is the analyte predicted by Expert i; $w_i$ is a parameter, and the individual Experts $BG_i$ are further defined by the expression shown as Equations MOE.6, MOE.7, and MOE.8

$$BG_1 = p_1(\text{time}) + q_1(\text{active}) + r_1(\text{signal}) + s_1(BG|cp) + t_1 \quad \text{(MOE.6)}$$

$$BG_2 = p_2(\text{time}) + q_2(\text{active}) + r_2(\text{signal}) + s_2(BG|cp) + t_2 \quad \text{(MOE.7)}$$

$$BG_3 = p_3(\text{time}) + q_3(\text{active}) + r_3(\text{signal}) + s_3(BG|cp) + t_3 \quad \text{(MOE.8)}$$

wherein, $BG_i$ is the analyte predicted by Expert i; parameters include, time (elapsed time since the sampling system was placed in operative contact with said biological system), active (active signal), signal (calibrated signal), and BG|cp (blood glucose value at a calibration point); $p_i$, $q_i$, $r_i$, and $s_i$ are coefficients; and $t_i$ is a constant; and further where the weighting value, $w_i$, is defined by the formulas shown as Equations MOE.9, MOE.10, and MOE.11

$$w_1 = \frac{e^{d_1}}{e^{d_1} + e^{d_2} + e^{d_3}} \quad \text{(MOE. 9)}$$

$$w_2 = \frac{e^{d_2}}{e^{d_1} + e^{d_2} + e^{d_3}} \quad \text{(MOE. 10)}$$

$$w_3 = \frac{e^{d_3}}{e^{d_1} + e^{d_2} + e^{d_3}} \quad \text{(MOE. 11)}$$

where e refers to the exponential function and $d_i$ is a parameter set (analogous to Equations MOE.6, MOE.7, and MOE.8) that are used to determine the weights $w_1$, given by Equations MOE.9, MOE.10, and MOE.11, and $$d_1 = \tau_1(\text{time}) + \beta_1(\text{active}) + \gamma_1(\text{signal}) + \delta_1(BG|cp) + \epsilon_1 \quad \text{(MOE. 12)}$$

$$d_2 = \tau_2(\text{time}) + \beta_2(\text{active}) + \gamma_2(\text{signal}) + \delta_2(BG|cp) + \epsilon_2 \quad \text{(MOE. 13)}$$

$$d_3 = \tau_3(\text{time}) + \beta_3(\text{active}) + \gamma_3(\text{signal}) + \delta_3(BG|cp) + \epsilon_3 \quad \text{(MOE. 14)}$$

where $\tau_i$, $\beta_i$, $\gamma_i$, and $\delta_i$ are coefficients, and where $\epsilon_i$ is a constant.

In another embodiment for the prediction of blood glucose values, the MOE algorithm is essentially as follows: where the individual experts have a linear form $$BG = w_1 BG_1 + w_2 BG_2 + w_3 BG_3 \quad \text{(MOE.15)}$$

wherein (BG) is blood glucose, there are three experts (n=3) and $BG_i$ is the analyte predicted by Expert i; $w_i$ is a parameter, and the individual Experts $BG_i$ are further defined by the expression shown as Equations MOE. 16, MOE. 17, and MOE. 18

$$BG_1 = p_1(\text{time}_c) + q_1(\text{active}) + r_1(\text{signal}) + s_1(BG|cp) + t_1 \quad \text{(MOE. 16)}$$

$$BG_2 = p_2(\text{time}_c) + q_2(\text{active}) + r_2(\text{signal}) + s_2(BG|cp) + t_2 \quad \text{(MOE. 17)}$$

$$BG_3 = p_3(\text{time}_c) + q_3(\text{active}) + r_3(\text{signal}) + s_3(BG|cp) + t_3 \quad \text{(MOE. 18)}$$

wherein, $BG_i$ is the analyte predicted by Expert i; parameters include, $\text{time}_c$ (elapsed time since calibration of said sampling system), active (active signal), signal (calibrated signal), and BG|cp (blood glucose value at a calibration point); $p_i$, $q_i$, $r_i$, and $S_i$ are coefficients; and $t_i$ is a constant; and further where the weighting value, $w_i$, is defined by the formulas shown as Equations MOE.19, MOE.20, and MOE.21

$$w_1 = \frac{e^{d_1}}{e^{d_1} + e^{d_2} + e^{d_3}} \quad \text{(MOE. 19)}$$

$$w_2 = \frac{e^{d_2}}{e^{d_1} + e^{d_2} + e^{d_3}} \quad \text{(MOE. 20)}$$

$$w_3 = \frac{e^{d_3}}{e^{d_1} + e^{d_2} + e^{d_3}} \quad \text{(MOE. 21)}$$

where e refers to the exponential function and $d_i$ is a parameter set (analogous to Equations MOE.6, MOE.7, and MOE.8) that are used to determine the weights $w_i$, given by Equations MOE.19, MOE.20, and MOE.21, and $$d_1 = \tau_1(\text{time}_c) + \beta_1(\text{active}) + \gamma_1(\text{signal}) + \delta_1(BG|cp) + \epsilon_1 \quad \text{(MOE.22)}$$

$$d_2 = \tau_2(\text{time}_c) + \beta_2(\text{active}) + \gamma_2(\text{signal}) + \delta_2(BG|cp) + \epsilon_2 \quad \text{(MOE.23)}$$

$$d_3 = \tau_3(\text{time}_c) + \beta_3(\text{active}) + \gamma_3(\text{signal}) + \delta_3(BG|cp) + \epsilon_3 \quad \text{(MOE.24)}$$

where $\tau_i$, $\beta_i$, $\gamma_i$ and $\delta_i$ are coefficients, and where $\epsilon_i$ is a constant.

Parameters can be substituted, and/or other parameters can be included in these calculations, for example, time parameters can be varied (e.g., as described above, elapsed time since the sampling system was placed in contact with a biological system, or elapsed time since the sampling system was calibrated) or multiple time parameters can be used in the same equation where these parameters are appropriately weighted. Further parameters include, but are not limited to, temperature, iontophoretic voltage, and skin conductivity. In addition, a calibration check can be used to insure an efficacious calibration.

MOE models consist of a set of experts (i.e., mathematical models), that model conditional probabilistic processes, and gates, which combine the probabilities of the experts. In order to determine the measurement values (e.g., analyte amount or concentration, for example, glucose concentration), the MOE algorithms rely on parameter sets that are determined using various optimization methods. For linear-regression models, typically, the unknown coefficients are fitted by minimizing the sum of squared errors between the predictions of the model and the targets (e.g., blood glucose values measured independently, i.e., not predicted by the model). In general, this is equivalent to maximizing the likelihood of the model given the data. This principle of maximum likelihood (ML) is used to fit parameters of MOE models, and the fitting process is called training of MOE. One problem with the maximum likelihood as an error estimation criterion is that it aims to minimize the difference between the targets and the predictions on the training data rather than on test data (e.g., data that has not been used for training but is used for testing the fit) or unseen data (e.g., a data set which is used for validation of the model but was not used for testing). If a sufficiently flexible model is trained using maximum likelihood principle, it may over-fit the training data and have poor universality (as seen, for example, by the model's generalization power on unseen data).

Following here are several methods useful for improving the performance of MOE algorithms by improving the parameters that are used as input into MOE.

3.5.1 Early Stopping and Cross-Validation

In one embodiment of this aspect of the present invention, one improved optimization method is to stop the MOE training process early, i.e., before the model coefficients have fully converged. One method for choosing when to stop training is cross-validation. In cross-validation the whole available training set (called a global training set) is divided into two subgroups, a local training set and a validation set. MOE models are trained on the local training set. For each MOE model the performance, as it is trained on the local training set, can be measured against a validation set that remains locally unseen (i.e., was not used in training). The MOE model performance measured against the validation set provides cross-validation. The training of the MOE model is stopped when the minimum error on the validation set occurs.

Figure 21:
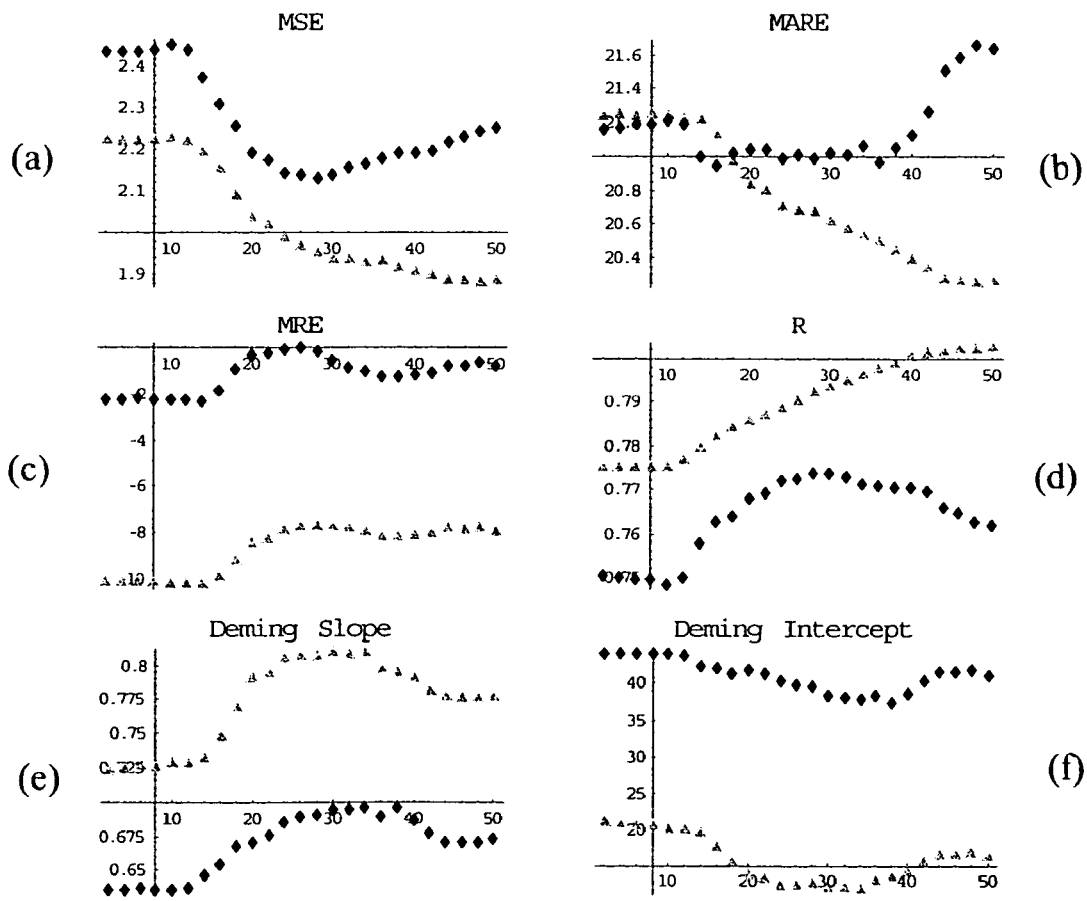
FIG. 21, panels (a) to (f) present an example of the evolution of various error estimators during the training of a MOE algorithm. In the figure, panels (a)-(f), triangles correspond to a local training data set and diamonds to a validation data set. The number of training iterations is represented on the horizontal axes. Panel (a) presents Mean square error (MSE), which is normalized by 1000. Panel (b) presents MARE (mean absolute relative error) and is given in percents. Panel (c) presents MRE (mean relative error) and is given in percents. Panel (d) presents R (the correlation coefficient). Panel (e) presents Deming Slope data. Panel (f) presents Deming Intercept data.

A typical example of the evolution of various error estimators (as well as of some other important performance parameters) during the training of the MOE for a GlucoWatch biographer monitoring device is shown in FIG. 21 (panels A-F). In the figure, panels A-F, triangles correspond to the local training data set, and diamonds to the validation data. The number of training iterations is represented on the horizontal axes Panel A presents Mean square error (MSE), which is normalized by 1000. Panel B presents MARE (mean absolute relative error) and is given in percents. Panel C presents MRE (mean relative error) and is given in percents. Panel D presepts R (the correlation coefficient). Panel E presents Deming Slope data. Panel F presents Deming Intercept data. In this particular example the training should be stopped after about 25 iterations because, as can be seen from FIG. 21, the universality of MOE begins to be lost at this point (a divergence between the performance of MOE on the validation data and the training data is observed).

Application of the early stopping and cross-validation method for that MOE training leads to universal models that have high generalization power on unseen data. In one embodiment, this aspect of the present invention comprises one or more computer programs that execute one or more algorithms to optimize parameters for use in a model that requires optimization of adjustable parameters, the one or more algorithms comprising dividing a data set into a training set and a validation set. The model is then trained to determine the adjustable parameters using the training set. The training is stopped before the model parameters have fully converged and the parameters are validated using the validation set, wherein the validated parameters are optimized parameters for use in the model. The validation step insures that the predictions of the model are accurate relative to the independent data of the validation set. One exemplary model that requires optimization of adjustable parameters is a MOE model. The present invention also includes software or firmware comprising such one or more algorithms. The present invention also includes hardware (e.g., computer systems) for use of such software comprising the algorithms of the present invention. In one embodiment the present invention relates to methods for optimizing parameters for use in a model that requires optimization of adjustable parameters.

3.5.2 Alternative Penalty Functions

For MOE-type models, typically, the model parameters are determined by minimizing the sum of squared errors between the predictions of the model and the targets. In this case, the sum of squared errors is called penalty function. However, depending on the statistical properties of the clinical data, use of an alternative penalty function can lead to a more robust model. Exemplary penalty functions includes, but are not limited to, MARE (mean absolute relative error; used singly or in combination with other functions), Lorenzian Error, Kovatchev's Low/High BG Risk Index (see, e.g., Kovatchev, B. P., et al., J. Theoretical Medicine, 3:1-10(2001); Kovatchev, B. P., et al., Methods Enzymol 321:396-410 (2000)), cost functions (see, e.g., Bellazzi, R., et al., IEEE Engineering in Medicine and Biology, January/February 2001, pages 54-64). Moreover, in order to develop MOE models that exhibit minimal bias (i.e. the minimal systematic error of an analyte monitoring device prediction, e.g., a prediction by a GlucoWatch biographer monitoring device), the penalty function can be extended to include the absolute difference between the actual Deming slope determined from the model and the desired Deming slope. The penalty function (the quantity to be minimized) in the MOE training process is thus MARE+W$|m-m_T|$, where m is the Deming slope predicted by the MOE model, $m_T$ is the target Deming slope (typically $m_T$=1), and W is a weighting factor that depends on the estimated value of MARE The alternative-penalty-functions optimization method is applicable not only to the MOE-type models, but to any model that requires optimization of adjustable parameters. Experiments performed in support of the present invention have demonstrated that MOE models developed using this type of penalty functions exhibit low bias and have good generalization power.

In one embodiment, this aspect of the present invention comprises one or more computer programs that execute one or more algorithms, wherein the one or more algorithms comprise optimizing the parameters based on multiple analyte readings that quantify two or more regions corresponding to various levels of accuracy for the prediction model used by the analyte monitoring device. One or more of the regions have an associated higher risk relative to one or more other regions (e.g., an analyte target regions). The optimization of the parameters is carried out until the error associated with the prediction model is minimized in the regions associated with higher risk and acceptable in the one or more other regions. An exemplary normal blood glucose region may be defined, for example, as about 70 to about 115 mg/dL. Relative to this region hypoglycemia may be defined as blood glucose of below about 70 mg/dL, and hyperglycemia as blood glucose above about 200 mg/dL. These values depend on the type of measurement device used to determine blood glucose and the ranges may be varied to better suit certain clinical outcomes (e.g., relative to a clinical outcome such as severe impairment or death). In this example, the higher risk regions would be the hypoglycemic region and/or the hyperglycemic region.

The present invention also includes software or firmware comprising such one or more algorithms. The present invention also includes hardware (e.g., computer systems) for use of such software or firmware comprising the algorithms of the present invention.

3.5.3 Optimization of the Distribution of Paired Points

Yet another optimization method for MOE-type models (and other models with adjustable parameters) is based on the optimization of a particular distribution of paired points. A paired point is constructed, for example, by representing the target analyte amount or concentration, for example, glucose concentration value, measured independently as the x coordinate, and the corresponding model prediction value as the paired y coordinate. The x-y plane is then divided into several regions corresponding to various levels of the analyte monitoring device accuracy and possibility of adverse clinical outcome. Device performance is often evaluated based on the number of paired points in these regions. For example, the Clarke error grid has been used to evaluate the performance of glucose monitoring devices (Cox, D. J., et al., Diabetes Care 8:529-536, 1985; Clarke, W. L., et al., Diabetes Care 10:622-628, 1987). In the analysis, paired data points from a reference method for measuring analyte amount or concentration, for example, glucose, and the analyte monitoring device under evaluation are placed in 5 categories (A to E), where A and B are considered clinically accurate or acceptable, and C to E show increasing error with the increasing possibility of adverse clinical outcomes. In one embodiment of the present invention, a mathematical function F is constructed that assigns a numerical value to each paired point (pp) in a particular category (region) For example, $F(pp) = -2$ if $pp \in A$ region,
$F(pp) = -1$ if $pp \in B$ region,
$F(pp) = 1$ if $pp \in C$ region,
$F(pp) = 2$ if $pp \in D$ region,
$F(pp) = 3$ if $pp \in E$ region These functions can be called risk functions for each of the paired points (The assignment of values is arbitrary in that, in this case, the most accurate and acceptable readings are given negative values and the regions showing increasing error are assigned positive, increasing values.)

Then, in the algorithm training process, the following quantity is minimized:

$$K = \frac{1}{N} \sum_{\{pp\}} F(pp)$$

wherein K is the total risk function, N is the total number of paired points and the summation runs over all paired points in the training set. This procedure leads to the optimization of the model parameters in such a way that the resulting algorithm maximizes the number of paired points in the clinically acceptable regions A and B, and minimizes the number of points in the regions C, D and E (these regions have been previously defined, see e.g., Cox, D. J., et al., Diabetes Care 8:529-536, 1985; Clarke, W. L., et al., Diabetes Care 10:622-628, 1987). Similar procedure can be used to maximize the percentage of paired points within a certain absolute or relative distance from the desired y-x line.

Application of the optimization methods described above has led to new MOE algorithms that exhibit improved accuracy (particularly for low analyte, e.g., glucose, values), less bias and very good universality.

In one embodiment of this aspect of the present invention, the optimizing comprises optimizing a distribution of paired points by, for example, constructing an x-y plane of paired points representing (i) a target analyte amount or concentration measured independently as the x coordinate and (ii) a corresponding model prediction of target analyte amount or concentration as a paired y coordinate. The model is employed by an analyte monitoring device typically for the estimation or prediction of analyte-related values. The x-y plane is divided into two or more regions corresponding to various levels of accuracy for the model prediction of the analyte monitoring device. Individual mathematical risk functions (F) are constructed that assign a numerical value to each paired point (pp) for a particular region. The individual risk functions are summed to provide a total risk function and the total risk function is minimized to result in optimized parameters for the model. One such exemplary model is a MOE model. An exemplary analyte is glucose. When the exemplary analyte is glucose, the two or more regions corresponding to various levels of accuracy for the prediction model may comprise a hypoglycemic region, a glucose target range, and a hyperglycemic region, and the one or more of the regions that have an associated higher risk relative to one or more other regions comprise the hypoglycemic region and the hyperglycemic region. The present invention also includes software or firmware comprising such one or more algorithms. The present invention also includes hardware (e.g., computer systems) for use of such software or firmware comprising the algorithms of the present invention.

4.0 Exemplary Monitoring Systems

Numerous analyte monitoring systems can employ the methods and microprocessors of the present invention. Typically, the monitoring system used to monitor the level of a selected analyte in a target system comprises a sampling device, which provides a sample comprising the analyte, and a sensing device, which detects the amount or concentration of the analyte or a signal associated with the analyte amount or concentration in the sample.

One exemplary monitoring system, GlucoWatch biographer monitoring device, is described herein for monitoring glucose levels in a biological system via iontophoretic, transdermal extraction of glucose from the biological system, particularly an animal subject, and then detection of signal corresponding to the amount or concentration of the extracted glucose. Analyte monitoring systems (including GlucoWatch biographer monitoring devices) and components thereof, have been previously described (see, e.g., U.S. Pat. Nos. 6,398,562, 6,393,318, 6,370,410, 6,341,232, 6,391,643, 6,309,351, 6,299,578, 6,298,254, 6,272,364, 6,233,471, 6,180,416, 6,144,869, 6,023,629, 5,989,409, 5,771,890, 6,356,776, 6,326,160, 6,284,126, 6,139,718, 5,954,685, 6,201,979, 6,141,573, 5,827,183, and 5,735,273; and PCT International Publication Nos. WO0218936; WO0217210; WO02215778; WO0215777; WO0188534; WO0188534; WO0064533; WO0047109; WO0024455; WO0018289; WO0015108; WO9958973; WO9958190; WO9958051; WO9958050; WO9842252; WO9724059; WO9710499; WO9710356; WO9702811; WO9600110; and WO9600109). GlucoWatch biographer monitoring devices include, but are not limited to, the GlucoWatch® (Cygnus Inc., Redwood City, Calif.) biographer and the GlucoWatch® G2™ (Cygnus Inc., Redwood City, Calif.) biographer. The GlucoWatch G2 biographer reduces warm-up time (from three to two hours), increases the number of readings per hour (up to six versus up to three), extends AutoSensor duration (from 12 to 13 hours), and provides predictive low-alert alarms. The GlucoWatch G2 biographer uses the same AutoSensor as the first-generation GlucoWatch biographer. The GlucoWatch biographers are described in detail herein.

Using a GlucoWatch biographer monitoring devices, transdermal extraction is carried out by applying an electrical current to a tissue surface at a collection site. Transdermal extraction is carried out by applying an electrical current or ultrasonic radiation to a tissue surface at a collection site. The electrical current is used to extract small amounts of glucose from the subject into a collection reservoir. The collection reservoir is in contact with a sensor element (biosensor) which provides for measurement of glucose concentration in the subject. As glucose is transdermally extracted into the collection reservoir, the analyte reacts with the glucose oxidase within the reservoir to produce hydrogen peroxide. The presence of hydrogen peroxide generates a current at the biosensor electrode that is directly proportional to the amount of hydrogen peroxide in the reservoir. This current provides a signal which can be detected and interpreted (e.g., employing the PK-based method described herein) by an associated system controller to provide a glucose concentration value or amount for display.

In the use of the sampling system, a collection reservoir is contacted with a tissue surface, for example, on the stratum corneum of a subject's skin. An electrical current is then applied to the tissue surface in order to extract glucose from the tissue into the collection reservoir. Extraction is carried out, for example, frequently over a selected period of time. The collection reservoir is analyzed, at least periodically and typically frequently, to measure glucose concentration therein. The measured value correlates with the subject's blood glucose level.

Figure 8:
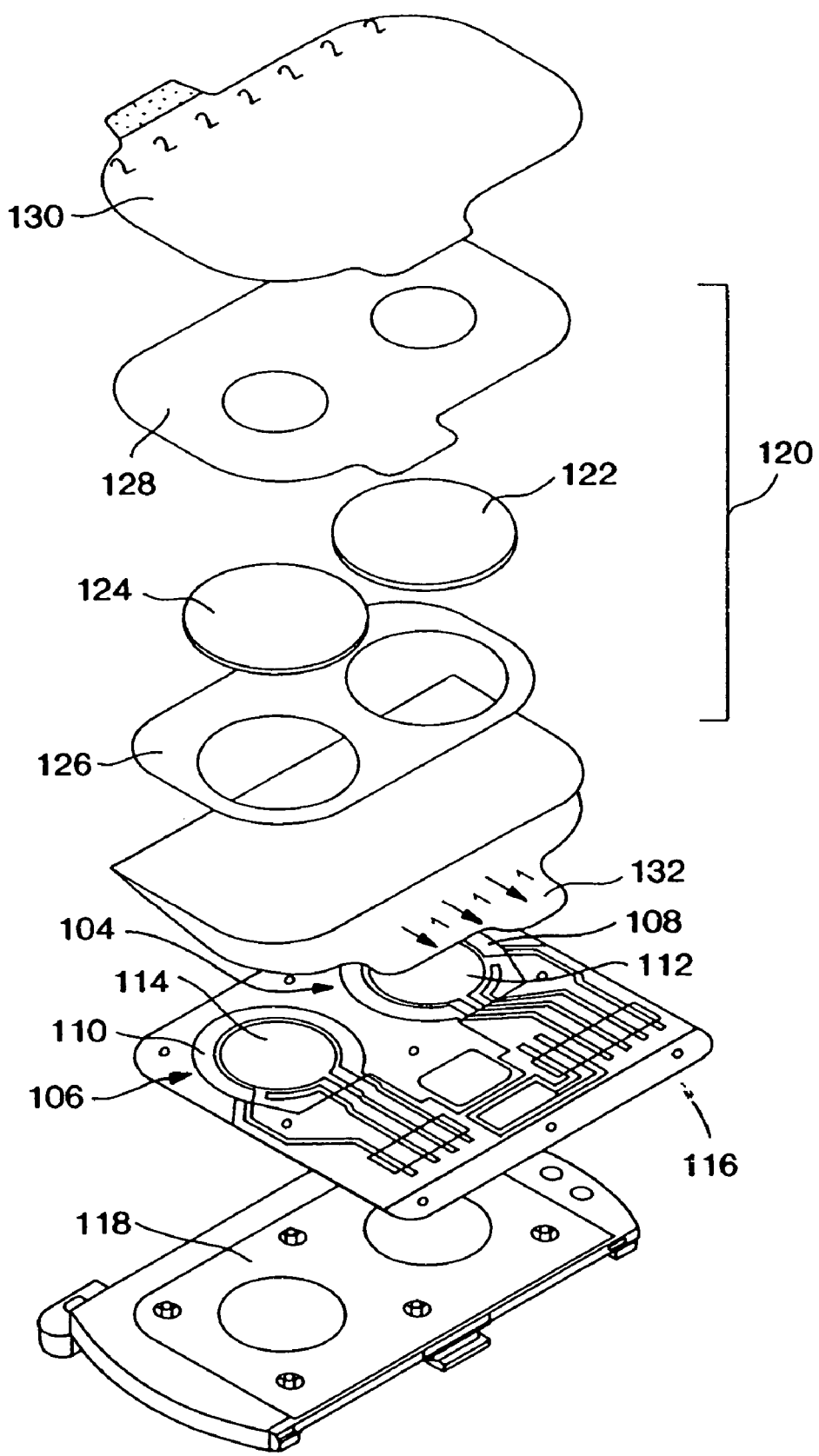
FIG. 8 presents a schematic of an exploded view of exemplary components comprising one embodiment of an AutoSensor for use in a monitoring system.

To sample the analyte, one or more collection reservoirs are placed in contact with a tissue surface on a subject. The ionically conductive material within the collection reservoir is also in contact with an electrode (for reverse iontophoretic extraction) which generates a current sufficient to extract glucose from the tissue into the collection reservoir. Referring to FIG. 8, an exploded view of exemplary components comprising one embodiment of an AutoSensor for use in an iontophoretic sampling system is presented. The AutoSensor components include two biosensor/iontophoretic electrode assemblies, 104 and 106, each of which have an annular iontophoretic electrode, respectively indicated at 108 and 110, which encircles a biosensor electrode 112 and 114. The electrode assemblies 104 and 106 are printed onto a polymeric substrate 116 which is maintained within a sensor tray 118. A collection reservoir assembly 120 is arranged over the electrode assemblies, wherein the collection reservoir assembly comprises two hydrogel inserts 122 and 124 retained by a gel retaining layer 126 and mask layer 128. Further release liners may be included in the assembly, for example, a patient liner 130, and a plow-fold liner 132. In an alternative embodiment, the electrode assemblies can include bimodal electrodes A polyurethane mask layer 128 as described in U.S. Pat. Nos. 5,827,183, 5,735,273, 6,141,573, 6,201,979, and 6,370,410, may be present. Other embodiments of the AutoSensor are described in U.S. Pat. Nos. 6,393,318, 6,341,232, and 6,438,414.

The mask and retaining layers are preferably composed of materials that are substantially impermeable to the analyte (e.g., glucose) to be detected (see, e.g., U.S. Pat. Nos. 5,735,273, and 6,341,232). By "substantially impermeable" is meant that the material reduces or eliminates analyte transport (e.g., by diffusion). The material can allow for a low level of analyte transport, with the proviso that the analyte that passes through the material does not cause significant edge effects at the sensing electrode used in conjunction with the mask and retaining layers. Examples of materials that can be used to form the layers include, but are not limited to, polyester, polyester derivatives, other polyester-like materials, polyurethane, polyurethane derivatives and other polyurethane-like materials.

The components shown in exploded view in FIG. 8 are intended for use in a automatic sampling system which is configured to be worn typically on the forearm, as described in PCT International Patent Application No. WO 96/00110. The housing can further include suitable electronics (e.g., one or more microprocessor(s), memory, display and other circuit components) and power sources for operating the automatic sampling system. The one or more microprocessors may control a variety of functions, including, but not limited to, control of a sampling device, a sensing device, aspects of the measurement cycle (e.g., timing of sampling and sensing, and alternating polarity between electrodes), connectivity, computational methods, different aspects of data manipulation (e.g., acquisition, recording, recalling, comparing, and reporting), etc.

The sensing electrode can be, for example, a Pt-comprising electrode configured to provide a geometric surface area of about 0.1 to 3 $cm^2$, preferably about 0.5 to 2 $cm^2$, and more preferably about 1 $cm^2$. This particular configuration is scaled in proportion to the collection area of the collection reservoir used in the sampling system of the present invention, throughout which the extracted analyte and/or its reaction products will be present. The electrode composition is formulated using analytical- or electronic-grade reagents and solvents which ensure that electrochemical and/or other residual contaminants are avoided in the final composition, significantly reducing the background noise inherent in the resultant electrode in particular, the reagents and solvents used in the formulation of the electrode are selected so as to be substantially free of electrochemically active contaminants (e.g., anti-oxidants), and the solvents in particular are selected for high volatility in order to reduce washing and cure times. Some electrode embodiments are described in EP 0 942 278 and GB 2 335 278.

The reactive surface of the sensing electrode can be comprised of any electrically conductive material such as, but not limited to, platinum-group metals (including, platinum, palladium, rhodium, ruthenium, osmium, and iridium), nickel, copper, silver, and carbon, as well as, oxides, dioxides, combinations or alloys thereof. Some catalytic materials, membranes, and fabrication technologies suitable for the construction of amperometric biosensors were described by Newman, J. D., et al. (Analytical Chemistry 67(24), 4594-4599, 1995).

Any suitable iontophoretic electrode system can be employed, an exemplary system uses a silver/silver chloride (Ag/AgCl) electrode system. The iontophoretic electrodes are formulated typically using two performance criteria: (1) the electrodes are capable of operation for extended periods, preferably periods of up to 24 hours or longer; and (2) the electrodes are formulated to have high electrochemical purity in order to operate within the present system which requires extremely low background noise levels. The electrodes must also be capable of passing a large amount of charge over the life of the electrodes. With regard to operation for extended periods of time, Ag/AgCl electrodes are capable of repeatedly forming a reversible couple which operates without unwanted electrochemical side reactions (which could give rise to changes in pH, and liberation of hydrogen and oxygen due to water hydrolysis). The Ag/AgCl electrode is thus formulated to withstand repeated cycles of current passage in the range of about 0.01 to 1.0 mA per cm² of electrode area. With regard to high electrochemical purity, the Ag/AgCl components are dispersed within a suitable polymer binder to provide an electrode composition which is not susceptible to attack (e.g., plasticization) by components in the collection reservoir, for example, the hydrogel composition. The electrode compositions are also typically formulated using analytical- or electronic-grade reagents and solvents, and the polymer binder composition is selected to be free of electrochemically active contaminants which could diffuse to the biosensor to produce a background current.

The automatic sampling system can transdermally extract the sample over the course of a selected period of time using reverse iontophoresis. The collection reservoir comprises an ionically conductive medium, preferably the hydrogel medium described herein above. A first iontophoresis electrode is contacted with the collection reservoir (which is typically in contact with a target, subject tissue surface), and a second iontophoresis electrode is contacted with either a second collection reservoir in contact with the tissue surface, or some other ionically conductive medium in contact with the tissue. A power source provides an electrical potential between the two electrodes to perform reverse iontophoresis in a manner known in the art. As discussed above, the biosensor selected to detect the presence, and possibly the level, of the target analyte (e.g., glucose) within a reservoir is also in contact with the reservoir. Typically, there are two collections reservoirs, each comprising glucose oxidase, and each in operative contact with iontophoretic electrode and a sensing electrode. The iontophoretic electrode may be a bimodal electrode that also serves, non-concurrently, as a counter electrode to the sensing electrode (see, e.g., U.S. Pat. No. 5,954,685).

In practice, an electric potential (either direct current or a more complex waveform) is applied between the two iontophoresis electrodes such that current flows from the first electrode through the first conductive medium into the skin, and back out from the skin through the second conductive medium to the second electrode. This current flow extracts substances through the skin into the one or more collection reservoirs through the process of reverse iontophoresis or electroosmosis. The electric potential may be applied as described in PCT International Patent Application No. WO 96/00110. Typically, the electrical potential is alternated between two reservoirs to provide extraction of analyte into each reservoir in an alternating fashion (see, e.g., U.S. Pat. Nos. 6,298,254, 6,023,629, and 5,771,890). Analyte is also typically detected in each reservoir.

As an example, to extract glucose, the applied electrical current density on the skin or tissue can be in the range of about 0.01 to about 2 mA/cm². In order to facilitate the extraction of glucose, electrical energy can be applied to the electrodes, and the polarity of the electrodes can be, for example, alternated so that each electrode is alternately a cathode or an anode. The polarity switching can be manual or automatic. Devices and methods for sampling of substances using alternating polarity are described in U.S. Pat. Nos. 6,298,254, 6,023,629, and 5,771,890.

When a bimodal electrode is used (e.g., U.S. Pat. No. 5,954,685), during the reverse iontophoretic phase, a power source provides a current flow to the first bimodal electrode to facilitate the extraction of the chemical signal into the reservoir. During the sensing phase, a separate power source is used to provide voltage to the first sensing electrode to drive the conversion of chemical signal retained in reservoir to electrical signal at the catalytic face of the sensing electrode. The separate power source also maintains a fixed potential at the electrode where, for example hydrogen peroxide is converted to molecular oxygen, hydrogen ions, and electrons, which is compared with the potential of the reference electrode during the sensing phase. While one sensing electrode is operating in the sensing mode it is electrically connected to the adjacent bimodal electrode which acts as a counter electrode at which electrons generated at the sensing electrode are consumed.

The electrode subassembly can be operated by electrically connecting the bimodal electrodes such that each electrode is capable of functioning as both an iontophoretic electrode and counter electrode along with appropriate sensing electrode(s) and reference electrode(s).

A potentiostat is an electrical circuit used in electrochemical measurements in three electrode electrochemical cells. A potential is applied between the reference electrode and the sensing electrode. The current generated at the sensing electrode flows through circuitry to the counter electrode (i.e., no current flows through the reference electrode to alter its equilibrium potential). Two independent potentiostat circuits can be used to operate the two biosensors. For the purpose of the present invention, the electrical current measured at the sensing electrode subassembly is the current that is correlated with an amount of chemical signal corresponding to the analyte.

The detected current can be correlated with the subject's blood glucose concentration (e.g., using a statistical technique or algorithm or combination of techniques) so that the system controller may display the subject's actual blood glucose concentration as measured by the sampling system. Such statistical techniques can be formulated as algorithm(s) and incorporated in one or more microprocessor(s) associated with the sampling system. Exemplary signal processing applications include, but are not limited to, those taught in the following U.S. Pat. Nos. 6,309,351, 6,299,578, 6,272,364, 6,233,471, 6,144,869, 6,356,776, 6,180,416, and 6,326,160.

In a further aspect of the present invention, the sampling/sensing mechanism and user interface may be found on separate components (see, e.g., PCT International Patent Application No. WO 0047109). Thus, the monitoring system can comprise at least two components, in which a first component comprises sampling mechanism and sensing mechanism that are used to extract and detect an analyte, for example, glucose, and a second component that receives the analyte data from the first component, conducts data processing on the analyte data to determine an analyte concentration and then displays the analyte concentration data. Typically, microprocessor functions (e.g., control of a sampling device, a sensing device, aspects of the measurement cycle, computational methods, different aspects of data manipulation or recording, etc.) are found in both components. Alternatively, microprocessing components may be located in one or the other of the at least two components. The second component of the monitoring system can assume many forms, including, but not limited to, the following: a small device that can, for example, be worn on the forearm, a credit card-shaped device (e.g., a "smart card" or "universal card" having a built-in microprocessor as described for example in U.S. Pat. No. 5,892,661), a pager-like device, cell phone-like device, or other such device that communicates information to the user visually, audibly, or kinesthetically.

Further, additional components may be added to the system, for example, a third component comprising a display of analyte values or an alarm related to analyte concentration, may be employed. In certain embodiments, a delivery unit is included in the system. An exemplary delivery unit is an insulin delivery unit. Insulin delivery units, both implantable and external, are known in the art and described, for example, in U.S. Pat. Nos. 5,995,860; 5,112,614 and 5,062,841. Preferably, when included as a component of the present invention, the delivery unit is in communication (e.g., wire-like or wireless communication) with the extracting and/or sensing mechanism such that the sensing mechanism can control the insulin pump and regulate delivery of a suitable amount of insulin to the subject.

Advantages of separating the first component (e.g., including the biosensor and iontophoresis functions) from the second component (e.g., including some microprocessor and display functions) include greater flexibility, discretion, privacy and convenience to the user. Having a small and lightweight measurement unit allows placement of the two components of the system on a wider range of body sites, for example, the first component may be placed on the abdomen or upper arm. This wider range of placement options may improve the accuracy through optimal extraction site selection (e.g., torso rather than extremities) and greater temperature stability (e.g., via the insulating effects of clothing). Thus, the collection and sensing assembly will be able to be placed on a greater range of body sites. Similarly, a smaller and less obtrusive microprocessor and display unit (the second component) provides a convenient and discrete system by which to monitor analytes. The biosensor readouts and control signals will be relayed via wire-like or wireless technology between the collection and sensing assembly and the display unit which could take the form of a small device worn on, for example, the forearm, a pager, or a credit card-sized device. This system also provides the ability to relay an alert message or signal during nighttime use, for example, to a site remote from the subject being monitored.

In one embodiment, the two components of the device can be in operative communication via a wire or cable-like connection. Operative communications between the components can be wireless link, i.e. provided by a "virtual cable," for example, a telemetry link. This wireless link can be uni- or bi-directional between the two components. In the case of more than two components, links can be a combination of wire-like and wireless.

5.0 Exemplary Analytes

The analyte can be any specific substance, component, or combinations thereof that one is desirous of detecting and/or measuring in a chemical, physical, enzymatic, or optical analysis. The PK-based method of the present invention may be employed as long as the detection/measurement of the analyte is time dependent, for example, the detection measurement method provides a response curve having a kinetic region.

Analytes that can be measured using the methods of the present invention include, but are not limited to, amino acids, enzyme substrates or products indicating a disease state or condition, other markers of disease states or conditions, drugs of abuse (e.g., ethanol, cocaine), therapeutic and/or pharmacologic agents (e.g., theophylline, anti-HIV drugs, lithium, anti-epileptic drugs, cyclosporin, chemotherapeutics), electrolytes, physiological analytes of interest (e.g., urate/uric acid, carbonate, calcium, potassium, sodium, chloride, bicarbonate ($CO_2$), glucose, urea (blood urea nitrogen), lactate and/or lactic acid, hydroxybutyrate, cholesterol, triglycerides, creatine, creatinine, insulin, hematocrit, and hemoglobin), blood gases (carbon dioxide, oxygen, pH), lipids, heavy metals (e.g., lead, copper), and the like. Analytes in non-biological systems may also be evaluated using the methods of the present invention.

In preferred embodiments, the analyte is a physiological analyte of interest, for example glucose, or a chemical that has a physiological action, for example a drug or pharmacological agent.

In order to facilitate detection of the analyte, an enzyme (or enzymes) can be disposed within the one or more collection reservoirs. The selected enzyme is capable of catalyzing a reaction with the extracted analyte to the extent that a product of this reaction can be sensed, for example, can be detected electrochemically from the generation of a current which current is detectable and proportional to the amount of the analyte which is reacted. In one embodiment of the present invention, a suitable enzyme is glucose oxidase, which oxidizes glucose to gluconic acid and hydrogen peroxide. The subsequent detection of hydrogen peroxide on an appropriate biosensor electrode generates two electrons per hydrogen peroxide molecule creating a current that can be detected and related to the amount of glucose entering the device. Glucose oxidase is readily available commercially and has well known catalytic characteristics. However, other enzymes can also be used singly (for detection of individual analytes) or together (for detection of multiple analytes), as long as they specifically catalyze a reaction with an analyte or substance of interest to generate a detectable product in proportion to the amount of analyte so reacted.

In like manner, a number of other analyte-specific enzyme systems can be used in the invention, which enzyme systems operate on much the same general techniques. For example, a biosensor electrode that detects hydrogen peroxide can be used to detect ethanol using an alcohol oxidase enzyme system, or similarly uric acid with urate oxidase system, cholesterol with a cholesterol oxidase system, and theophylline with a xanthine oxidase system.

In addition, the oxidase enzyme (used for hydrogen peroxidase-based detection) can be replaced or complemented with another redox system, for example, the dehydrogenase-enzyme NAD-NADH, which offers a separate route to detecting additional analytes. Dehydrogenase-based sensors can use working electrodes made of gold or carbon (via mediated chemistry). Examples of analytes suitable for this type of monitoring include, but are not limited to, cholesterol, ethanol, hydroxybutyrate, phenylalanine, triglycerides, and urea.

Further, the enzyme can be eliminated and detection can rely on direct electrochemical or potentiometric detection of an analyte. Such analytes include, without limitation, heavy metals (e.g., cobalt, iron, lead, nickel, zinc), oxygen, carbonate/carbon dioxide, chloride, fluoride, lithium, pH, potassium, sodium, and urea. Also, the sampling system described herein can be used for therapeutic drug monitoring, for example, monitoring anti-epileptic drugs (e.g., phenyloin), chemotherapy (e.g., adriamycin), hyperactivity (e.g., ritalin), and anti-organ-rejection (e.g., cyclosporin)

Preferably, a sensor electrode is able to detect the analyte that has been extracted into the one or more collection reservoirs when present at nominal concentration levels. Suitable exemplary biosensor electrodes and associated sampling systems as described in are described in PCT International Patent Application Nos. WO 97/10499 and WO 98/42252.

Further, the PK-based methods of the present invention facilitate analysis of multiple analytes obtained in a single sample (e.g., a sample collected into a single reservoir using transdermal extraction), even when such multiple analytes are being detected by a common reaction product. For example, a sensing device may be used that employs several oxidase enzymes, for example, lactate oxidase, uricase, and glucose oxidase. Each of these enzymes has the ability to generate hydrogen peroxide when contacted by their respective substrates. A single sensor sensitive to, for example, hydrogen peroxide (e.g., a platinum electrode), cannot differentiate between peroxide originating from glucose, uric acid or lactic acid. However, by employing the PK-based methods of the present invention, the apparent rate constant for each reaction and the concentration of each analyte can be resolved, that is, the PK-based method can resolve the individual contributions to overall, final, peroxide-mediated signal. Thus, with suitable computing power, the concentrations of each analyte can be obtained. Variables, such as, pH and enzyme concentration, allow manipulation of the apparent rate constants of each enzyme to aid resolution and minimize interference between components. Further, a system of weighting factors could be employed as well, where, for example, contributions by different components are weighted differently based on their known contribution to overall signal.

Typically, the reactions with substrate to form detectable product, as facilitated by different enzymes, do not interfere with one another. The PK-based methods described herein are particularly useful for detection of multiple analytes using a common reaction product, for example, hydrogen peroxide, when there are at least three-fold differences, preferably five-to ten-fold difference or higher, in the reaction rate constants for conversion of the different analytes to the common reaction product. For example, detection of glucose and urea in a single sample may be facilitated by the use of the enzymes glucose oxidase and uricase (urate oxidase) both of which yield hydrogen peroxide as the common, detectable reaction product. The $k_m$ of glucose oxidase is approximately $3.3 \times 10^{-2}$ molar and the $k_m$ of uricase is approximately $10^{-5}$ molar. For example, signals corresponding to glucose and urea can be resolved within a single signal response curve based on the apparent rate constants (i.e., the $k_m$) of the two reactions using the parallel first order predictive-kinetic model described herein.

In the example described above a common reaction product is formed (i.e., hydrogen peroxide); however, this is not a requirement. A single sensor may detect multiple analytes and/or reaction products of analytes. For example, a platinum sensor could be used to detect tyrosine and glucose in a single sample. The tyrosine is detected, for example, by direct electrochemical oxidation at a suitable electrode potential (e.g., approximately 0.6V vs. Ag/AgCl). The glucose is detected, for example, using glucose oxidase and detecting the hydrogen peroxide reaction product. For example, signals corresponding to tyrosine and glucose can be resolved within a single signal response curve based on the apparent rate constants (i.e., the $k_m$) of the two reactions using the parallel first order predictive-kinetic model described herein.

Generally when detecting multiple analytes with a single sensor it is preferred that, within a single response curve, the primary signals corresponding to each analyte are separated in time, for example, one analyte's reaction with the sensor is rapid ($k_1$) and a second analyte's reaction with the sensor is slower ($k_2$), i.e., $k_1 \gg k_2$.

Different sensing devices and/or sensing systems can be employed as well to distinguish between signals. For example, a first gel containing glucose oxidase associated with a first platinum sensor can be used for the detection of glucose, while a second gel containing uricase associated with a second platinum sensor can be used for the detection of urea The PK-based methods of the present invention may then used to individually model the signal response curves generated at each sensor Experimental The following examples are put forth so as to provide those of ordinary skill in the art with a complete disclosure and description of how to make and use the devices, methods, and formulae of the present invention, and are not intended to limit the scope of what the invention regards as the invention. Efforts have been made to ensure accuracy with respect to numbers used (eg, amounts, temperature, etc, but some experimental errors and deviations should be accounted for. Unless indicated otherwise, parts are parts by weight, molecular weight is weight average molecular weight, temperature is in degrees Centigrade, and pressure is at or near atmospheric.

EXAMPLE 1

Discussion of the PK and 7-Minutes Integration Methods

Data were collected using GlucoWatch biographers on human subjects. The electrode response to the glucose was monitored. The current responses were then transferred to a computer for data processing. The subjects were monitored for approximately 26 hours. Briefly, samples comprising glucose were transdermally extracted from the subject using a GlucoWatch biographer in operative contact with a skin surface of each subject. Measured current signals were obtained over time. The measured current signals comprised a measured current signal response current curve, from the extracted glucose, wherein the measured current signal is specifically related to the amount of glucose in a hydrogel of a GlucoWatch biographer. After integration, a measured charge signal over time was obtained. The measured charge signal comprised a measured charge signal response curve that was specifically related to the amount (or concentration) of glucose in the hydrogel.

Raw data from 25 GlucoWatch biographers were analyzed using both the 7-minute fixed-point integration method (see, e.g., GlucoWatch biographer in the Definition Section 1.0.0-1.1.2) and the $S_\infty$ PK approach (see, Section 2.0.0, Predictive Kinetics). The results of the two methods were compared The "nC slope" is the least-squares slope of the line of the relation between the charge signal and the reference BG. It is given in (nC/(mg/dL)), and can be considered as a measure of the system sensitivity.

Table 2 presents a data comparison from the two methods showing average nC slopes for different time intervals obtained from the 7-minute and the PK integration methods. In Table 2 average nC slopes based on data from 25 Gluco-Watch biographer are compared. Because 26-hour data exhibited a significant signal decline over time, the nC slopes are listed separately for three shorter time intervals T1 (3 hr-10 hr), T2 (10 hr-17 hr) and T3 (17 hr-26 hr).

TABLE 2

| SLOPE | 3 hr-10 hr (T1) | | 10 hr-17 hr (T2) | | 17 hr-26 hr (T3) | |
|---|---|---|---|---|---|---|
| (nC/(mg/dl)) | 7 min | PK | 7 min | PK | 7 min | PK |
| Average | 368 | 432 | 156 | 213 | 77 | 87 |
| Std. Dev. | 205 | 256 | 44 | 72 | 37 | 69 |

Based on the comparison of the "nC slopes," the PK method gave higher sensitivity than the $S_\infty$ 7-minute integration. However, as shown by the data presented in Table 3, the PK-estimated charge showed somewhat lower correlation to the reference BG than the 7-minute-integral charge. The data in Table 3 show the correlation for different time intervals obtained from the 7-minute and the PK integration methods. The coefficient of determination of the correlation ($R^2$) is an indicator of the degree of fit between the integral value and the glucose concentration as given by the Reference Blood Glucose reading.

TABLE 3

|  | 3 hr-10 hr (T1) | | 10 h-17 hr (T2) | | 17 hr-26 hr (T3) | |
| --- | --- | --- | --- | --- | --- | --- |
| R2 | 7 min | PK | 7 min | PK | 7 min | PK |
| Average | 0.79 | 0.75 | 0.93 | 0.89 | 0.80 | 0.78 |

As can be seen from the data presented above, there was a dramatic decrease in signal over time with both the 7-minute and $S_\infty$ PK methods. Both methods lead to charge signal estimates that exhibited similar signal decline. This is further illustrated in Table 4, where the ratios of nC slopes for different time intervals are given in terms of percentages.

TABLE 4

|  | T2/T1 | | T3/T1 | | T3/T2 | |
| --- | --- | --- | --- | --- | --- | --- |
| Slope Ratios | 7 min | PK | 7 min | PK | 7 min | PK |
| Average (%) | 57.4 | 58.8 | 35.8 | 37.7 | 53.6 | 47.3 |
| Std. Dev. (%) | 39.5 | 34.7 | 49.4 | 66.9 | 30.2 | 41.9 |

These results suggested that a direct application of the $S_\infty$ PK approach may not completely compensate for signal decay.

EXAMPLE 2

The $1/k_2$ Effect

Figure 16:
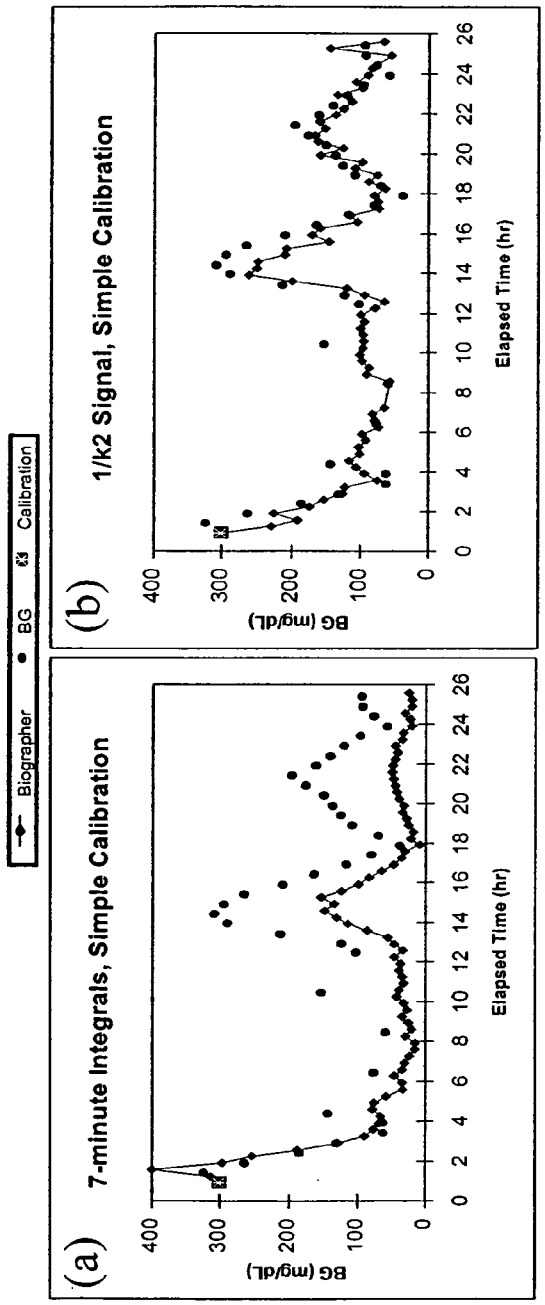
FIG. 16 presents an example of the $1/k_2$ effect. The curves represent 7-minute-integrated charge signal with simple calibration (panel a), and $1/k_2$ signal with simple calibration (panel b) (both calibrated at 1 hr elapsed time by matching the signals to the blood glucose (BG) value). The asterisk represents the calibration point. The circular points (no line) correspond to the reference BG profile. Note that the 7-minute signal decays considerably whereas the $1/k_2$ signal exhibits no apparent signal decay at later time points. In the figure, GlucoWatch biographer readings are indicated by a line (where individual measurements are represented as diamonds), BG readings are indicated by circles, and the calibration point is indicated by an asterisk. In the figure, the vertical axis is blood glucose (BG) in mg/dL and the horizontal axis is Elapsed Time in hours (hr).

A typical example of the $1/k_2$ effect is shown in FIG. 16(b). In this example, the charge signal was calculated using the 7-minute fixed-point method (FIG. 16, panel a) and $1/k_2$ calculated from the 3-min data fit to the PK Eq. (3A) (FIG. 16, panel b), as follows:

$$Q(t) = S_o + \frac{c_1}{k_1}(1 - e^{-k_1 t}) + \frac{c_2}{k_2}(1 - e^{-k_2 t}) \quad \text{(Eq. 3A)}$$

The fixed point-method values and the $1/k_2$ values were plotted together with the reference BG as functions of the elapsed time (ET). Both 7-minute charge signal and the $1/k_2$ signal had been converted into glucose readings using simple single-point calibration at 1 hour ET. An exemplary calculation of glucose concentration based on charge signal is as follows:

$$[Glu]_t = \frac{[Glu]_{cal}}{nC_{cal}} (nC(\text{from 7 min signal}))_t$$

where $Glu_t$ is the glucose concentration at time t, $Glu_{cal}$ is the glucose concentration at the time of calibration that corresponds to $nC_{cal}$, the nC charge (integral of current) at the time of calibration, and (nC 7 min signal), is the nC signal over 7 minutes at time t.

An exemplary calculation based on $1/k_2$ is as follows:

$$[Glu]_t = \frac{[Glu]_{cal}}{(1/k_2)_{cal}} (1/k_2)_t$$

where $Glu_t$ is the glucose concentration at time t, $Glu_{cal}$ is the glucose concentration at the time of calibration that corresponds to the estimated $1/k_2$ at the time of calibration, and $(1/k_2)_t$ is the estimated $1/k_2$ at time t.

(In case where the 1/k2 effect is caused by the fact that the mutarotation rate depends on the glucose concentration in a way typical for enzymatic reactions, the calibration formula should have a somewhat more general form than that presented above. More specifically, if $\alpha \to \beta$ mutarotation rate $k_\alpha$ is $$k_\alpha = \frac{f_\alpha}{m + [\alpha]}$$

where $[\alpha]$ is the $\alpha$-glucose concentration, and $f_\alpha$, and m are parameters of the mutarotation enzymatic reaction and that $k_2$ is essentially the same as $k_\alpha$, then the calibration formula would have the form:

$$[Glu]_t = \frac{[Glu]_{cal} - B}{(1/K_2)_{cal}} (1/K_2)_t + B$$

where B is an adjustable parameter related to $f_\alpha$ and m.)

The blood glucose profile exhibited three pronounced peaks: the initial peak at about 1.5 hours ET, the second high peak reaching over 300 mg/dL at 15 hours ET, and the third smaller BG peak at about 21 hours. The 7-minute-integral charge signal followed all three peaks, but exhibited strong signal decay, so that the reflection of the third BG peak was barely visible in the 7-minute-integral calibrated signal. In contrast, the $1/k_2$ signal not only closely tracked the BG changes, but also showed no sign of signal decay.

EXAMPLE 3

Analysis of the Correlation of $K_{min}$ and $K_{ratio}$ to Analyte Amount or Concentration In order to confirm the obvious visual observations exemplified in FIG. 16 in a more quantitative way, the data from 119 GlucoWatch biographers was analyzed.

Both $K_{min}$ and $K_{ratio}$ analyses were performed on data sets from 119 GlucoWatch biographers that had been applied to human subjects. The same execution steps were followed to calculate $\{c_1, c_2, k_1, \text{ and } k_2\}$ values for each cathode cycle. Then $K_{min}$ and $K_{ratio}$ analysis were calculated and paired with reference BG values.

Because each estimate (i.e., fitted parameter) had different units, a one point calibration was done at Elapsed Time (ET) 1:14 (or first available reference BG) and estimated glucose values were converted into same unit (mg/dl). The parameters $c_1, c_2, k_1,$ and $k_2$ were estimated using the following equation fitted to the first three minutes of signal charge data at each time point:

$$Q(t) = S_o + \frac{c_1}{k_1}(1 - e^{-k_1 t}) + \frac{c_2}{k_2}(1 - e^{-k_2 t}) \qquad \text{(Eq. 3A)}$$

The data were collected at room temperature using GlucoWatch biographers on human subjects as described above. The PK model, Eq. (3A), was fitted to an initial portion (typically the first three minutes) of the GlucoWatch biographer charge signal, and values for the parameters were determined. The nonlinear fitting (optimization of the model parameters) was performed using the minimization algorithm Levenberg-Marquardt. The mathematical model, represented by Eq. (3A), and an error minimization method (Levenberg-Marquardt) were used to iteratively estimate values of the parameters using the model and error minimization method to fit a predicted response curve to the measured signal response curve. The error minimization method provided a calculated error based on differences between the predicted and measured signal response curves. The estimating was iteratively performed until the calculated error between the predicted and measured signal response curves was a minimum (i.e., using alternative values of the fitted parameters produced higher error) or until no further statistically significant change was seen in the calculated error, at which time iterative estimation of the parameters was stopped. The iterative estimation and error minimization resulted in a predicted response curve corresponding to the measured signal response curve. Further, the iterative estimation provides estimated values for all parameters in the mathematical model including $c_1$, $c_2$, $k_1$, and $k_2$.

Glucose concentration was calculated as described in Example 2 for the $1/k_2$, using the following equation:

$$[Glu]_t = \frac{[Glu]_{cal}}{(1/k_2)_{cal}}(1/k_2)_t$$

Least squares slope, least squares intercept and correlation analyses were performed for the $K_{min}$ and $K_{ratio}$ methods at different intervals. The averaged values for 119 GlucoWatch biographers are presented in Tables 5, 6, and 7. In these tables, the first interval corresponds to Elapsed Time (ET) 1:34 to 7:54, second interval corresponds to ET 8:14 to 16:54, and third interval corresponds to ET 17:14 to 25:54. Performances of both $K_{min}$ and $K_{ratio}$ were investigated.

In Table 5, averaged correlation values for each method at different time intervals are presented. The data in Table 5 represent averaged coefficients of determination correlation. In Table 5, correlations less than 0 were not included in the averages and correlations of only two paired points, which result in 1.0, were not included in the analysis.

TABLE 5

| RSQUARE | First Interval | | Second Interval | | Third Interval | |
|---|---|---|---|---|---|---|
| | Kmin | Kratio | Kmin | Kratio | Kmin | Kratio |
| mean | 0.57 | 0.53 | 0.65 | 0.66 | 0.53 | 0.53 |
| stdev | 0.31 | 0.34 | 0.29 | 0.29 | 0.30 | 0.31 |

| | ALL | |
|---|---|---|
| RSQUARE | Kmin | Kratio |
| mean | 0.47 | 0.47 |
| stdev | 0.29 | 0.29 |

Although correlation values for the $K_{min}$ and $K_{ratio}$ methods were slightly low, the low correlation of $K_{min}$ in the smaller segments might be due to the variations in the $k_2$ estimation and may be fixed by optimizing the prediction parameters. However, even these slight variations in $k_2$ estimation do not effect the overall performance of the $k_2$ parameter as an indicator of analyte concentration or amount Further, the data showed a good averaged correlation in the 25-hour run.

In Table 6, averaged slopes for each method at different time intervals are presented. In Table 6, slopes less than zero were not included it the averages, and slopes greater than 2.0 in the first interval were not included in the averages. The new methods, especially $K_{min}$, had consistent slope for all intervals Overall (Table 6, ALL), $K_{min}$ had higher averaged slope, which means higher analyte sensitivity.

TABLE 6

| SLOPE | First Interval | | Second Interval | | Third Interval | |
|---|---|---|---|---|---|---|
| | Kmin | Kratio | Kmin | Kratio | Kmin | Kratio |
| mean | 0.73 | 0.57 | 0.83 | 0.62 | 0.62 | 0.43 |
| stdev | 0.45 | 0.38 | 0.64 | 0.53 | 0.49 | 0.33 |

| | ALL | |
|---|---|---|
| SLOPE | Kmin | Kratio |
| mean | 0.66 | 0.51 |
| stdev | 0.46 | 0.35 |

The data in Table 6 support that $K_{min}$ and $K_{ratio}$ provide sensitive indicators of analyte concentration or amount that do not decay over the 26 hour time course of the experiment.

In order to investigate whether $K_{min}$ and $K_{ratio}$ were subject to signal decay, a decay index was used. Slope ratios between intervals were calculated to quantify the signal decay from one interval to another. The Slope Ratio was as follows:

$$SlopeRatio_{AB}(\%) = \frac{Slope\,@\,Interval\,A}{Slope\,@\,Interval\,B}$$

In Table 7, averaged slope ratios for each method at different time intervals are presented. In Table 7, ratios of less than 0 and greater than 300% were not included in the analysis.

TABLE 7

| Slope Ratio | T2/T1 | | T3/T1 | | T3/T2 | |
|---|---|---|---|---|---|---|
| | $K_{min}$ | $K_{ratio}$ | $K_{min}$ | $K_{ratio}$ | $K_{min}$ | $K_{ratio}$ |
| mean | 112.3% | 109.7% | 90.3% | 84.6% | 76.2% | 84.7% |
| st. dev | 74.1% | 68.5% | 66.0% | 62.7% | 46.0% | 65.0% |

The data presented above support the conclusion that both $K_{min}$ and $K_{ratio}$ keep the signal level steady for entire run. Accordingly, these data suggest that signal decay had a reduced effect on determination of analyte concentration or amount when using $K_{min}$ and $K_{ratio}$ as parameters for the estimating of analyte concentration or amount. A comparison of the results obtained with the $S_\infty$ PK method and the $1/k_2$ method are presented in Example 4.

In conclusion, it is seen that $K_{min}$ ($1/k_2$) is proportional to the glucose concentration in the gel. Higher glucose concentration in the gel possibly slows down the slower process and appears in the predicted time constants The high correlation of $K_{min}$ (1/$k_2$) to reference BG with less signal decay makes it potentially valuable candidate as an input to an alternative algorithm that may increase the useable duration of future generation GlucoWatch biographer monitoring devices.

EXAMPLE 4

Comparison of the Results of the $S_\infty$ PK Method to the 1/$k_2$ Method

The results obtained from the 1/$k_2$ signals were compared to the results from the charge signals, which were estimated using the $S_\infty$ PK method (Example 3, also, see above, Section 2.0.0, Predictive Kinetics). Because the PK data were very similar to the charge signals obtained from the 7-minute-integration method, only the PK results were used as a reference; but a similar contrast can be expected for the 7-minute integration method.

Because the 1/$k_2$ signal and charge signal have different units, they cannot be compared directly. Therefore, single-point calibration by matching known blood glucose with the signals was assumed at 1:14 hour ET (or at first available reference BG). Then, the analysis was done for the calibrated signal (given in mg/dl). Several obvious visual outliners (176 out of 8925 readings) were removed for the purpose for this analysis. Least-squares slope and correlation coefficient with respect to the reference BG were calculated for both kinds of signals at different ET intervals. The first (early) time interval corresponded to ET between 1:34 hr and 7:54 hr, the second (middle) interval corresponded to 8:14 hr to 16:54 hr, and the third (late) interval was between 17:14 hr and 25:54 hr ET The averaged per-GlucoWatch biographer results are presented in Table 8. In Table 8, the averaged slopes and correlation are plotted versus reference BG for different time intervals obtained from the calibrated PK charge signal and from the calibrated 1/$k_2$ signal.

TABLE 8

| | | PK ($S_\infty$) | | 1/$k_2$ | |
|---|---|---|---|---|---|
| Time Period | Slope Ratio | Slope | $R^2$ | Slope | $R^2$ |
| Early (T1) | Mean | 0.84 | 0.59 | 0.73 | 0.57 |
| (ET: 1:34-7:54) | Std. Dev. | 0.47 | | 0.45 | |
| Middle (T2) | Mean | 0.39 | 0.68 | 0.83 | 0.65 |
| (ET: 8:14-16:54) | Std. Dev. | 0.30 | | 0.64 | |
| Late (T3) | Mean | 0.22 | 0.63 | 0.62 | 0.53 |
| (ET: 17:14-25:54) | Std. Dev. | 0.18 | | 0.49 | |
| All Periods | Mean | 0.42 | 0.34 | 0.66 | 0.47 |
| (ET: 1:34-25:54) | Std. Dev. | 0.30 | | 0.46 | |

Although the $S_\infty$ PK method initially (in the "early" time period) leads to a higher slope, it diminishes quickly in the subsequent time intervals. On the other hand, the 1/$k_2$ calibrated signal exhibits almost the same slopes for all time intervals. In the entire monitoring period, 1/$k_2$ gives an averaged slope higher that the $S_\infty$ PK approach. This means that the 1/$k_2$ approach provides higher sensitivity than the PK method, and consequently also higher sensitivity than the standard 7-minute method.

Ratios of average slopes for different time intervals and for different methods are presented in Table 9. These ratios can be used to quantify the degree of signal decay. The conclusion that the charge signal obtained using $S_\infty$ PK method is subject to signal decay is confirmed by the data in Table 9. On average, the PK signal in the second (middle) interval is only half (51%) of the signal in the first (early) interval, and in the third (late) interval it becomes just one-third (33%) of the signal in the early interval On the other hand, the 1/$k_2$ signal keeps roughly the same level through the whole run. Table 9 presents ratios of averaged slopes for different time intervals (calibrated PK charge signal vs. calibrated 1/$k_2$ signal).

TABLE 9

| Time Periods | | PK ($S_\infty$) | 1/$k_2$ |
|---|---|---|---|
| Middle/Early = T2/T1 | Mean (%) | 51 | 112 |
| | Stdev | 43 | 74 |
| Late/Early = T3/T1 | Mean (%) | 33 | 90 |
| | Stdev | 39 | 66 |
| Late/Middle = T3/T2 | Mean (%) | 62 | 76 |
| | Stdev | 48 | 46 |

These results presented in Tables 8 and 9 suggest that the methods of the present invention have more consistent slope values among the early (Elapsed Time 1:34-7:54), middle (Elapsed Time 8:14-16:54) and late (Elapsed Time 17:14-25:54) time intervals as compared to the $S_\infty$ PK application. Slope is a good indication of sensitivity of the system. The more consistent sensitivity means the more stable system. Further, the methods of the present invention are less susceptible to signal decay relative to the $S_\infty$PK method. Slope ratios are good signal decay indicators. Slope ratio of the methods of the present invention stayed in ~10% range of the early interval for middle and late intervals. However, the signal ($S_\infty$) of the $S_\infty$ PK method decayed 50% from early to middle, and 66% from early to late. Signal decay is one of the most important features to be improved for a stable and reliable system. Also, the methods of the present invention had similar correlation with reference BG as the $S_\infty$ PK method over short time; but it had higher correlation with reference BG correlation over long time since it resolved the signal decay problem over long time.

Direct application of the 1/$k_2$ effect as a method to track blood glucose (or other analyte levels, e.g., amount or concentration) provided good results. Moreover, the 1/$k_2$ effect can be used as a basis to develop various new methods to compensate the signal decay. An example of such a method has been described above. Basic analysis of raw (unscreened) data, led to the conclusion that the new signal processing methods based on the 1/$k_2$ effect performed better than the $S_\infty$ PK method and better than the standard 7-minute integration method (although both of these methods provide good, reliable estimates of blood glucose concentration over defined time intervals). The 1/$k_2$-based methods described herein gave higher sensitivity, less signal decay, and higher overall correlation with the reference BG.

As can be seen from the data presented above, in general, the 1/$k_2$ method provides an improvement relative to the $S_\infty$ PK method. Because the $S_\infty$ PK method and the standard 7-minute integration method provide similar results (see Example 1), these results suggest that the 1/$k_2$ method provides an improvement relative to the standard 7-minute integration method as well. The 1/$k_2$ method gives higher sensitivity, less signal decay, and higher overall correlation.

EXAMPLE 5

Compensation for Signal Decay

Figure 17:
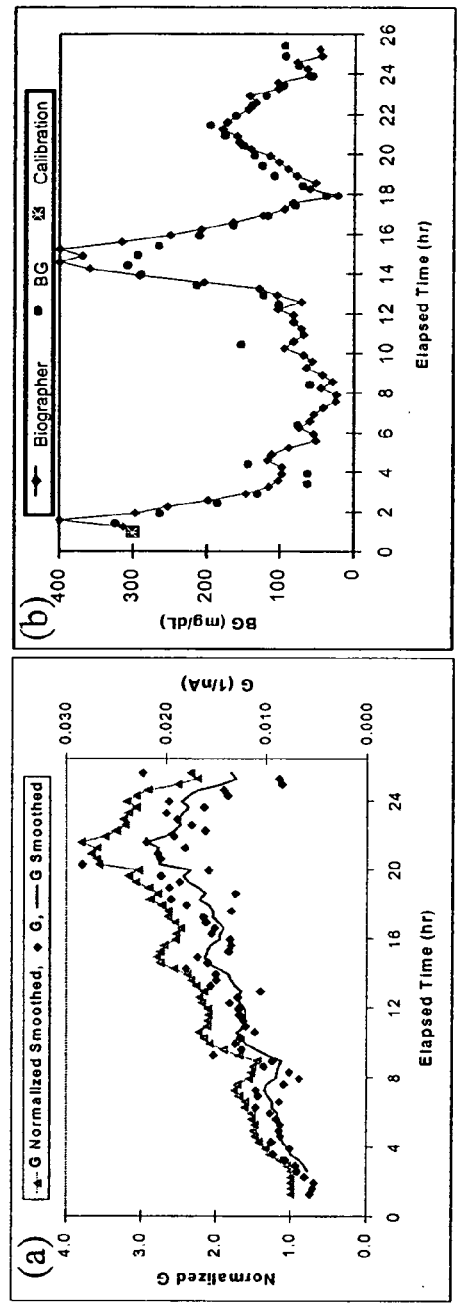
FIG. 17, panel (a), presents data related to the Gain factor (diamonds), the same gain factor smoothed by 5-point moving average (curve that tracks the diamond points), and the normalized, smoothed Gain factor (G Normalized Smoothed; triangles). In panel (a), the normalized Gain factor is the left vertical axis (Normalized G) and the Gain factor is the right vertical axis (G; 1/nA) both are plotted relative to Elapsed time in hours (hr) which is the horizontal axis.

In FIG. 17, panel (a), the gain factor G (calculated as the average for sensors A and B from the same data set that was used to illustrate the 1/$k_2$ effect in FIG. 16), is plotted as a function of the elapsed time (FIG. 17, panel (a); diamonds). In the figure, the solid curve represents the gain factor smoothed by using 5-point moving average. Because it is not expected that G to depends on BG, the smoothing operation is justified here as it should not cause any loss of information about the actual BG. Triangles correspond to the same smoothed G factor, but normalized by the first available C value. While smoothing the data, the first four points of G were lost. These points were replaced with "1" in the normalized version. This procedure should not effect the results, because there was very little signal decay observed in the first 2 hours of GlucoWatch biographer operation. The normalized gain factor provides a rough estimate of how much signal decay appears in a GlucoWatch biographer application. In the particular case shown in FIG. 17, the signal at about 24 hour ET was almost four times smaller than at the beginning of the monitoring period. Note that G measures signal decay individually for each particular GlucoWatch biographer application, and can be used to compensate signal decay "on the run" or in real time. This is relevant, because signal decay may vary significantly for different subjects as well as for different GlucoWatch biographer applications for the same subject.

The charge signal calculated using the 7-minute fixed-point method (plotted in FIG. 16 panel (a)) was corrected for signal decay by multiplying it by the normalized and smoothed gain factor G. The normalized, smoothed Gain factor was obtained by taking a five point moving average $1/c_2$ value. For example, the charge at time t (i.e., the charge based on a full measurement cycle where the glucose-related charge values from sensors A and B are averaged) is multiplied by an average $1/c_2$ value, where the average is based on the $1/c_2$ values for times t, (t-1), (t-2), (t-3), and (t-4). The resulting signal (calibrated at 1 hr ET by matching the signal to the BG value) is plotted in FIG. 17(b) together with the reference BG data. It was seen that the described procedure of signal decay compensation works very well, as shown in the data presented herein.

Statistical analysis of 116 GlucoWatch biographers confirmed that the described above method for signal decay compensation leads to signal-decay-compensated 7-minute charge signals that exhibit high and consistent slopes, and high correlation with the reference BG in the whole 25-hours monitoring period. This is illustrated in Table 10, where ratios of average slopes for different time intervals and for the standard 7-minute integral method are compared with those corrected for the signal decay. Table 10 presents the data for ratios of averaged slopes for different time intervals and 7-minute-integration charge signal versus the same signal compensated for signal decay.

TABLE 10

| Time Periods Slope Ratio | | 7-minute-integration signal | Compensated 7-minute signal |
|---|---|---|---|
| Middle/Early = T2/T1 | Mean (%) | 44 | 101 |
| | Stdev | 36 | 76 |
| Late/Early = T3/T1 | Mean (%) | 32 | 101 |
| | Stdev | 26 | 72 |
| Late/Middle = T3/T2 | Mean (%) | 67 | 98 |
| | Stdev | 43 | 50 |

Table 11 presents a comparison of performance of the 7-minute integration method (7 min), the $S_\infty$ PK method (PK), $1/k_2$-signal method ($1/k_2$), and the method of correcting the 7-minute charge signal using the gain factor $G=1/c_2$ (G-7 min). Due to difference between data conditioning schemes and the number of GlucoWatch biographers in the studies presented above, it was difficult to create a performance comparison matrix for the different methods. Accordingly, a performance comparison matrix was created (Table 11) for the same data set and the same GlucoWatch biographers from a study size comprising 107 GlucoWatch biographers. The GlucoWatch biographers were calibrated at ET 1:14 or with the first available Reference Blood Glucose value with a simple one-point calibration (the MOE algorithm was not applied).

The performance metrics were as follows. For various time intervals, Mean Relative Difference (MRD), Mean Absolute Relative Difference (MARD), slope and coefficient of determination (R2) are given for the calibrated at 1:14 ET signals, relative to the reference BG. For each method, and for different time intervals, Table 11 lists Mean Relative Difference (MRD), Mean Absolute Relative Difference (MARD), coefficient of determination (R2), and slope of the signals (calibrated at 1:14 ET) relative to the reference BG. (MRD is defined as the mean of the differences between the calibrated signal and reference BG normalized by the reference BG, and MARD is defined as the mean of absolute values of the differences between the calibrated signal and reference BC, again normalized by the reference BG).

TABLE 11

| | | MRD | | MARD | | Slope | | R2 |
|---|---|---|---|---|---|---|---|---|
| | | Average | Std. Dev. | average | Std. Dev. | average | Std. Dev. | Average |
| Early (T1) | 7 min | −17% | 25% | 28% | 18% | 0.87 | 0.48 | 0.66 |
| (ET: 1:14-7:54) | PK | −20% | 24% | 31% | 18% | 0.90 | 0.50 | 0.64 |
| | 1/k2 | 6% | 33% | 33% | 19% | 0.84 | 0.64 | 0.57 |
| | G-7 min | −3% | 28% | 27% | 16% | 0.78 | 0.54 | 0.61 |
| Middle (T2) | 7 min | −60% | 21% | 63% | 14% | 0.36 | 0.23 | 0.70 |
| (ET: 8:14-16:54) | PK | −62% | 20% | 65% | 15% | 0.38 | 0.27 | 0.68 |
| | 1/k2 | −14% | 49% | 44% | 30% | 0.80 | 0.57 | 0.67 |
| | G-7 min | −9% | 50% | 42% | 32% | 0.77 | 0.51 | 0.67 |
| Late (T3) | 7 min | −67% | 18% | 68% | 15% | 0.26 | 0.15 | 0.66 |
| (ET: 17:14-25:54) | PK | −69% | 17% | 70% | 15% | 0.23 | 0.18 | 0.65 |
| | 1/k2 | −20% | 42% | 46% | 21% | 0.60 | 0.37 | 0.56 |
| | G-7 min | −4% | 55% | 48% | 32% | 0.79 | 0.48 | 0.60 |
| All periods | 7 min | −51% | 17% | 55% | 12% | 0.42 | 0.28 | 0.34 |
| (ET: 1:14-25:24) | PK | −53% | 17% | 57% | 12% | 0.44 | 0.34 | 0.34 |
| | 1/k2 | −12% | 35% | 40% | 17% | 0.69 | 0.46 | 0.46 |
| | G-7 min | −4% | 43% | 41% | 25% | 0.69 | 0.41 | 0.53 |

The results demonstrate that the methods of the present invention (both $1/k_2$ and correction for signal decay using $1/c_2$) result in higher sensitivity, less signal decay, less negative MRD, smaller MARD, and higher overall correlation than the standard 7 minute integration method or the $S_\infty$ PK method. The methods of the present invention may be useful in increasing the effective monitoring time of a GlucoWatch biographer monitoring device with a single AutoSensor for up to and beyond 24 hours (as opposed to the typical 12-13 hour use period currently seen with the standard 7 minute integration method employed in the GlucoWatch biographer or the GlucoWatch G2 biographer). Further, these parameters ($1/k_2$ and $t/c_2$) may be used as input parameters into other algorithms, for example, MOE, to refine estimates of analyte amount or concentration.

As is apparent to one of skill in the art, various modification and variations of the above embodiments can be made without departing from the spirit and scope of this invention. Such modifications and variations are within the scope of this invention.

What is claimed is:

1. A method of obtaining an analyte value in biological fluid of a user with an analyte sensor having two electrode sets coupled to a microprocessor, the method comprising:
    providing a plurality of data points via the microprocessor by:
        contacting the two electrode sets with biological fluid of a user, in which each electrode set includes an iontophoretic electrode and an electrochemical sensor element in contact with the biological fluid and each of the two iontophoretic electrodes function as either a cathode or anode while in contact with the fluid;
        measuring a total signal from the sensor element associated with the iontophoretic electrodes;
        extracting a signal from the total signal related to the analyte from the sensor element associated with the iontophoretic electrodes to provide the plurality of data points;
    evaluating said data points, via the microprocessor for one or more non-monotonic events and (i) if the data points have an acceptable monotonic trend the measurement signal is accepted for further processing, or (ii) if the data points comprise one or more non-monotonic events then a percent contribution of said one or more non-monotonic events relative to total measurement signal is further evaluated, and if the percent contribution is less than a predetermined threshold value or falls within a predetermined range relative to total measurement signal then the measurement signal is accepted for further processing unless the percent contribution is greater than a predetermined threshold value or falls outside a predetermined range relative to total measurement signal then the measurement signal is not accepted for further processing and skipped;
    integrating, via the microprocessor, the signal related to the analyte over time to obtain a charge signal as being proportional to a value of the analyte; and
    displaying, via the microprocessor, the analyte value of the biological fluid of the user for diagnostic purposes.

2. The method of claim 1, in which the data points that have a monotonic trend comprises one of a current measurement or a charge measurement.

3. The method of claim 1, in which the percent contribution of said one or more non-monotonic events relative to total measurement signal is evaluated by a method comprising using an area under an entire curve created by the data points of an overall signal and comparing a percent contribution of an area under the curve that corresponds to the contribution by said one or more non-monotonic events.

4. The method of claim 1, in which said measurement signal comprises a one of either a current measurement or a charge measurement and the analyte comprises glucose.

5. The method of claim 1, further comprising using an area under an entire curve created by the data points of an overall signal arid comparing a percent contribution of an area under the curve that corresponds to the contribution by said one or more non-monotonic events to determine the percent contribution of said one or more non-monotonic events relative to total measurement signal.

* * * * *